(12) United States Patent
Seela et al.

(10) Patent No.: US 8,057,997 B2
(45) Date of Patent: Nov. 15, 2011

(54) NUCLEIC ACID BINDING COMPOUNDS CONTAINING PYRAZOLO[3,4-D]PYRIMIDINE ANALOGUES OF PURIN-2,6-DIAMINE AND THEIR USES

(75) Inventors: Frank Seela, Osnabrueck (DE); Frank Bergmann, Iffeldorf (DE); Herbert Von Der Eltz, Weilheim (DE); Dieter Heindl, Tutzing (DE); Christoph Seidel, Weilheim (DE); Georg Becher, Osnabrueck (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 1233 days.

(21) Appl. No.: 11/742,416

(22) Filed: Apr. 30, 2007

(65) Prior Publication Data

US 2011/0021365 A1    Jan. 27, 2011

Related U.S. Application Data

(63) Continuation of application No. 10/333,518, filed as application No. PCT/EP01/08850 on Jul. 31, 2001, now Pat. No. 7,238,795.

(30) Foreign Application Priority Data

Aug. 3, 2000 (EP) .................... 00116816
Apr. 24, 2001 (EP) .................... 01109438

(51) Int. Cl.
*C12Q 1/68*    (2006.01)
*C12P 19/34*    (2006.01)
*C07H 21/00*    (2006.01)
*C07H 21/02*    (2006.01)

(52) U.S. Cl. ......... 435/6; 435/91.1; 536/23.1; 536/24.3; 536/26.6

(58) Field of Classification Search ............. 435/6, 91.1; 536/23.1, 24.3, 26.6

See application file for complete search history.

(56) References Cited

FOREIGN PATENT DOCUMENTS

WO        9951775 A1    10/1999

OTHER PUBLICATIONS

Seela, Frank, et al., 1999, "8-AZA-7-Deazapurine DNA: Synthesis and Duplex Stability of Oligonucleotides Containing 7-Substituted Bases", Nucleosides & Nucleotides, 18(6&7):1399-1400.
Garajewa, L.D., et al., 1988, "Synthesis and Study of the Cytotoxic Activity of the Riboside of 4,6-Diaminopyrazolo[3,4-d]pyrimidine and its 3-Carbamoyl Derivative", *Khimiko-Farmat. Zhurnal*, 22:798-802.
Garajewa, L.D., et al., 1989, "Synthesis and Chemical Transformations of 1-β-D-Arabinofuranosides of 3,4,6-Trisubstituted Pyrazolo[3,4-d]pyrimidines", *Bioorg. Khimiya*, 15:249-255.

*Primary Examiner* — Jezia Riley
(74) *Attorney, Agent, or Firm* — Charles M. Doyle; David J. Chang

(57) ABSTRACT

The present invention is in the field of nucleic acid binding compounds comprising 7-substituted 7-deaza-8aza-2,6-diamino-purine bases, compounds useful for the preparation of such compounds, various uses thereof and methods for the determination of nucleic acids using said compounds in the field of diagnostics.

20 Claims, 8 Drawing Sheets

NUCLEIC ACID BINDING COMPOUNDS CONTAINING PYRAZOLO[3,4-D]PYRIMIDINE ANALOGUES OF PURIN-2,6-DIAMINE AND THEIR USES

This application is a continuation of U.S. application Ser. No. 10/333,518, filed Jan. 21, 2003 now U.S. Pat. No. 7,238,795, which is a 35 U.S.C. §371 national phase filing of International Application No. PCT/EP01/08850, filed Jul. 31, 2001, the contents of which are hereby incorporated by reference therein.

BACKGROUND OF THE INVENTION

Sequence Listing

The instant application contains a Sequence Listing which has been submitted in ASCII format via EFS-Web and is hereby incorporated by reference in its entirety. Said ASCII copy, created on Sep. 17, 2010, is named 19071US1.txt and is 14,771 bytes in size.

FIELD OF THE INVENTION

The present invention is in the field of nucleic acid binding compounds comprising 7-substituted 7-deaza-8-aza-2,6-diamino-purine bases, compounds useful for the preparation of such compounds, various uses thereof and methods for the determination of nucleic acids using said compounds in the field of diagnostics.

BACKGROUND OF THE INVENTION

Nucleic acids have been found to be useful analytes for the determination of the presence or absence of genes or microorganisms in human body fluids, food or environment in the field of health care. Nucleic acid analysis has found widespread use after the introduction of nucleic acid amplification, like the Polymerase Chain Reaction (PCR, see U.S. Pat. No. 4,683,202). Thus, sufficient amounts of nucleic acids are available from each sample. The nucleic acids can be determined from this pretreated sample using a variety of different techniques, dependent on the particular purpose. Most assays require the use of a probe which is either immobilized or immobilizable or is labelled by attachment of one or more reporter groups.

A reporter group has the characteristics to be itself capable to be determined or it can be reacted with reagents that make the probe determinable via said reporter group. Thus, for example, probes that are labelled by reporter groups can be determined, as can be hybrids that contain the probe and a nucleic acid to be determined. In case of immobilized probes, the hybrid between the probe and the nucleic acid to be determined is determined at the solid phase to which the probe is bound. In a particular form of assays, not only one nucleic acid having a specific sequence, but a large number of nucleic acids of different sequence is determined. For this purpose, the probes are immobilized in tiny spots in an array on a flat surface such as a glass chip (EP-A-0 476 014 and TIBTECH (1997), Vol. 15, 465-469, WO89/10977, WO89/11548, U.S. Pat. No. 5,202,231, U.S. Pat. No. 5,002,867, WO 93/17126). Further development has provided methods for making very large arrays of oligonucleotide probes in very small areas. (U.S. Pat. No. 5,143,854, WO 90/15070, WO 92/10092). Microfabricated arrays of large numbers of oligonucleotide probes, called "DNA chips" offer great promise for a wide variety of applications (see e.g. U.S. Pat. No. 6,156,501 and U.S. Pat. No. 6,022,963).

However, nucleic acid determinations often suffer from the problem that the base pairing possibilities between the natural bases A and T and C and G have different stability. This can be attributed to the different capability of these bases to form hydrogen bonding. Thus, the dA-dT-base pair has two hydrogen bridges, while the dG-dC-base pair has three hydrogen bridges. This results in different melting temperatures ($T_m$) of hybrids, depending on the GC content [1-3]. The higher the GC content, the higher the $T_m$. The hybridisation strength or the degree of hybridization may be investigated by the measurement of the $T_m$ of the resulting duplex. This can be done by exposing a duplex in solution to gradually increasing temperature and monitoring the denaturation of the duplex, for example, by absorbance of ultraviolet light, which increases with the unstacking of base pairs that accompanies denaturation. The $T_m$ is generally defined as the temperature midpoint of the transition from a fully duplex structure to complete denaturation, i.e. the formation of two isolated single strands.

Therefore in routine nucleic acid analysis, there is often the wish to change the $T_m$ of a nucleic acid molecule. For example, for certain purposes it may be advantageous to equalize or harmonize the $T_m$ of nucleic acids of the same length or to make it even independent from the length of the nucleic acid or the binding region in order to be in the position to apply similar hybridization conditions for all assays. This is particularly necessary for assays using arrays, as on such arrays the hybridizing conditions for each probe must be identical. One solution was the use of low hybridization temperatures. Under such conditions, many nucleic acids having a low degree of base sequence complementarity will bind to the probe. This is called unspecific binding which does not allow discrimination between similar sequences. Another proposal was directed to the use of chemical reagents in the hybridization mixture, for example the addition of tetramethylammonium chloride (TMAC). This reagent reduces the difference between the stability of dG-dC and dA-dT base pairs but the effect is insufficient for short oligonucleotides. Further the addition of salts such as TMAC may not be appreciated as it complicates the optimization of the assay. Another proposal was directed to the use of different concentrations of each different (immobilized) probe in one assay. This was found to be technically complex if not impossible on a chip surface. As a further option the substitution of ribonucleotides in an oligonucleotide composed of deoxyribonucleotides, and vice versa was applied for the adaptation of DNA stability, Hoheisel (1996), Nucleic Acids Res. 24, 430-432.

However, it may be also advantageous to increase the $T_m$ of a given nucleic acid. This is interesting in the field of nucleic acids used for antisense therapy, mismatch discrimination and for nucleic acids used in diagnostics. The nucleic acids may be used as primers or probes. The aim is to allow a more simple design of primers and probes used in multiplex reactions and to synthesize shorter capture probes used on chips, as the chemical synthesis of oligonucleotides on a chip surface used for arrays is not as effective as in routine oligonucleotide synthesis. The relative contribution of each base pair to the melting temperature of a hybrid is the higher the shorter an oligonucleotide is. In consequence, the difference in stability between a mismatch and a perfect match is higher for shorter oligonucleotides. However, short oligonucleotides hybridize weakly and, therefore, the hybridization reaction has to be performed at low stringency. In consequence, the potential higher ability of discrimination between different sequences by shorter oligonucleotides can only be used under conditions of low stringency. It would be of considerable advantage to provide bases which allow to achieve a high level of mismatch discrimination under stringent conditions, in particular for short oligonucleotides at temperatures used e.g. in amplification reactions. Further, there is the desire in the state of the art to use short oligonucleotides with high discriminatory power in arrays as the chemical synthesis of oligonucleotides on solid supports used for arrays is not as effective as in routine synthesis. Therefore, the ability to use shorter oligonucleotides under stringent conditions would be of considerable advantage. If bases are found that lead to an increase of the $T_m$ of an oligonucleotide hybridized to its complementary strand, other bases may then be used in the same oligonucleotide to further adjust the $T_m$ according to the preferences of the test system to be used.

Theoretically, oligonucleotide duplexes forming other tridentate base pairs should exhibit a similar or higher stability, e.g. those with 2-aminoadenine opposite to thymine. Nevertheless, it has been shown that 2-aminoadenine-thymine/uracil base pairs exhibit only a low thermal stability [4-10]. From the data published so far one can conclude that the additional NH$_2$-group of 2'-deoxyadenosin-2-amine (molecule 1 (see below); $n^2A_d$) contributes very little to the base pair stability of a DNA duplex. The $T_m$-increase is in the range of only 1-2° C. Furthermore, this stabilization does not correspond to the total number of $n^2A_d$-residues incorporated in the duplex instead of dA [11]. A stronger stabilization as reported for duplex DNA is found for duplex RNA or for DNA-RNA hybrids [9] [10] [12]. A rather high base pair stability is observed when 2-aminoadenine is introduced into PNA [13] or hexitol nucleic acids [14]. Modified backbones other than of DNA or of RNA appear to enhance the stability of the 2-aminoadenine-thymine/uracil pair.

The unusual behavior of oligonucleotide duplexes containing $n^2A_d$-dT residues is interesting for the development of an adenine-thymine recognition motif showing the same or even a higher stability than a guanine-cytosine base pair. In the following compounds the purine moiety of compound 1 is replaced by an 8-aza-7-deazapurine (pyrazolo[3,4-d]pyrimidine) or a 7-deazapurine (pyrrolo[2,3-d]pyrimidine) leading to nucleosides (2a [15], 2b, 2c or 3 [16], [17] see below).

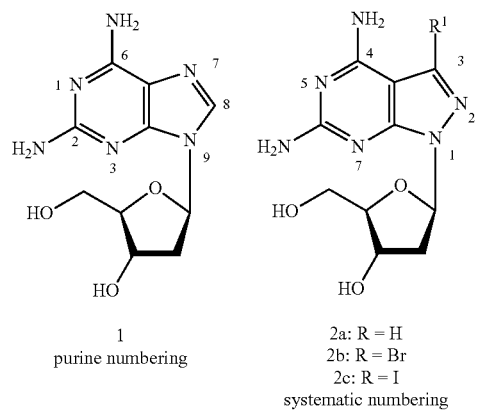

1
purine numbering

2a: R = H
2b: R = Br
2c: R = I
systematic numbering

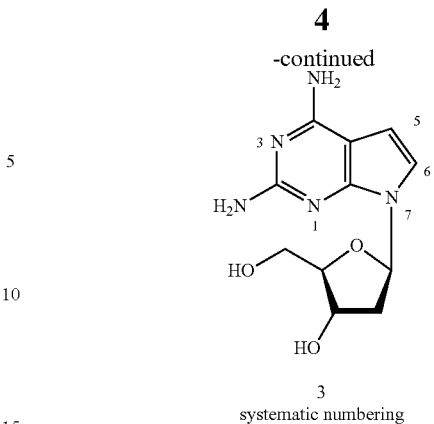

3
systematic numbering

Compounds of similar chemical architecture were investigated in the prior art. The synthesis of 7-substituted-7-deaza and 8-aza-7-deazapurine 2'-deoxyribonucleotides, their incorporation into oligonucleotides, and the stability of the corresponding duplexes has been investigated (Seela et al. (1997) Nucleosides & Nucleotides 16, 963-966). This document does not contain a disclosure of 7-substituted 7-deaza-8-aza-diamino-purines. Stabilization of duplexes by pyrazolopyrimidine base analogues have been reported (Seela et al. (1988) Helv. Chim. Acta 71, 1191-1198; Seela et al. (1988) Helv. Chim Acta 71, 1813-1823; and Seela et al. (1989) Nucleic Acids Res. 17, 901-910)

Pyrazolo[3,4-d]pyrimidine residues in oligonucleotides are also useful as sites of attachment of various groups (WO90/14353). Oligonucleotides having incorporated one or more pyrazolo[3,4-d]pyrimidine have an enhanced tendency to form triplexes (Belousov et al. (1998). Nucleic Acids Res. 26, 1324-1328).

The compounds 7-iodo, 7-cyano and 7-propynyl-7-deaza-2-amino-2'-deoxyadenosine were synthesized by Balow et al. (1997, Nucleosides & Nucleotides 16, 941-944) and incorporated into oligonucleotide sequences. These oligonucleotides exhibit enhanced binding affinities to RNA complements relative to unmodified sequences. However, no corresponding 8-aza-compounds were made and investigated. Seela et al. (1999, Nucleosides & Nucleotides 18, 1399-1400) disclose 7-substituted 8-aza-7-deazapurine DNA, its synthesis and duplex stability. The authors do not address possible uses of the disclosed compounds.

WO 90/03370 discloses 3,4-disubstituted and 3,4,6-trisubstituted pyrazolo-[3,4-d]-pyrimidines, more particularly 4,6-diamino-pyrazolo-[3,4-d]-pyrimidines with a linker at the C3-position to which an intercalator, an electrophilic cross linker or a reporter group is attached. These compounds may be attached to sugars or incorporated into oligonucleotides and thereby used for the identification, isolation, localization and/or detection of complementary nucleic acid sequences of interest. U.S. Pat. No. 5,594,121 discloses novel oligomers with enhanced abilities to form duplexes or triplexes. The oligomers may contain 7-substituted 8-aza-7-deaza-diamino-purines with propinyl and aryls as substituents at the 7-position. Compositions containing these oligomers may used for diagnostic purposes.

There is still a need to provide probes with a high discriminatory power and with a short length, the $T_m$ of which is high under stringent conditions and which can be used in various methods useful in the field of diagnostics as e.g. in the Lightcycler® system (Roche, Mannheim, Germany), TaqMan®

(WO92/02638 and corresponding U.S. Pat. Nos. 5,210,015, 5,804,375, 5,487,972) or other applications involving fluorescence energy transfer.

TERMS AND DEFINITIONS

Conventional techniques of molecular biology and nucleic acid chemistry, which are within the skill of the art, are fully explained fully in the literature. See, for example, Sambrook et al., 1989, Molecular Cloning—A Laboratory Manual, Cold Spring Harbor Laboratory, Cold Spring Harbor, N.Y.; Oligonucleotide Synthesis (M. J. Gait, ed., 1984); Nucleic Acid Hybridization (B. D. Hames and S. J. Higgins. eds., 1984); and a series, Methods in Enzymology (Academic Press, Inc.), all of which are incorporated herein by reference. All patents, patent applications, and publications mentioned herein, both supra and infra, are incorporated herein by reference The terms "nucleic acid" and "oligonucleotide" refer to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA. The term "polynucleotide" shall be used interchangeably for "nucleic acid".

The term "backbone" or "nucleic acid backbone" for a nucleic acid binding compound according to the invention refers to the structure of the chemical moiety linking nucleobases in a nucleic acid binding compound. The bases are attached to the backbone and take part in base pairing to a complementary nucleic acid binding compound via hydrogen bonds. This may include structures formed from any and all means of chemically linking nucleotides, e.g. the natural occurring phosphodiester ribose backbone or unnatural linkages as e.g. phosphorthioates, methyl phosphonates, phosphoramidates and phosphortriesters. Peptide nucleic acids have unnatural linkages. Therefore, a "modified backbone" as used herein includes modifications to the chemical linkage between nucleotides as described above, as well as other modifications that may be used to enhance stability and affinity, such as modifications to the sugar structure. For example an α-anomer of deoxyribose may be used, where the base is inverted with respect to the natural β-anomer. In an embodiment, the 2'-OH of the sugar group may be altered to 2'-O-alkyl or 2'-O-alkyl-n(O-alkyl), which provides resistance to degradation without comprising affinity. An unmodified nucleotide sequence having a phosphodiester backbone is "comparable" to a nucleobase-containing sequence having a modified backbone if the two sequences have identical base sequencing. Thus, the backbones of such sequences are also comparable.

The term "nucleic acid binding compound" refers to substances which associate with nucleic acids of any sequence and are able to function as binding partner to a substantially complementary nucleic acid. The binding preferably occurs via hydrogen bonding between complementary base pairs when the nucleic acid binding compound is in a single-stranded form. Preferably, non-natural bases, the subject of the invention, attached to the backbone of the nucleic acid binding compound may be also involved in hydrogen-bonding, however, these may also be able to form hydrogen bonds to only some or all natural occurring bases as e.g. inosine. The expert in the field recognizes that the most well-known "nucleic acid binding compounds" are nucleic acids as DNA or RNA.

The term "probe" refers to synthetic or biologically produced nucleic acids (DNA or RNA) which, by design or selection, contain specific nucleotide sequences that allow them to hybridize under defined predetermined stringencies, specifically (i.e., preferentially) to target nucleic acids. A "probe" can be identified as a "capture probe" meaning that it "captures" the target nucleic acid so that it can be separated from undesirable materials which might obscure its detection. Once separation is accomplished, detection of the captured target nucleic acid can be achieved using a suitable procedure. "Capture probes" are often already attached to a solid phase.

The term "hybridization" refers the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which only fully complementary nucleic acid strands will hybridize are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair concentration of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, N.Y.; and Wetmur, 1991, Critical Review in Biochem. and Mol. Biol. 26(3/4):227-259; both incorporated herein by reference).

The term "primer" refers to an oligonucleotide capable of acting as a point of initiation of DNA synthesis under conditions in which synthesis of a primer extension product complementary to a nucleic acid strand is induced, i.e., either in the presence of four different nucleoside triphosphates and an agent for extension (e.g., a DNA polymerase or reverse transcriptase) in an appropriate buffer and at a suitable temperature. As used herein, the term "primer" is intended to encompass the oligonucleotides used in ligation-mediated amplification processes, in which one oligonucleotide is "extended" by ligation to a second oligonucleotide which hybridizes at an adjacent position. Thus, the term "primer extension", as used herein, refers to both the polymerization of individual nucleoside triphosphates using the primer as a point of initiation of DNA synthesis and to the ligation of two primers to form an extended product. A primer is preferably a single-stranded DNA. The appropriate length of a primer depends on the intended use of the primer but typically ranges from 6 to 50 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein. Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning of the amplified product. The region of the primer which is sufficiently complementary to the template to hybridize is referred to herein as the hybridizing region.

The terms "target, "target sequence", "target segment", "target region", and "target nucleic acid" refer to a region or subsequence of a nucleic acid which is to be amplified or investigated.

As used herein, a primer is "specific" for a target sequence if the number of mismatches present between the primer sequence and the target sequence is less than the number of mismatches present between the primer sequence and non-target sequences which may be present in the sample. Hybridization conditions can be chosen under which stable duplexes are formed only if the number of mismatches present is no more than the number of mismatches present between the primer sequence and the target sequence. Under such conditions, the primer can form a stable duplex only with a target sequence. Thus, the use of target-specific primers under suitably stringent amplification conditions enables the specific amplification of those target sequences which contain the target primer binding sites. The use of sequence-specific amplification conditions enables the specific amplification of those target sequences which contain the exactly complementary primer binding sites.

Halogen means a fluoro, chloro, bromo or iodo group. The most preferred halogen groups are —I and —Br.

Alkyl groups are preferably chosen from alkyl groups containing from 1 to 10 carbon atoms, either arranged in linear, branched or cyclic form. The actual length of the alkyl group will depend on the steric situation at the specific position where the alkyl group is located. If there are steric constraints, the alkyl group will generally be smaller, the methyl and ethyl group being most preferred. All alkyl, alkenyl and alkynyl groups can be either unsubstituted or substituted. Substitution by hetero atoms as outlined above, will help to increase solubility in aqueous solutions.

Alkenyl groups are preferably selected from alkenyl groups containing from 2 to 10 carbon atoms. For the selections similar considerations apply as for alkyl groups. They also can be linear, branched and cyclic. The most preferred alkenyl group is the ethylene group.

Alkynyl groups have preferably from 2 to 10 carbon atoms. Again, those carbon atoms can be arranged in linear, branched and cyclic manner. Further, there can be more than one triple bond in the alkynyl group. The most preferred alkynyl group is the 3-propargyl-group.

Alkoxy groups preferably contain from 1 to 6 carbon atoms and are attached to the rest of the moiety via the oxygen atom. For the alkyl group contained in the alkoxy groups, the same considerations apply as for alkyl groups. The most preferred alkoxy group is the methoxy group.

By "aryl" and "heteroaryl" (or "heteroaromatic") is meant a carbocyclic or heterocyclic group comprising at least one ring having physical and chemical properties resembling compounds such as an aromatic group of from 5 to 6 ring atoms and comprising 4 to 20 carbon atoms, usually 4 to 9 or 4 to 12 carbon atoms, in which one to three ring atoms is N, S or O, provided that no adjacent ring atoms are O—O, S—S, O—S or S—O. Aryl and heteroaryl groups include, phenyl, 2-, 4- and 5-pyrimidinyl, 2-, 4- and 5-thiazoyl, 2-s-triazinyl, 2-, 4-imidazolyl, 2-, 4- and 5-oxazolyl, 2-, 3- and 4-pyridyl, 2- and 3-thienyl, 2- and 3-furanyl, 2- and 3-pyrrolyl optionally substituted preferably on a ring C by oxygen, alkyl of 1-4 carbon atoms or halogen. Heteroaryl groups also include optional substitution on a ring N by alkyl of 1-4 carbon atoms or haloalkyl of 1-4 carbon atoms and 1-4 halogen atoms. Exemplary substituents on the aryl or heteroaryl group include methyl, ethyl, trifluoromethyl and bromo. Such substituted aryl and heteroaryl groups include benzyl and the like. "Heteroaryl" also means systems having two or more rings, including bicyclic moieties such as benzimidazole, benzotriazole, benzoxazole, and indole. Aryl groups are the phenyl or naphtyl moiety, either unsubstituted or substituted by one or more of amino, -cyano, -aminoalkyl, —O—($C_1$-$C_{10}$)-alkyl, —S—($C_1$-$C_{10}$)-alkyl, —($C_1$-$C_{10}$)-alkyl, sulfonyl, sulfenyl, sulfinyl, nitro and nitroso. Most preferred aryl group is the phenyl group. Preferred arylalkyl group is the benzyl group. The preferred alkylamino group is the ethylamino group. The preferred —COO($C_1$-$C_4$) alkyl group contains one or two carbon atoms in the alkyl moiety (methyl or ethyl esters). Other aryl groups are heteroaryl groups as e.g. pyrimidine, purine, pyrrol, or pyrazole. Aryl and heteroaryl. According to the present invention the term aryl shall also include all heteroaryls.

Aryloxy groups preferably contain from 6 to 20 carbon atoms. Those carbon atoms may be contained in one or more aromatic rings and further in side chains (for example, alkyl chains) attached to the aromatic moiety. Preferred aryloxy groups are the phenoxy and the benzoxy group.

A "protecting group" is a chemical group that is attached to a functional moiety (for example to the oxygen in a hydroxyl group or the nitrogen in an amino group, replacing the hydrogen) to protect the functional group from reacting in an undesired way. A protecting group is further defined by the fact that it can be removed without destroying the biological activity of the molecule formed, here the binding of the nucleic acid binding compound to a nucleic acid. Suitable protecting groups are known to a man skilled in the art. Especially preferred protecting groups for example for hydroxyl groups at the 5'-end of a nucleotide or oligonucleotide are selected from the trityl groups, for example dimethoxytrityl. Preferred protecting groups at exocyclic amino groups in formula I are acyl groups, most preferred the benzoyl group (Bz), phenoxyacetyl or acetyl or formyl, and the amidine protecting groups as e.g. the N,N-dialkylformamidine group, preferentially the dimethyl-, diisobutyl-, diisobutyryl and the di-n-butylformamidine group. Preferred O-protecting groups are the aroyl groups, the diphenylcarbamoyl group, the acyl groups, and the silyl groups. Among these most preferred is the benzoyl group. Preferred silyl groups are the trialkylsilyl groups, like, trimethylsilyl, triethylsilyl and tertiary butyl-dimethyl-silyl. Another preferred silyl group is the trimethylsilyl-oxy-methyl group (TOM)(Swiss Patent Application 01931/97). Further, preferred protecting groups are groups as ortho nitrobenzyl protecting groups like 2-(4-nitrophenyl) ethoxycarbonyl (NPEOC) or photoactivable compounds as 2-nitrophenylpropyloxycarbonyl (NPPOC) (Giegrich et al., Nucleosides & Nucleotides 1998, 17, 1987). According to the invention, also the phthaloyl group may be used as protecting group.

Any atom in the definitions within the formulae presented herein is not limited to a specific isotope. Thus, a phosphorous atom (P) can either mean the regular $^{31}$P or the radioactive $^{32}$P or a mixture thereof. The same applies for hydrogen (H/D/T), carbon (C), iodine (Cl, Br, I) and nitrogen (N).

During chemical synthesis, any reactive groups as e.g. —OH, —SH, —$NH_2$, —NH-alkyl, —NH-alkenylene, —NH-alkynylene, or —NH-aryl (including those groups in reporter groups) should be protected by suitable protecting groups, i.e. that the present invention contemplates compounds for the synthesis of olignucleotides wherein the formulas or substituents are chosen with the proviso that one or two hydrogen atoms of any —OH, —SH, —NH$_2$, —NH-alkyl, —NH-alkenylene, —NH— alkynylene, or —NH-aryl group are substituted by a protecting group. Further, during chemical synthesis, the compound will be attached for convenience to a solid phase. In these cases, the definitions of the substituents given above will be selected accordingly.

Reporter groups are generally groups that make the nucleic acid binding compound as well as any nucleic acids bound thereto distinguishable from the remainder of the liquid, i.e. the sample (nucleic acid binding compounds having attached a reporter group can also be termed labeled nucleic acid binding compounds, labeled probes or just probes). The term reporter group and the specific embodiments preferably include a linker which is used to connect the moiety intended to be used (the actual solid phase or the fluorophoric moiety) to the position of attachment as the reporter group. The linker will provide flexibility such that the nucleic acid binding compound can bind the nucleic acid sequence to be determined without major hindrance by the solid phase. Linkers, especially those that are not hydrophobic, for example based on consecutive ethylenoxy units, for example as disclosed in DE 3943522 are known to a man skilled in the art.

By "array" is meant an arrangement of addressable locations on a device. The locations can be arranged in two dimensional arrays, three dimensional arrays, or other matrix formats. The number of locations can range from several to at least hundreds of thousands. Most importantly, each location represents a totally independent reaction site. Each location carries a nucleic acid binding compound which can serve as a binding partner for a second nucleic acid binding compound, a nucleic acid, in particular a target nucleic acid.

The term "building block" or "subunit" refers to a compound which can be used in oligonucleotide synthesis wherein subsequently single building blocks are chemically linked to form a more complex structure, i.e. an oligonucleotide precursor. Examples for building blocks are phosphoramidites or phosphonates.

The term "substituted compound" shall mean that a compound carries further chemical groups, moieties or substituents other than the compound itself. These substituents shall in principle include but are not limited to halogens or alkyl, alkenyl, alkynyl, or aryl compounds optionally substituted with further heteroatoms

BRIEF DESCRIPTION OF THE FIGURES

FIG. 1a: Ultraviolett spectra of demination of compound 2a

DETAILED DESCRIPTION OF THE INVENTION

Figure 1A:
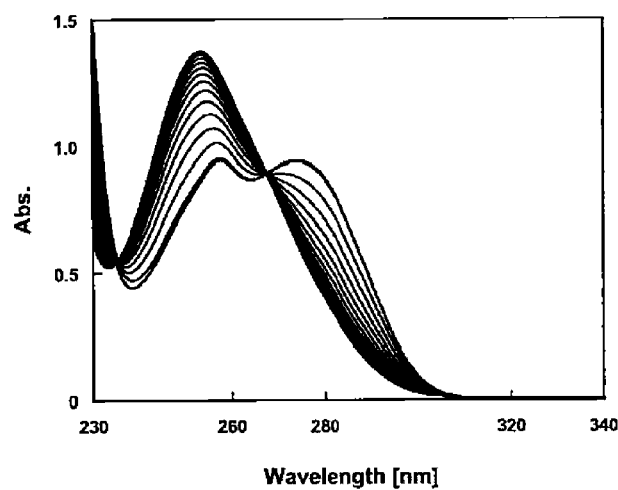

The above-mentioned problem could be solved by the findings of the present invention which discloses nucleic acid binding compounds wherein 7-substituted 8-aza-7-deaza-2,6-diamino-purines are incorporated, derivatives of these oligonucleotides and compounds useful for the synthesis thereof. Further, the present invention discloses methods wherein the compounds according to the present invention may be used.

Surprisingly, an oligonucleotide having incorporated a 7-iodo or 7-bromo-8-aza-7-deaza-2,6-diamino-purine in place of an adenine residue shows an unexpected increase in the melting temperature. This finding is in contrast to the behaviour of 5-halogen substituted pyrimidines. This effect can be observed for parallel as well as for antiparallel duplexes. These findings could not be foreseen on the basis of the state of the art, however, the surprising finding can be generalized to other 8-aza-7-deaza-2,6-diamino-purines substituted at the 7-position (purine numbering) with a hydrophobic residue as the halogen substituent is hydrophobic or a residue containing a hydrophobic moiety attached to the 7-position. Further, the teachings can be generalized to an electron-withdrawing substituent. Therefore, preferred other substituents at this position as e.g. alkyl, alkenyl and alkinyl, preferably with a length of 6 carbon atoms, more preferably with a length of 3 carbon atoms, are suitable in the present invention. The 7-position allows the substituents to extend into the major groove of the DNA where they find enough space and do not disturb the DNA double helix. A possible explanation for this effect could be removal of water from the major groove and the concomitant hydrophobisation of the major groove thereby increasing the stacking of the DNA bases. Substituents fulfilling these requirements may also carry other functional groups as e.g. reporter groups.

In summary, the present invention discloses nucleic acid binding compounds comprising 7-substituted 7-deaza-8-aza-2,6-diamino-purine bases, compounds useful for the preparation of such compounds, various uses thereof and methods for the determination of nucleic acids using said compounds in the field of diagnostics.

The subject of the present invention is a nucleic acid binding compound comprising a backbone, said backbone having attached heterocyclic groups capable of base pairing to nucleobases characterized in that a heterocyclic group is a group of the general Formula I

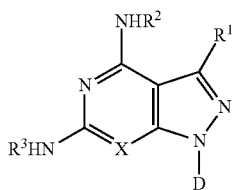

Formula I wherein
R1 is independent from X, R2 or R3 and is selected from the group consisting of
(1) —F, —Cl, —Br or —I,
(2) Nitro
(3) Cyano
(4) —COO—
(5) —(C1-C10)-alkyl substituted according to (10)
(6) —(C2-C10)-alkenyl substituted according to (10)
(7) —(C2-C10)-alkynyl substituted according to (10)
(8) —(C6-C22)-aryl substituted according to (10)
(9) —W—(C1-C10)-alkyl, —W—(C2-C10)-alkenyl, —W—(C2-C10)-alkynyl, —W—(C6-C22)-aryl or W—H, wherein W=—S—, —O—, —NH—, —S—S—, —CO—, —COO—, —CO—NH—, —NH—CO—, —NH—CO—NH—, —NH—CS—NH—, —(CH2)n-[O—(CH2)r]s-, where r and s are, independently of each other, an integer between 1 to 18 and n is 0 or 1 independently from r and s,
(10) substituents (5) to (9) wherein any alkyl, alkenyl, alkynyl or aryl can be substituted by one or more moieties selected from the group consisting of -halogen, —SH, —NO2, —CN, —S—(C1-C6)-alkyl, —NR5R6, —N+R5R6R12, —OR12, —COR11, —NH—CO—NR5R6, —NH—CS—NR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12, OR12, and —SR12
wherein R5, R6 and R12 are selected independently from the group consisting of —H, —(C1-C10)-alkyl, —(C2-C10)-alkenyl, —(C2-C10)-alkinyl, —(C6-C22)-aryl and a reporter group, a group which facilitates intracellular uptake or a group that, when the nucleic acid binding compound hybridizes to its complementary nucleic acid, attacks the latter while binding, cross-linking or cleaving,
said alkyl, alkenyl, alkynyl or aryl in substituents (5) to (10) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
with the proviso that R5, R6 or R12 is not a reporter group if the radicals (5) to (7) are substituted by —NR5R6, NHR12, OR12, or SR12;
R2, R3 is independent from X, R1, R2 and R3 and is selected from the group of,
(1) —H
(2) (C1-C10)-alkyl,
(3) (C2-C10)-alkenyl,
(4) (C2-C10)-alkynyl,
(5) (C6-C22)-aryl,
(6) —Z—(C1-C10)-alkyl, —Z—(C2-C10)-alkenyl, —Z—(C2-C10)-alkynyl, —Z—(C6-C22)-aryl or Z—H, wherein Z=—CO—, —CO—NH—, —CS—NH—, —(CH2)n-[O—(CH2)r]s-, where r and s are, independently of each other, an integer between 1 to 18 and n is 1 or 2 independently from r and s,
(7) substituents (2) to (6)
wherein any alkyl, alkenyl, alkynyl or aryl can be substituted by one or more moieties selected from the group consisting of -halogen, —NO2, —OR12, —CN, —SH, —S—(C1-C6)-alkyl, —NR5R6, —N+R5R6R12, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12 and OR12,
wherein R5, R6 and R12 are selected independently from the group consisting of —H, —(C1-C10)-alkyl, —(C2-C10)-alkenyl, —(C2-C10)-alkynyl, —(C6-C22)-aryl and a reporter group,
said alkyl, alkenyl, alkynyl or aryl in substituents (2) to (7) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s;
X is independent from $R^1$, $R^2$ or $R^3$ and is selected from the group consisting of N and CH
D is the position of attachment of the group to the rest of the nucleic acid binding compound.
and any salts thereof.

The nucleobases, to which the nucleic acid binding compound according to the invention may bind, can be nucleobases occurring in nature, as e.g. adenosine, guanosine, uridin or cytidin or the 2'-desoxyderivatives thereof, or nucleobases not occurring in nature as e.g. nucleobases with heterocyclic groups according to the invention, heterocyclic groups as pyrrolo-[2,3-d]-pyrimidine or pyrazolo[3,4-d]-pyrimidine or analogues thereof, preferably the said analogues of guanine or adenine or 7-deaza-guanine. Other non-natural heterocyclic groups are known to the person skilled in the art and need not to be mentioned explixitly herein.

In another preferred embodiment, the invention relates to nucleic acid binding compounds with the general formula I and residues $R^2$ and $R^3$ as defined above, that have electron-withdrawing or hydrophobic substituents at the 7-position of 7-deaza-8-aza-2,6-diamino-purine. Therefore, in addition to the preferred halogen substituents other preferred substituents at the 7-position are hydrophobic in nature as e.g. alkyl, alkenyl and alkinyl residues. It is, however, sufficient if the first residues extending into the major groove are hydrophobic. In detail, other preferred substituents at the 7-position are the residues
(1) —($C_1$-$C_{10}$)-alkyl substituted according to (5)
(2) —($C_2$-$C_{10}$)-alkenyl substituted according to (5)
(3) —($C_2$-$C_{10}$)-alkynyl substituted according to (5)
(4) —($C_6$-$C_{22}$)-aryl substituted according to (5)
(5) substituents (1) to (4) wherein any alkyl, alkenyl, alkynyl or aryl can be substituted by one or more moieties selected from the group consisting of -halogen, —SH, —CN, —S—($C_1$-$C_6$)-alkyl, —$NR^5R^6$, —$N^+R^5R^6R^{12}$, —$OR^{12}$, —$COR^{11}$, —NH—CO—$NR^5R^6$, —NH—CS—$NR^5R^6$ and —$(CH_2)_n$-[O—$(CH_2)_r$]$_s$—$NR^5R^6$, r and s are independently of each other an integer of from 1 to 18 and n is 0 or 1 independently from r and s, wherein $R^{11}$ is selected from the group consisting of —$NHR^{12}$, $OR^{12}$, and —$SR^{12}$ wherein $R^5$, $R^6$ and $R^{12}$ are selected independently from the group consisting of —H, —($C_1$-$C_{10}$)-alkyl, —($C_2$-$C_{10}$)-alkenyl, —($C_2$-$C_{10}$)-alkinyl, —($C_6$-$C_{22}$)-aryl and a reporter group, a group which facilitates intracellular uptake or a group that, when the nucleic acid binding compound hybridizes to its complementary nucleic acid, attacks the latter while binding, cross-linking or cleaving, said alkyl, alkenyl, alkynyl or aryl in substituents (1) to (4) being unsubstituted or substituted by one or more moieties selected from the group consisting of -halogen, —SH, —S—($C_1$-$C_6$)-alkyl, —($C_1$-$C_6$)-alkoxy, —OH, —$NR^5R^6$, —$COR^{11}$, —NH—$CONR^5R^6$, —NH—$CSNR^5R^6$ and —$(CH_2)_n$-[O—$(CH_2)_r$]$_s$—$NR^5R^6$, r and s are independently of each other an integer of from 1 to 18 and n is 0 or 1 independently from r and s, with the proviso that $R^5$, $R^6$ or $R^{12}$ is not a reporter group if the radicals (1) to (3) are substituted by —$NR^5R^6$, $NHR^{12}$, $OR^{12}$, or $SR^{12}$;

More preferably, the residue (1) has a length of between 1 and 6 carbon atoms, more preferably a length of between 1 to 3 carbon atoms, and the residues (2) and (3) have a length of between 2 and 6 carbon atoms, more preferably a length of between 2 to 3 carbon atoms.

In the most preferred embodiment the heterocyclic group is 7-bromo-7-deaza-8-aza-2,6-diamino-purine or 7-iodo-7-deaza-8-aza-2,6-diamino-purine. The nucleic acid binding compounds according to the invention further possess the advantage of having a very stable glycosidic bond in contrast to 2-amino-adenosine which has an extremely acid labile glycosidic bond and may only be used in oligonucleotide synthesis if specific conditions are used. In a further embodiment of the invention, the halogenides in the 7-position of the 7-deaza-8-aza-2,6-diamino-purine may be substituted by pseudohalogenides as e.g. —SCN or —CN.

The preferred substituents mentioned above are also preferred in the methods and uses according to the present invention.

The heterocyclic groups of formula I are mainly characterized by the following properties:

The base is linked to the backbone, preferred to a sugar moiety, via the 9-position (purine numbering).

The base contains an aromatic □-electron system which is capable to form stacking interactions with other nucleic acid constituents.

The base contains donor and/or acceptor site(s) for hydrogen bonding to the natural nucleoside T.

In order to increase the $T_m$, in a nucleic acid binding compound one or more. A in a strand complementary to a T in the nucleic acid to be determined could be replaced by the heterocyclic groups according to the invention. The oligonucleotide would then bind specifically to the target sequence containing T opposite to the bases according to the invention with a binding energy in the order of a G-C base pair but with higher stability than a A-T base pair. This works for antiparallel or parallel duplexes equally well whereby natural A-T base pairs have equal abilities to bind in parallel or antiparallel duplexes but with a lower binding energy in the parallel duplex. However, the heterocyclic group according to the invention, when incorporated into a nucleic acid binding compound, will bind to a T in the opposite strand equally well in a parallel or in an antiparallel duplex. In order to effect antiparallel binding in a duplex, natural G or C bases normally forming G-C base pairs in antiparallel duplexes have to be substituted by non-natural base pairs as e.g. G-iC (isocytosine) or better G-$^{me}$-C (methylated isocytosine) or C-iG (isoguanosine) as disclosed above. A summary of parallel and antiparallel duplexes can be found in EP 0 624 161 or Seela et al. (Tetrahedron 55 (1999), 9481-9500) and is shown schematically in scheme 11 and 12 in example 4.

This general principle of course is not limited, as bases showing the same characteristics in the 6-membered ring would be expected to have the same properties based on the above explanation due to their containing the structure according to the invention. Particularly, the farer the part of the heterocyclic group from the part participating in the base pairing, the more tolerant will the oligomer be over modifications in the chemical structure, for example the attachment of groups to this part of the heterocyclic rings. In the following, when reference is made to the heterocyclic group of the invention, there is made reference to a heterocyclic group according to general formula I.

The present invention also contemplates tautomeric forms and salts of heterocyclic groups of formula I.

The nucleic acid binding compound according to the invention preferably has a length of less than 100 subunits, more preferably of from 10 to 30 subunits. In order to be active as nucleic acid binding compound, the substituents should be chosen such that hydrogen bonds to heterocyclic groups at the nucleic acid to be bound are enabled, preferably by base pairing, for example by Watson-Crick or Hoogsteen base pairing. Compounds in which the substituents do not enable such preferred hydrogen bonding, can be useful as intermediates for the preparation of nucleic acid binding compounds. Preferred nucleic acid binding compounds of the invention are those which are chemically synthesized.

The nucleic acid binding compound will be constructed such that it contains a nucleobase sequence which is substantially complementary to the nucleic acid to be determined or the nucleic acid to which it is intended to be bound by base pairing dependent on the formation of a parallel or an antiparallel duplex. As those nucleic acids will usually contain at least once any of the naturally occurring nucleobases Ade, Cyt, Gua and Thy or Ura, the nucleic acid binding compound according to the invention will also contain any of those four bases. However, according to the invention, at least one of the heterocyclic groups is replaced by the heterocyclic base of formula I.

If the nucleic acid binding compound is to be used as a probe for the determination of a nucleic acid, or any other identification of the compound or the nucleic acid is intended, any of the substituents are selected such as to contain a reporter group. While as many reporter groups can be attached as useful to label the nucleic acid binding compound sufficiently, it is preferred to attach only a limited number of reporter groups to a single subunit, such that recognition of nucleic acids, affinities to nucleic acids and solubility is not affected such that the probe would not be useful in hybridization assays. In a very preferred case, there will be only from 1 to 4, most preferably 1 or 2 or most preferred only one reporter group in each nucleic acid binding compound. There are formats for the nucleic acid determination which require more than one reporter group attached to the probe. An example for such formats is disclosed in WO92/02638. In this case, one of the reporter groups will be a fluorescence emitter, while the other is a fluorescence quencher. The reporter group may also be attached to a heterocyclic base which is not according to formula I.

In a preferred embodiment of the invention, $R^1$ is alkynyl-amino-C≡C-E-$NR^5R^6$, alkenyl-amino —CH=CH-E-$NR^5R^6$ and -E-$NR^5R^6$ wherein E is —[(CH$_2$)$_r$F]$_s$—(CH$_2$)$_r$— wherein F=O or S and r and s are independently from one another an integer from 1 to 18, wherein $R^5$ and $R^6$ are selected independently from the group consisting of —H, —(C$_1$-C$_{10}$)-alkyl, —(C$_2$-C$_{10}$)-alkenyl, —(C$_2$-C$_{10}$)-alkynyl, —(C$_6$-C$_{22}$)-aryl and a reporter group, wherein $R^{11}$ is selected from the group consisting of —NH$R^{12}$ and O$R^{12}$, wherein $R^5$, $R^6$ and $R^{12}$ are selected independently from the group consisting of —H, —(C$_1$-C$_{10}$)-alkyl, —(C$_2$-C$_{10}$)-alkenyl, —(C$_2$-C$_{10}$)-alkynyl, —(C$_6$-C$_{22}$)-aryl and a reporter group, said alkyl, alkenyl, alkynyl or aryl being unsubstituted or substituted by one or more moieties selected from the group consisting of -halogen, —SH, —S—(C$_1$-C$_6$)-alkyl, —(C$_1$-C$_6$)-alkoxy, —OH, —N$R^5R^6$, —CO$R^{11}$, —NH—CON$R^5R^6$, —NH—CSN$R^5R^6$ and —(CH$_2$)$_n$—[O—(CH$_2$)$_r$]$_s$—N$R^5R^6$, r and s are independently of each other an integer of from 1 to 18 and n is 0 or 1 independently from r and s.

Reporter groups are generally groups that make the nucleic acid binding compound as well as any nucleic acids bound thereto distinguishable from the remainder of the liquid, i.e. the sample (nucleic acid binding compounds having attached a reporter group can also be termed labeled nucleic acid binding compounds, labeled probes or just probes). This distinction can be either effected by selecting the reporter group from the group of directly or indirectly detectable groups or from the groups of immobilized or immobilizable groups. Directly detectable groups are for example fluorescent compounds, like fluorescein and its derivatives, like hexachlorofluorescein and hexafluorofluorescein, rhodamines, psoralenes squaraines, porphyrins, fluorescent particles, bioluminescent compounds, like acridinium esters and luminol, or the cyanine dyes, like Cy-5. Examples of such compounds are disclosed in EP 0 680 969. Further, spin labels like TEMPO, electrochemically detectably groups, ferrocene, viologene, heavy metal chelates and electrochemiluminescent labels, like ruthenium bispyridyl complexes, and naphthoquinones, quencherdyes, like dabcyl, and nuclease active complexes, for example of Fe and Cu, are useful detectable groups. Other examples of such compounds are europium complexes. Indirectly detectable groups are groups that can be recognized by another moiety which is directly or indirectly labelled. Examples of such indirect detectable groups are haptens, like digoxigenin or biotin. Digoxigenin for example can be recognized by antibodies against digoxigenin. Those antibodies may either be labelled directly or can be recognized by labelled antibodies directed against the (anti-digoxigenin) antibodies. Formats based on the recognition of digoxigenin are disclosed in EP-B-0 324 474. Biotin can be recognized by avidin and similar compounds, like streptavidin and other biotin binding compounds. Again, those compounds can be labelled directly or indirectly. Further interesting labels are those directly detectable by atomic force microscopy (AFM) or scanning tunneling microscopy (STM). The reporter group can further be a nucleotide sequence which does not interfere with other nucleotide sequences in the sample. The sequence can therefore be specifically recognized by nucleotide containing a complementary sequence. This nucleotide sequence can be labelled directly or indirectly or can be immobilizable or immobilized. A reporter group can further be a solid phase. Attachment of the nucleic acid binding compound with solid phase can be either directly or indirectly as pointed out above for the detectable group. Examples of such solid phases are latex beads or gold particles. In another embodiment of the invention, a further reporter group attached to the nucleic acid binding compound may be any positively or negatively charged group, preferably a carboxylate group or an ammonium $N^+R^5R^6R^{12}$ with substituents as specified under formula I as described above. These may be attached e.g. via a propargylen linker to the base and enhance the sensitivity of MALDI-TOF mass spectroscopy (MALDI-TOF: matrix-assisted laser desorption/ionization time-of-flight) in the positive or negative mode. The substituents of the ammonium group are preferably introduced into the oligonucleotide via post-labelling, i.e. binding compounds can be postlabeled with reporter groups when a suitable reactive group is introduced during oligonucleotide synthesis, for example, an amino group protected in the oligonucleotide synthesis precursor with a phthaloyl group.

Direct labelling can be effected by covalent coupling of a nucleic acid binding compound to a reactive group on the solid phase, i.e. preferably via a linker. Indirect labelling can be made similar as disclosed above for the detectable groups. Preferably, indirect attachment is non-covalently by biospecific interactions, for example those selected from the group of hapten-antibody, vitamin-receptor and nucleic acid-complementary nucleic acid. Again, those interactions and their use in nucleic acid assays is known to a man skilled in the art.

Solid phases that are useful for immobilization of the probe according to the invention are preferably selected from the group of polystyrene, polyethylene, polypropylene, glass, $SiO_2$ and $TiO_2$. The formats of such solid phases can be selected according to the needs of the instrumentation and format of the assay. For example, a solid phase may assume the form of a bead or a vessel.

The most popular backbone is the naturally occurring sugar phosphate backbone of nucleic acids containing either ribonucleoside subunits (RNA) or deoxyribonucleoside subunits (DNA). Therefore, in a preferred embodiment, the backbone of the nucleic acid binding compound comprises phosphodiester linkages and ribose. In the last years, there were descriptions of nucleic binding compounds that have similar properties like oligonucleotides, but differ in their backbone, which have structures formed from any and all means of chemically linking nucleotides in contrast to the natural occurring phosphodiester ribose backbone. Therefore, it is evident that the invention would still work, even if the backbone of the nucleic acid binding compound is not an oligonucleotide in the strict sense, i.e. it has a modified backbone. The backbone may include e.g. phosphorothioates, methyl phosphonates, phosphoramidates and phosphorotriesters linkages. Peptide nucleic acids also have unnatural linkages. The modifications in the backbone may vary the properties of the nucleic acid binding compound, i.e. it may enhance stability and affinity. Therefore, in a preferred embodiment, the nucleic acid binding compounds are those, wherein the backbone comprises one or more moieties of the general formula II

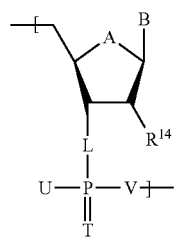

Formula II wherein
A is selected from the group consisting of O, S, CH$_2$, N—CO—(C$_1$-C$_{10}$)-alkyl,
L is selected from the group consisting of oxy, sulfanediyl, —CH$_2$— and —NR$^{22}$—,
T is selected from the group consisting of oxo, thioxo and selenoxo,
U is selected from the group consisting of —OH, O$^-$, —O-reporter group, —SH, —S reporter group —SeH, —(C$_1$-C$_{10}$)-alkoxy, (C$_1$-C$_{10}$)-alkyl, —(C$_6$-C$_{22}$)-aryl, —(C$_6$-C$_{14}$)-aryl-(C$_1$-C$_{10}$)-alkyl, —NR$^{23}$R$^{24}$, and —(-O—(C$_1$-C$_{10}$)-alkyl-)$_n$-R$^{25}$, wherein n can be any integer between 1 and 6, or wherein —NR$^{23}$R$^{24}$ together with N be a 5-6-membered heterocyclic ring,
V is selected from the group consisting of oxy, sulfanediyl, —CH$_2$—, or —NR$^{22}$—,
R$^{14}$ is selected from the group consisting of —H, —OH, —(C$_1$-C$_6$)-alkyl, —(C$_1$-C$_{10}$)-alkoxy, —(C$_2$-C$_{10}$)-alkenyloxy, -halogen, -azido, —O-allyl, —O-alkinyl, and —NH$_2$
R$^{22}$ is independently selected from the group of —H and —(C$_1$-C$_{10}$)-alkyl,
R$^{23}$ and R$^{24}$ are independently selected from the group consisting of —(C$_1$-C$_{10}$)-alkyl, —(C$_1$-C$_{20}$)-aryl, —(C$_6$-C$_{14}$)-aryl-(C$_1$-C$_{10}$)-alkyl, —(C$_1$-C$_6$)-alkyl-[NH(CH$_2$)$_c$]$_d$—NR$^{26}$R$^{27}$ and a reporter group,
R$^{25}$ is selected from the group consisting of —H, —OH, -halogen, -amino, —(C$_1$-C$_{18}$)-alkylamino, —COOH, —CONH$_2$ and —COO(C$_1$-C$_4$)-alkyl and a reporter group,
R$^{26}$ and R$^{27}$ are independently selected from the group consisting from —H, —(C$_1$-C$_6$)-alkyl, and —(C$_1$-C$_4$)-alkoxy-(C$_1$-C$_6$)-alkyl and a reporter group,
c is an integer from 2 to 6,
d is an integer from 0 to 6, and
B is a moiety of formula I

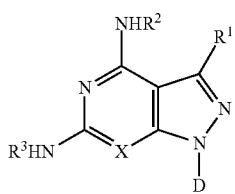

Formula I wherein
R1 is independent from X, R2 or R3 and is selected from the group consisting of
(1) —F, —Cl, —Br or —I,
(2) Nitro
(3) Cyano
(4) —COO—
(5) —(C1-C10)-alkyl substituted according to (10)
(6) —(C2-C10)-alkenyl substituted according to (10)
(7) —(C2-C10)-alkynyl substituted according to (10)
(8) —(C6-C22)-aryl substituted according to (10)
(9) —W—(C1-C10)-alkyl, —W—(C2-C10)-alkenyl, —W—(C2-C10)-alkynyl, —W—(C6-C22)-aryl or W—H, wherein W=—S—, —O—, —NH—, —S—S—, —CO—, —COR—, —CO—NH—, —NH—CO—, —NH—CO—NH—, —NH—CS—NH—, —(CH2)n-[O—(CH2)r]s-, where r and s are, independently of each other, an integer between 1 to 18 and n is 0 or 1 independently from r and s,
(10) substituents (5) to (9) wherein any alkyl, alkenyl, alkynyl or aryl can be substituted by one or more moieties selected from the group consisting of -halogen, —SH, —NO2, —CN, —S—(C1-C6)-alkyl, —NR5R6, —N+R5R6R12, —OR12, —COR11, —NH—CO—NR5R6, —NH—CS—NR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12, OR12, and —SR12
wherein R5, R6 and R12 are selected independently from the group consisting of —H, —(C1-C10)-alkyl, —(C2-C10)-alkenyl, —(C2-C10)-alkinyl, —(C6-C22)-aryl and a reporter group, a group which facilitates intracellular uptake or a group that, when the nucleic acid binding compound hybridizes to its complementary nucleic acid, attacks the latter while binding, cross-linking or cleaving,
said alkyl, alkenyl, alkynyl or aryl in substituents (5) to (10) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
with the proviso that R5, R6 or R12 is not a reporter group if the radicals (5) to (7) are substituted by —NR5R6, NHR12, OR12, or SR12;
R2, R3 is independent from X, R1, R2 and R3 and is selected from the group of,
(1) —H
(2) (C1-C10)-alkyl,
(3) (C2-C10)-alkenyl,
(4) (C2-C10)-alkynyl,
(5) (C6-C22)-aryl,
(6) —Z—(C1-C10)-alkyl, —Z—(C2-C10)-alkenyl, —Z—(C2-C10)-alkynyl, —Z—(C6-C22)-aryl or Z—H, wherein Z=—CO—, —CO—NH—, —CS—NH—, —(CH2)n-[O—(CH2)r]s-, where r and s are, independently of each other, an integer between 1 to 18 and n is 1 or 2 independently from r and s,
(7) substituents (2) to (6)
wherein any alkyl, alkenyl, alkynyl or aryl can be substituted by one or more moieties selected from the group consisting of -halogen, —NO2, —OR12, —CN, —SH, —S—(C1-C6)-alkyl, —NR5R6, —N+R5R6R12, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12 and OR12,
wherein R5, R6 and R12 are selected independently from the group consisting of —H, —(C1-C10)-alkyl, —(C2-C10)-alkenyl, —(C2-C10)-alkynyl, —(C6-C22)-aryl and a reporter group,
said alkyl, alkenyl, alkynyl or aryl in substituents (2) to (7) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-

NR5R6, r and s are independently of each other an integer of from 1 to 18 and n is 0 or 1 independently from r and s;

X is independent from $R^1$, $R^2$ or $R^3$ and is selected from the group consisting of N and CH; and D is the position of attachment of the group to the rest of the nucleic acid binding compound or any salts thereof.

The preferred definitions of the groups as defined under formula I apply to formula II and the following formulae, if not indicated otherwise.

Preferably, in compounds of formula II, $R^{14}$ is hydrogen. Preferred definition of L is oxy. Preferred definition of U is —OH and —O-reporter group. Preferred definition of V is oxy. Preferred definition of c is an integer from 2 to 4, and of d an integer from 0 to 2. Compounds of formula II are especially suited to contain the heterocyclic moiety of the invention as an integrated part (preferably not at one of the termini) of the nucleic acid binding compound. The group $NR^{23}R^{24}$ is preferably selected from the group consisting of dialkylamino groups. In case of this group together with the forming of 5- or 6-membered heterocyclic ring, it assumes preferably the definition of morpholinyl, pyrrolidinyl or piperidinyl.

In a further preferred embodiment, the sugar configuration is selected from the group consisting of the α-D-, β-D-, α-L- and β-L-configurations, most preferred the compound contains at least one 2'-deoxy-β-D-erythro-pentofuranosyl moiety or one β-D-ribofuranosyl moiety. In a preferred embodiment of the invention, D is the glycosid C-1 of a sugar moiety of the compound according to the invention.

In another embodiment of the invention the sugar is in a locked conformation. LNA (Locked Nucleic Acid) is a novel class of nucleic acid analogue. LNA oligomers obey the Watson-Crick base pairing rules and hybridize to complementary oligonucleotides. However, when compared to DNA and other nucleic acid derivatives, LNA provides vastly improved hybridization performance. LNA/DNA or LNA/RNA duplexes are much more thermally stable than the similar duplexes formed by DNA or RNA. In fact, LNA has the highest affinity towards complementary DNA and RNA ever to be reported. In general, the thermal stability of a LNA/DNA duplex is increased 3° C. to 8° C. per modified base in the oligo. Within the fields of general molecular biology and molecular diagnostics, five major fields for the application of LNA have been identified which are capture probes, sample preparation, detection of SNP's (Single Nucleotide Polymorphisms), allele specific PCR, and hybridization probes, Molecular Beacons, Padlock probes, Taqman probes (WO92/02638 and corresponding U.S. Pat. Nos. 5,210,015, 5,804, 375, 5,487,972) and probes for in-situ hybridizations. In most respects, LNA may be handled like DNA. LNA is at least as stable as DNA and is soluble in aqueous buffers. LNA can be ethanol precipitated, dried and resuspended, and can be analyzed on gels, HPLC and MALDI-TOF. LNAs are novel nucleic acid analogs that can dramatically increase the performance of not only diagnostic assays that probe and evaluate genetic information but also of antisense and other genetic medicine approaches. These analogs, which can be utilized in most applications just like their natural counterparts, lock the nucleic acid into the most productive conformation for hybridization. Hybridization, or complementary docking of genetic probes, is the predominant form of evaluation of genetic information in diagnostics. A broad variety of applications for LNA have been developed including a number of extremely sensitive and specific assays able to detect specific disease-causing single base mutations in an individual's genes In the detection of SNPs (Single Nucleotide Polymorphisms), which are the small variations in our genes, that may cause a predisposition to disease, there are data to show that LNA capture probes of only eight nucleotides in length are able to more effectively discriminate between mutated and wildtype genes in a sample than much longer conventional nucleic acid capture probes. Therefore the invention also contemplates compounds according to the invention wherein e.g. at least one atom of the sugar moiety e.g. a carbon or an oxygen atom is connected to at least one other atom of the sugar moiety via at least one bridging moiety containing at least one atom whereby a conformationally constrained sugar is formed as outlined above. Thereby the sugar is fixed in a locked conformation.

For the synthesis of the compounds according to the invention, the reader is referred to Chemistry of Nucleosides and Nucleotides Part 1, edited by L. B. Townsend, Plenum Press New York (1988), Chapter 2: Synthesis and Properties of Purine Nucleosides and Nucleotides, page 113-281 or to U.S. Pat. No. 5,594,121. However, more information is provided below.

Different chemical structures can be used in the backbone of the nucleic acid binding compound. The expert skilled in the field appreciates the fact that the nucleic acid binding compound may also possess a modified 3'-end. Therefore, a preferred subject of the invention is a nucleic acid binding compound as outlined above, wherein the backbone comprises one or more moieties of the general formula III, wherein t is 0 or 1, Formula III

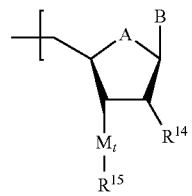

wherein in the case that t=1

A is selected from the group consisting of O, S, $CH_2$ and N—($C_1$-$C_6$)-alkyl, M is selected from the group consisting of oxy, sulfanediyl, —$NR^{22}$—, —($C_1$-$C_{10}$)-alkyl-, or —O—($C_1$-$C_{10}$)-alkyl-O—, and —S—($C_1$-$C_{10}$)-alkyl-O— and —$NR^{22}$—($C_1$-$C_6$)-alkyl-O—, $R^{22}$ is selected from the group of —H, —($C_1$-$C_{10}$)-alkyl, a protecting group and a reporter group, $R^{14}$ is selected from the group consisting of —H, —OH, —($C_1$-$C_3$)-alkyl, —($C_1$-$C_6$)-allyl, —($C_1$-$C_{10}$)-alkoxy, —($C_2$-$C_{10}$)-alkenyloxy, —($C_2$-$C_{10}$)-alkynyloxy, —(O—$CH_2$)$_n$— wherein n may be an integer of from 1 to 18, -halogen, -azido, SH, —($C_1$-$C_{10}$)-alkylmercapto, O-reporter group, O-solid phase and —$NH_2$, $R^{15}$ is selected from the group consisting of —H, —($C_1$-$C_6$)-alkyl, —($C_2$-$C_{10}$)-alkenyl, —($C_2$-$C_{10}$)-alkynyl, —($C_2$-$C_{10}$)-alkyl-carbonyl, —($C_3$-$C_{19}$)-alkenyl-carbonyl, —($C_3$-$C_{19}$)-alkynyl-carbonyl, —($C_6$-$C_{14}$)-aryl-($C_1$-$C_{10}$)-alkyl, a solid phase and a group of formula IV Formula IV

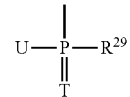

wherein
T is selected from the group consisting of oxo, thioxo and selenoxo, and
U is selected from the group consisting of —OH, O⁻, —O-reporter group, —SH, —SeH, —($C_1$-$C_{10}$)-alkoxy, —($C_1$-$C_{10}$)-alkyl, —($C_6$-$C_{22}$)-aryl, —($C_6$-$C_{14}$)-aryl-($C_1$-$C_{10}$)-alkyl, —NR$^{23}$R$^{24}$, and —(O—($C_1$-$C_{10}$-alkyl-)-R$^{25}$, wherein N can be any integer between 1 and 6, or wherein NR$^{23}$R$^{24}$ can together with N be a 5-6-membered heterocyclic ring,
R$^{23}$ and R$^{24}$ are independently selected from the group consisting of —($C_1$-$C_{10}$)-alkyl, —($C_1$-$C_{20}$-aryl, —($C_6$-$C_{14}$)-aryl-($C_1$-$C_{10}$)-alkyl, —($C_1$-$C_6$)-alkyl-[NH(CH$_2$)$_c$]$_d$—NR$^{26}$R$^{27}$,
R$^{25}$ is selected from the group consisting of —H, —OH, -halogen, -amino, —($C_1$-$C_{18}$)-alkylamino, —COOH, —CONH$_2$ and —COO($C_1$-$C_4$)-alkyl,
R$^{26}$ and R$^{27}$ are independently selected from the group consisting from —H, —($C_1$-$C_6$)-alkyl, and —($C_1$-$C_4$)-alkoxy-($C_1$-$C_6$)-alkyl
R$^{29}$ is selected from the group consisting of —OR$^{30}$ and —SR$^{30}$,
R$^{30}$ is selected from the group consisting of —H, —($C_1$-$C_{10}$)-alkyl, —($C_2$-$C_{10}$)-alkenyl, —($C_6$-$C_{22}$)-aryl, a protecting group, a solid phase and a reporter group
c is an integer from 2 to 6,
d is an integer from 0 to 6, and
B is a moiety of formula I

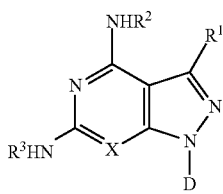

Formula I wherein
R1 is independent from X, R2 or R3 and is selected from the group consisting of
(1) —F, —Cl, —Br or —I,
(2) Nitro
(3) Cyano
(4) —COO—
(5) —(C1-C10)-alkyl substituted according to (10)
(6) —(C2-C10)-alkenyl substituted according to (10)
(7) —(C2-C10)-alkynyl substituted according to (10)
(8) —(C6-C22)-aryl substituted according to (10)
(9) —W—(C1-C10)-alkyl, —W—(C2-C10)-alkenyl, —W—(C2-C10)-alkynyl, —W—(C6-C22)-aryl or W—H, wherein W=—S—, —O—, —NH—, —S—S—, —CO—, —COO—, —CO—NH—, —NH—CO—, —NH—CO—NH—, —NH—CS—NH—, —(CH2)n-[O—(CH2)r]s-, where r and s are, independently of each other, an integer between 1 to 18 and n is 0 or 1 independently from r and s,
(10) substituents (5) to (9) wherein any alkyl, alkenyl, alkynyl or aryl can be substituted by one or more moieties selected from the group consisting of -halogen, —SH, —NO2, —CN, —S—(C1-C6)-alkyl, —NR5R6, —N+R5R6R12, —OR12, —COR11, —NH—CO—NR5R6, —NH—CS—NR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12, OR12, and —SR12
wherein R5, R6 and R12 are selected independently from the group consisting of —H, —(C1-C10)-alkyl, —(C2-C10)-alkenyl, —(C2-C10)-alkinyl, —(C6-C22)-aryl and a reporter group, a group which facilitates intracellular uptake or a group that, when the nucleic acid binding compound hybridizes to its complementary nucleic acid, attacks the latter while binding, cross-linking or cleaving,
said alkyl, alkenyl, alkynyl or aryl in substituents (5) to (10) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
with the proviso that R5, R6 or R12 is not a reporter group if the radicals (5) to (7) are substituted by —NR5R6, NHR12, OR12, or SR12;
R2, R3 is independent from X, R1, R2 and R3 and is selected from the group of,
(1) —H
(2) (C1-C10)-alkyl,
(3) (C2-C10)-alkenyl,
(4) (C2-C10)-alkynyl,
(5) (C6-C22)-aryl,
(6) —Z—(C1-C10)-alkyl, —Z—(C2-C10)-alkenyl, —Z—(C2-C10)-alkynyl, —Z—(C6-C22)-aryl or Z—H, wherein Z=—CO—, —CO—NH—, —CS—NH—, —(CH2)n-[O—(CH2)r]s-, where r and s are, independently of each other, an integer between 1 to 18 and n is 1 or 2 independently from r and s,
(7) substituents (2) to (6)
wherein any alkyl, alkenyl, alkynyl or aryl can be substituted by one or more moieties selected from the group consisting of -halogen, —NO2, —OR12, —CN, —SH, —S—(C1-C6)-alkyl, —NR5R6, —N+R5R6R12, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12 and OR12,
wherein R5, R6 and R12 are selected independently from the group consisting of —H, —(C1-C10)-alkyl, —(C2-C10)-alkenyl, —(C2-C10)-alkynyl, —(C6-C22)-aryl and a reporter group,
said alkyl, alkenyl, alkynyl or aryl in substituents (2) to (7) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s;
X is independent from R1, R2 or R3 and is selected from the group consisting of N and CH; and
D is the position of attachment of the group to the rest of the nucleic acid binding compound
and wherein in the case that t=0, R$^{15}$ is —H,
or any salts thereof.

For the definitions and particulars apply as outlined for the substituents under formulae I and II, if not specified otherwise specifically for formula III. In a preferred embodiment the 3'-end possesses a 2',3'-didesoxyribose, i.e. wherein t=0, $R^{15}$ is —H and $R^{14}$ is —H, or an analogue thereof. This is of interest if an enzymatic termination is necessary when the nucleic acid binding compound according to the invention is extended with triphosphate compounds also occurring in nature as the triphosphates of adenosine, guanosine, uridin, cytidine or thymidine or the desoxyderivates of the triphosphates of adenosine, guanosine, cytidine or thymidine. However, the invention also relates to the extension of primers containing only nucleotides occurring in nature or nucleic acid binding compounds according to the invention with triphosphate compounds according to the invention with the general formula VIII.

Nucleic acid binding compounds, wherein the group of formula I is attached to subunits, for example the nucleotide, at the 3'-terminus of the compound, are useful either as starting compound for the synthesis of longer compounds or/and as end-labeled probes. This group of compounds is especially preferred because the terminal position of probes generally is the most tolerant in view of attachment of chemical moieties.

In view of the modifications to the 3'-end of the nucleic acid binding compound, it is evident that also the 5'-end of the nucleic acid binding compound may be modified. Therefore, another preferred subject of the invention is a nucleic acid binding compound as outlined above comprising a backbone moiety of the formula V

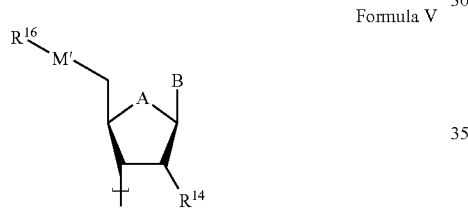

Formula V wherein
A is selected from the group consisting of O, S, $CH_2$ and N—$(C_1-C_6)$-alkyl,
M' is selected from the group consisting of oxy, sulfanediyl, —$NR^{22}$—, —$(C_1-C_{10})$-alkyl, or —O—$(C_1-C_{10})$-alkyl-O—, and —S—$(C_1-C_{10})$-alkyl-O— and —$NR^{22}$—$(C_1-C_6)$-alkyl-O—,
$R^{22}$ is selected from the group of —H, a protecting group, a reporter group and —$(C_1-C_{10})$-alkyl,
$R^{14}$ is selected from the group consisting of —H, —OH, —$(C_1-C_{10})$-alkoxy, —$(C_2-C_{10})$-alkenyloxy, —$(C_2-C_{10})$-alkynyloxy, -halogen, azido, —SH, —S—$(C_1-C_6)$-alkylmercapto, O-reporter group, O-solid phase and $NH_2$,
$R^{16}$ is selected from the group consisting of —H, —$(C_1-C_8)$-alkyl, —$(C_2-C_{18})$-alkenyl, —$(C_2-C_{18})$-alkenyl, —$(C_2-C_{18})$-alkyl-carbonyl, —$(C_3-C_{19})$-alkenyl-carbonyl, —$(C_3-C_{19})$-alkynyl-arbonyl, —$(C_6-C_{14})$-aryl-$(C_1-C_8)$-alkyl, a protective group or a compound of formula IV
wherein

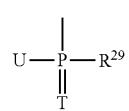

Formula IV

T is selected from the group consisting of oxo, thioxo and selenoxo,
U is selected from the group consisting of —OH, —SH, —SeH, —$(C_1-C_{10})$-alkoxy, —$(C_1-C_{10})$-alkyl, —$(C_6-C_{22})$-aryl, —$(C_6-C_{14})$-aryl-$(C_1-C_{10})$-alkyl, —$NR^{23}R^{24}$ and —(—O—$(C_1-C_{10})$-alkyl-)-$R^{25}$, wherein n can be any integer between 1 and 6, wherein $NR^{23}R^{24}$ can together with N be a 5-6-membered heterocyclic ring,
$R^{23}$ and $R^{24}$ are independently selected from the group consisting of —$(C_1-C_{10})$-alkyl, —$(C_1-C_{20})$-aryl, —$(C_6-C_{14})$-aryl-$(C_1-C_{10})$-alkyl, —$(C_1-C_6)$-alkyl-[NH$(CH_2)_c]_d$—$NR^{26}R^{27}$,
$R^{25}$ is selected from the group consisting of —H, —OH, -halogen, -amino, —$(C_1-C_{18})$-alkylamino, —COOH, —$CONH_2$ and —COO$(C_1-C_4)$-alkyl,
$R^{26}$ and $R^{27}$ are independently selected from the group consisting from —H, —$(C_1-C_6)$-alkyl, and —$(C_1-C_4)$-alkoxy-$(C_1-C_6)$-alkyl
$R^{29}$ is selected from the group consisting of —$OR^{30}$ and —$SR^{36}$,
$R^{30}$ is selected from the group consisting of —H, —$(C_1-C_{10})$-alkyl, —$(C_2-C_{10})$-alkenyl, —$(C_6-C_{22})$-aryl, a protecting group, a solid phase and a reporter group, and
c is an integer from 2 to 6,
d is an integer from 0 to 6, and
B is a moiety of formula I

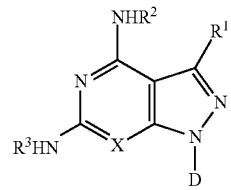

Formula I wherein
R1 is independent from X, R2 or R3 and is selected from the group consisting of
(1) —F, —Cl, —Br or —I,
(2) Nitro
(3) Cyano
(4) —COO—
(5) —(C1-C10)-alkyl substituted according to (10)
(6) —(C2-C10)-alkenyl substituted according to (10)
(7) —(C2-C10)-alkynyl substituted according to (10)
(8) —(C6-C22)-aryl substituted according to (10)
(9) —W—(C1-C10)-alkyl, —W—(C2-C10)-alkenyl, —W—(C2-C10)-alkynyl, —W—(C6-C22)-aryl or W—H, wherein W=—S—, —O—, —NH—, —S—S—, —CO—, —COO—, —CO—NH—, —NH—CO—, —NH—CO—NH—, —NH—CS—NH—, —(CH2)n-[O—(CH2)r]s-, where r and s are, independently of each other, an integer between 1 to 18 and n is 0 or 1 independently from r and s,
(10) substituents (5) to (9) wherein any alkyl, alkenyl, alkynyl or aryl can be substituted by one or more moieties selected from the group consisting of -halogen, —SH, —NO2, —CN, —S—(C1-C6)-alkyl, —NR5R6, —N+R5R6R12, —OR12, —COR11, —NH—CO—NR5R6, —NH—CS—NR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12, OR12, and —SR12 wherein R5, R6 and R12 are selected independently from the group consisting of —H, —(C1-C10)-alkyl, —(C2-C10)-alkenyl, —(C2-C10)-alkinyl, —(C6-C22)-aryl and a reporter group, a group which facilitates intracellular uptake or a group that, when the nucleic acid binding compound hybridizes to its complementary nucleic acid, attacks the latter while binding, cross-linking or cleaving, said alkyl, alkenyl, alkynyl or aryl in substituents (5) to (10) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s, with the proviso that R5, R6 or R12 is not a reporter group if the radicals (5) to (7) are substituted by —NR5R6, NHR12, OR12, or SR12;

R2, R3 is independent from X, R1, R2 and R3 and is selected from the group of,
(1) —H
(2) (C1-C10)-alkyl,
(3) (C2-C10)-alkenyl,
(4) (C2-C10)-alkynyl,
(5) (C6-C22)-aryl,
(6) —Z—(C1-C10)-alkyl, —Z—(C2-C10)-alkenyl, —Z—(C2-C10)-alkynyl, —Z—(C6-C22)-aryl or Z—H, wherein Z=—CO—, —CO—NH—, —CS—NH—, —(CH2)n-[O—(CH2)r]s-, where r and s are, independently of each other, an integer between 1 to 18 and n is 1 or 2 independently from r and s,
(7) substituents (2) to (6)
wherein any alkyl, alkenyl, alkynyl or aryl can be substituted by one or more moieties selected from the group consisting of -halogen, —NO2, —OR12, —CN, —SH, —S—(C1-C6)-alkyl, —NR5R6, —N+R5R6R12, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12 and OR12,
wherein R5, R6 and R12 are selected independently from the group consisting of —H, —(C1-C10)-alkyl, —(C2-C10)-alkenyl, —(C2-C10)-alkynyl, —(C6-C22)-aryl and a reporter group,
said alkyl, alkenyl, alkynyl or aryl in substituents (2) to (7) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s;

X is independent from $R^1$, $R^2$ or $R^3$ and is selected from the group consisting of N and CH; and D is the position of attachment of the group to the rest of the nucleic acid binding compound and any salts thereof.

A very preferred compound is a compound of formula V, wherein M' is O, $R^{16}$ is H and $R^{14}$ is selected from the group consisting of hydrogen and hydroxyl.

Those compounds can for example be used as 5'-terminally labeled probes. Regarding the definitions of the substituents, the definitions as given above apply if not indicated otherwise.

The backbone of the nucleic acid binding compound has the function to bear the base pairing heterocycles such that the compound can bind to a nucleic acid having a complementary sequence. Preferably, the degree of complementarity in the naturally occurring bases will be in the range from 70% up to 100% in a stretch of bases in a region effecting binding, compared to the stretch of same length in the region of the nucleic acid to be bound. Deletions and insertions of subunits in each sequence will therefor, in this calculation, be counted as gaps until the next fitting base and thus reduce complementarity by as many bases as the gap contains.

Preferred backbone contains sugar-phosphate moieties. From these, deoxy sugar containing backbones are further preferred.

Each moiety in the backbone bearing a moiety capable of base pairing to a nucleic acid of complementary sequence, including the moieties of the invention, are termed a subunit. Compounds are known that have backbones mixed of different kinds of subunits. Recently, a new kind of non-natural nucleic acid binding compounds was described. They are termed Peptide Nucleic Acids (PNA), as they contain at least one peptide bond between the subunits (WO 92/20702). The nucleic acid binding compound of the present invention can have any length. However, due to the convenience of chemical synthesis, compounds of a length of less than 100, more preferably from 10 to 30 subunits, for example nucleosides, are preferred.

Altering the thermal stability ($T_m$) of a duplex formed between a nucleic acid binding compound according to the invention, e.g. used as a probe, and a second nucleic acid binding compound using the heterocyclic groups according to the invention and other analogues allows for optimization of duplex stability and mismatch discrimination (see e.g. Kwok, Shirley; Chang, Sheng Yung; Sninsky, John J.; Wang, Alice. A guide to the design and use of mismatched and degenerate primers. PCR Methods Appl. (1994), 3(4), 39-47). One useful aspect of altering the $T_m$, arises from the fact that Adenine-Thymine (A-T) duplexes have a lower $T_m$, than Guanine-Cytosine (G-C) duplexes, due in part to the fact that the A-T duplexes have 2 hydrogen bonds per base-pair, while the G-C duplexes have 3 hydrogen bonds per base pair. For example in heterogeneous oligonucleotide arrays, in which there is a non-uniform distribution of bases, it can be difficult to optimize hybridization conditions for all probes simultaneously. Thus, in some embodiments, it is desirable to destabilize G-C-rich duplexes and/or to increase the stability of A-T-rich duplexes while maintaining the sequence specificity of hybridization. This results in a harmonization or equalization of the contribution of each base pair to the melting temperature of a duplex. This is accomplished, e.g. by replacing one or more of the heterocyclic groups in the nucleic acid binding compound used as a probe (or as the target nucleic acid) with certain modified, non-standard bases. Therefore, in another embodiment, the invention relates to nucleic acid binding compounds according to the invention wherein the nucleic acid binding compounds in addition to a heterocyclic group of formula I further contain a heterocyclic group different from the group of the general formula I, i.e. at least one other heterocyclic group. Substitution of guanine residues with 7-deazaguanine, for example, will generally destabilize duplexes, whereas substituting adenine residues with 2,6-diaminopurine will enhance duplex stability. A variety of other modified bases are also incorporated into nucleic acids to enhance or decrease overall duplex stability while maintaining specificity of hybridization. The incorporation of 6-aza-pyrimidine analogs into oligonucleotide probes generally decreases their binding affinity for complementary nucleic acids. Many 5-substituted pyrimidines substantially increase the stability of hybrids in which they have been substituted in place of the native pyrimidines in the sequence. Examples include 5-bromo-, 5-methyl-, 5-propynyl-, 5-(imidazol-2-yl)- and 5-(thiazol-2-yl)-derivatives of cytosine and uracil. Preferably the additional heterocyclic group is a pyrrolo-[2,3-d]-pyrimidine or a pyrazolo[3,4-d]-pyrimidine or an analogue thereof, in particular the said analogues of adenine or guanine. It should be emphasized that the invention also relates to the case where all other heterocyclic groups are those occurring in nature as adenine, guanine, uracil, cytosin or thymin. Many modified nucleosides, nucleotides and various bases suitable for incorporation into nucleosides are commercially available from a variety of manufacturers, including the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill. Methods of attaching bases to sugar moieties to form nucleosides are known. See, e.g., Lukevics and Zablocka (1991), Nucleoside Synthesis: Organosilicon Methods Ellis Horwood Limited Chichester, West Sussex, England and the references therein. Methods of phosphorylating nucleosides to form nucleotides, and of incorporating nucleotides into oligonucleotides are also known. See, e.g., Agrawal (ed) (1993) Protocols for Oligonucleotides and Analogues, Synthesis and Properties, Methods in Molecular Biology volume 20, Humana Press, Towota, N.J., and the references therein. See also, Crooke and Lebleu, and Sanghvi and Cook, and the references cited therein, both supra.

In yet another embodiment, the invention relates to nucleic acid binding compounds according to the invention wherein the nucleic acid binding compound according to the invention further contains at the 3'-end in addition to a heterocyclic group of formula I a heterocyclic group different from the group of the general formula I, i.e. at least one other heterocyclic group. Preferably, the nucleic acid binding compound according to the invention additionally comprises a heterocyclic group which is a pyrrolo-[2,3-d]-pyrimidine or a pyrazolo[3,4-d]-pyrimidine or an analogue thereof, preferably the said analogues of guanine or adenine.

The invention further contemplates the binding product of a nucleic acid binding compound according to the invention and a second nucleic acid binding compound, the nucleic acid binding compound according to the invention and the second nucleic acid binding compound being bound to each other by base pairing in parallel or antiparallel orientation. In addition to heterocyclic groups with formula I with substituents as defined above, the nucleic acid binding compound according to the invention may contain other natural nucleobase or nucleobases not occurring in nature as e.g. nucleobases with heterocyclic groups according to the invention, heterocyclic groups as pyrrolo-[2,3-d]-pyrimidine or pyrazolo[3,4-d]-pyrimidine or analogues thereof, preferably the said analogues of guanine or adenine or 7-deaza-guanine. Further non-natural heterocyclic groups are known to the person skilled in the art.

Another embodiment of the invention is a nucleic acid binding compound wherein the heterocyclic group of formula I as defined above is incorporated to compensate for a decrease of the melting point created by the attachment of the reporter groups, preferably 1 to 5 nucleotides separated from the nucleotide to which a reporter group is attached. This is because a reporter group leads to disturbations of the hybridization efficiency of a nucleic acid binding compound close to the point or nucleotide whereto the reporter group is attached.

Another embodiment of the invention is a nucleic acid binding compound wherein the heterocyclic group of formula I as defined above is incorporated to compensate for a decrease of the melting point created by mismatches discrimination. This problem has been discussed by Kwok, Shirley; Chang, Sheng Yung; Sninsky, John J.; Wang, Alice. A guide to the design and use of mismatched and degenerate primers. PCR Methods Appl. (1994), 3(4), 39-47. This is particularly useful for the amplification of viral subtypes where the hybridization stretch does not contain complementary bases over the total length of the stretch.

In an embodiment, the invention relates to nucleic acid binding compounds according to the invention wherein a protecting group substitutes one or two hydrogen atoms of a —OH, —SH, —NH$_2$, —NH-alkyl, —NH-alkenylene, —NH— alkynylene, or a NH-aryl group, although it is preferred that the nucleic acid binding compounds according to the invention only contain a few protecting groups or even none.

One particular preferred embodiment, is the use of the nucleic acid binding compounds in field of arrays of nucleic acid binding compounds bound to a solid surface (see e.g. U.S. Pat. No. 5,143,854, U.S. Pat. No. 6,022,963, U.S. Pat. No. 6,156,501, WO90/15070, WO 92/10092), which has the properties as described in these references and can be manufactured as described therein or by Niemeyer and Blohm (Angew. Chem. Int. Ed. 1999, 38, 2865-2869). Therefore, in a preferred embodiment, the invention relates to a composition for analyzing interactions between nucleic acid binding compounds whereby one nucleic acid binding compound is a target nucleic acid. The composition comprises an array of a plurality of nucleic acid binding compounds having different sequences, wherein said plurality of nucleic acid binding compounds are coupled to a solid substrate at known locations and are selected to bind to complementary nucleic acid binding compounds or target nucleic acids whereby only the nucleic acid binding compounds or the nucleic acid binding compounds and the complementary nucleic acid binding compounds (or target nucleic acids) together are nucleic acid binding compounds comprising a backbone, said backbone having attached heterocyclic groups capable of base pairing to nucleobases, wherein a heterocyclic group is a substituted pyrazolo[3,4-d]pyrimidine or an analogue thereof. Different kinds of supports are possible as e.g. nonporous supports or other solid supports less porous than typical peptide synthesis supports; however, for certain applications of the invention, quite porous beads, resins, or other supports work well and are often preferable. One such support is a resin in the form of beads. In general, the bead size is in the range of 1 nm to 100 μm, but a more massive solid support of up to 1 mm in size may sometimes be used. Particularly preferred resins include Sasrin resin (a polystyrene resin available from Bachem Bioscience, Switzerland); and TentaGel S AC, TentaGel PHB, or TentaGel S NH$_2$ resin (polystyrene-polyethylene glycol copolymer resins available from Rappe Polymere, Tubingen, Germany). Other preferred supports are commercially available and described by Novabiochem, La Jolla, Calif. In other embodiments, the solid substrate is flat, or alternatively, may take on alternative surface configurations. For example, the solid substrate may contain raised or depressed regions on which synthesis takes place or is coated with porous SiO$_2$/ glass. In some embodiments, the solid substrate will be chosen to provide appropriate light-absorbing characteristics. For example, the substrate may be a polymerized Langmuir Blodgett film, functionalized glass, Si, Ge, GaAs, GaP, $SiO_2$, $SiN_4$, modified silicon, or any one of a variety of gels or polymers such as (poly)tetrafluorethylene, (poly)vinylidendifluoride, polystyrene, polycarbonate, or combinations thereof. Other suitable solid substrate material will be readily apparent to those of skill in the art. Preferably, the surface of the solid substrate will contain reactive groups, which could be carboxyl, amino, hydroxyl, thiol, or the like. More preferably, the surface will be optically transparent and will have surface Si—OH functionalities, such as are found on silica surfaces. Particularly preferred is therefore a composition, wherein the solid substrate is selected from the group consisting of silica, polymeric materials, glass, porous glass, beads, chips, and slides.

Preferred is a composition according to the invention wherein only the nucleic acid binding compounds or the nucleic acid binding compounds and the complementary nucleic acid binding compounds (or target nucleic acid) are nucleic acid binding compounds according to the invention, i.e. they contain a heterocyclic group with formula I as described above. The complementary nucleic acid binding compounds (or target nucleic acid) may contain a heterocyclic group according to formula I as described above when they are amplified with e.g. the polymerase chain reaction in the presence of a triphosphate according to the invention containing a heterocyclic group of formula I as described above.

Preferred is a composition according to the invention, wherein the nucleic acid binding compounds comprise a backbone, said backbone having attached heterocyclic groups capable of base pairing to nucleobases characterized in that a heterocyclic groups is a substituted pyrazolo[3,4-d]pyrimidine or an analogue thereof. In a preferred embodiment the substituted pyrazolo[3,4-d]pyrimidine or an analogue thereof is a substituted 7-deaza-8-aza-2,6-diamino-purine or a derivative thereof or a 7-substituted 7-deaza-8-aza-2,6-diamino-purine or a derivative thereof. In another embodiment of the invention the substituted pyrazolo[3,4-d]pyrimidine analogue is a substituted pyrazolo[3,4-d]pyrimidine analogue of adenine or guanine or a 7-substituted pyrazolo[3,4-d]pyrimidine analogue of adenine or guanine, wherein the adenine or guanine analogues may preferably carry the same substituents $R^1$ in the 7-position or N-substituents $R^2$ and $R^3$ as set out directly below for the substituted 7-deaza-8-aza-2,6-diamino-purine or a derivative thereof or a 7-substituted 7-deaza-8-aza-2,6-diamino-purine or a derivative thereof.

In a very preferred embodiment of the invention the substituted 7-deaza-8-aza-2,6-diamino-purine or a derivative thereof or the 7-substituted 7-deaza-8-aza-2,6-diamino-purine or a derivative thereof has the general formula I

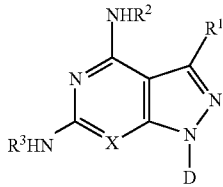

Formula I

R1 is independent from X, R2 or R3 and is selected from the group consisting of
(1) —F, —Cl, —Br or —I,
(2) Nitro
(3) Cyano
(4) —COO—
(5) —(C1-C10)-alkyl substituted according to (10)
(6) —(C2-C10)-alkenyl substituted according to (10)
(7) —(C2-C10)-alkynyl substituted according to (10)
(8) —(C6-C22)-aryl substituted according to (10)
(9) —W—(C1-C10)-alkyl, —W—(C2-C10)-alkenyl, —W—(C2-C10)-alkynyl, —W—(C6-C22)-aryl or W—H, wherein W=—S—, —O—, —NH—, —S—S—, —CO—, —COO—, —CO—NH—, —NH—CO—, —NH—CO—NH—, —NH—CS—NH—, —(CH2)n—[O—(CH2)r]s-, where r and s are, independently of each other, an integer between 1 to 18 and n is 0 or 1 independently from r and s,
(10) substituents (5) to (9) wherein any alkyl, alkenyl, alkynyl or aryl can be substituted by one or more moieties selected from the group consisting of -halogen, —SH, —NO2, —CN, —S—(C1-C6)-alkyl, —NR5R6, —N+R5R6R12, —OR12, —COR11, —NH—CO—NR5R6, —NH—CS—NR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12, OR12, and —SR12
wherein R5, R6 and R12 are selected independently from the group consisting of —H, —(C1-C10)-alkyl, —(C2-C10)-alkenyl, —(C2-C10)-alkinyl, —(C6-C22)-aryl and a reporter group, a group which facilitates intracellular uptake or a group that, when the nucleic acid binding compound hybridizes to its complementary nucleic acid, attacks the latter while binding, cross-linking or cleaving,
said alkyl, alkenyl, alkynyl or aryl in substituents (5) to (10) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
with the proviso that R5, R6 or R12 is not a reporter group if the radicals (5) to (7) are substituted by —NR5R6, NHR12, OR12, or SR12;
R2, R3 is independent from X, R1, R2 and R3 and is selected from the group of,
(1) —H
(2) (C1-C10)-alkyl,
(3) (C2-C10)-alkenyl,
(4) (C2-C10)-alkynyl,
(5) (C6-C22)-aryl,
(6) —Z—(C1-C10)-alkyl, —Z—(C2-C10)-alkenyl, —Z—(C2-C10)-alkynyl, —Z—(C6-C22)-aryl or Z—H, wherein Z=—CO—, —CO—NH—, —CS—NH—, —(CH2)n-[O—(CH2)r]s-, where r and s are, independently of each other, an integer between 1 to 18 and n is 1 or 2 independently from r and s,
(7) substituents (2) to (6)
wherein any alkyl, alkenyl, alkynyl or aryl can be substituted by one or more moieties selected from the group consisting of -halogen, —NO2, —OR12, —CN, —SH, —S—(C1-C6)-alkyl, —NR5R6, —N+R5R6R12, —COR11, —NH—CONR5R6, —NH—CSNR5R6 and —(CH2)n-[O—(CH2)r]s-NR5R6, r and s are independently of each other an integer wherein R11 is selected from the group consisting of —NHR12 and OR12, wherein R5, R6 and R12 are selected independently from the group consisting of —H, —(C1-C10)-alkyl, —(C2-C10)-alkenyl, —(C2-C10)-alkynyl, —(C6-C22)-aryl and a reporter group, said alkyl, alkenyl, alkynyl or aryl in substituents (2) to (7) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR$^5$R$^6$, r and s are independently of each other an integer of from 1 to 18 and n is 0 or 1 independently from r and s;

X is independent from R$^1$, R$^2$ or R$^3$ and is selected from the group consisting of N and CH D is the position of attachment of the group to the rest of the nucleic acid binding compound.

In a very preferred embodiment, the nucleic acid binding compound is a nucleic acid binding compound according to the invention, preferably R$^1$=Br or R$^1$=I. Further preferred is a composition which comprises an array of nucleic acid binding compounds 5 to 20 nucleotides in length.

The invention is further related to a binding product of a first nucleic acid binding compound according to the invention or a composition according to the invention with a second nucleic acid binding compound or a second a nucleic acid binding compound according to the invention, wherein the first nucleic acid binding compound or the composition and the second nucleic acid binding compound being bound to each other by base pairing in parallel or antiparallel orientation.

The invention is further related to methods for the synthesis of the nucleic acid binding compounds according to the invention and to compounds useful in these methods. The nucleic acid binding compound of the present invention can be prepared in solution or, preferably, on a solid phase, where appropriate using an automatic synthesis device. The oligomers can be assembled stepwise by successively condensing a mononucleotide, which in each case possesses a nucleotide base, onto an appropriately derivatized support or onto a growing oligomer chain. Alternatively, the nucleic acid binding compounds can be assembled by joining dinucleotides or trinucleotides together [S. Beaucage et al., Tetrahedron, 48 (12), 2223-2311, (1992); and Tetrahedron, 48 (28), 6123-6194, (1993)]. This is particularly advantageous when synthesizing oligonucleotides which posses modified phosphate bridges.

The oligonucleotides are assembled using methods which are known to the person skilled in the art, such as the triester method, the H-phosphonate method or the phosphoramidite method [E. Sonveaux, (1986), Bioorganic Chemistry, 14, 274-325; S. L. Beaucage et al., (1992), Tetrahedron, 48, 2223-2311].

The compounds according to the present invention can be advantageously used in oligonucleotide synthesis as the ammonia hydrolysis of the protecting groups of the pyrazolo [3,4-d]pyrimidine nucleosides is quicker than the slow ammonia hydrolysis of 2-amino-adenosine which takes several days.

A further subject of the invention is therefore a method for the chemical synthesis of nucleic acid binding compounds of the present invention using activated subunits, wherein said subunit contains a group of formula I. The most preferred method of chemical synthesis uses the phosphoramidite approach. A particularly preferred method uses a activated subunit one or more compounds of general formula VII. This method has the advantage that it is very convenient and the reagents necessary, for example a phosphoramidite containing a group of formula I, are possible to be included easily.

A further subject of the invention are therefore compounds of the general formula VII

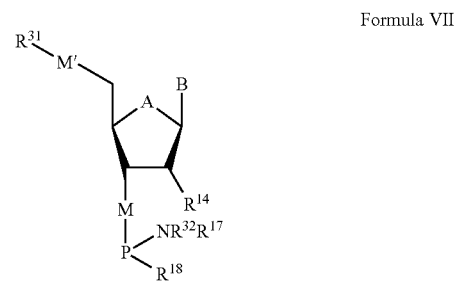

Formula VII wherein

A is selected from the group consisting of O, S, CH$_2$ and N—(C$_1$-C$_6$)-alkyl, M and M' are independently selected from the group consisting of oxy, sulfanediyl, —NR$^{22}$, —C$_1$-C$_{10}$-alkyl, or —O—(C$_1$-C$_{10}$)-alkyl-O—, and —S—(C$_1$-C$_{10}$)-alkyl-O— and —NR$^{22}$—(C$_1$-C$_6$)-alkyl-O—, R$^{22}$ is selected from the group of —H and —(C$_1$-C$_{10}$)-alkyl, R$^{14}$ is selected from the group consisting of —H, —OR$^{31}$, —(C$_1$-C$_{10}$)-alkoxy, —(C$_2$-C$_{10}$)-alkenyloxy, —(C$_2$-C$_{10}$)-alkynyloxy, -halogen, -azido, NHR$^{31}$, SR$^{31}$, R$^{31}$ is a protecting group or a reporter group, R$^{32}$ and R$^{17}$ are independently selected from the group consisting of —H, alkyl, —(C$_2$-C$_{10}$)-alkenyl, —(C$_6$-C$_{22}$)-aryl, or wherein NR$^{32}$R$^{17}$ can form together with N a 5-6-membered heterocyclic ring, R$^{18}$ is selected from the group consisting of —(C$_2$-C$_6$)-alkenyloxy, substituted or unsubstituted —(C$_1$-C$_6$)-alkyl, unsubstituted —(C$_1$-C$_6$)-alkoxy or —(C$_1$-C$_6$)-alkoxy substituted one or more times by a group selected from the group consisting of -halogen, p-nitroaryloxy and -cyano, and B is a group of formula I

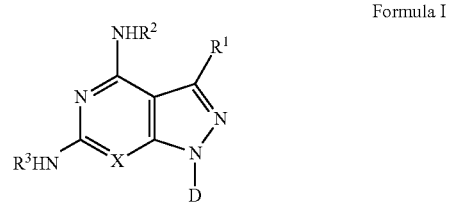

Formula I

R1 is independent from X, R2 or R3 and is selected from the group consisting of (1) —F, —Cl, —Br or —I,
(2) Nitro
(3) Cyano
(4) —COO—
(5) —(C1-C10)-alkyl substituted according to (10)
(6) —(C2-C10)-alkenyl substituted according to (10)
(7) —(C2-C10)-alkynyl substituted according to (10)

(8) —(C6-C22)-aryl substituted according to (10)
(9) —W—(C1-C10)-alkyl, —W—(C2-C10)-alkenyl, —W—(C2-C10)-alkynyl, —W—(C6-C22)-aryl or W—H, wherein W=—S—, —O—, —NH—, —S—S—, —CO—, —COO—, —CO—NH—, —NH—CO—, —NH—CO—NH—, —NH—CS—NH—, —(CH2)n-[O—(CH2)r]s-, where r and s are, independently of each other, an integer between 1 to 18 and n is 0 or 1 independently from r and s,
(10) substituents (5) to (9) wherein any alkyl, alkenyl, alkynyl or aryl can be substituted by one or more moieties selected from the group consisting of -halogen, —SH, —NO2, —CN, —S—(C1-C6)-alkyl, —NR5R6, —N+R5R6R12, —OR12, —COR11, —NH—CO—NR5R6, —NH—CS—NR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12, OR12, and —SR12
wherein R5, R6 and R12 are selected independently from the group consisting of —H, —(C1-C10)-alkyl, —(C2-C10)-alkenyl, —(C2-C10)-alkinyl, —(C6-C22)-aryl and a reporter group, a group which facilitates intracellular uptake or a group that, when the nucleic acid binding compound hybridizes to its complementary nucleic acid, attacks the latter while binding, cross-linking or cleaving,
(11)

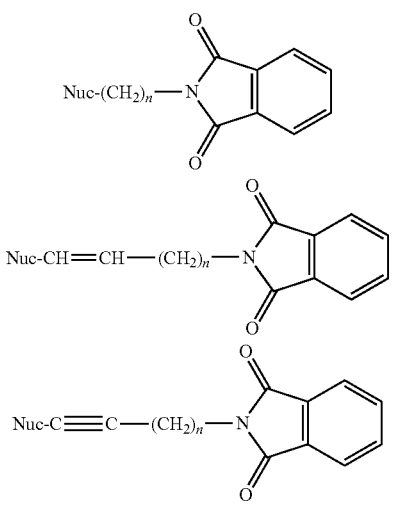

wherein Nuc is the link to formula I and n is any integer from 1 to 18 said alkyl, alkenyl, alkynyl or aryl in substituents (5) to (10) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
with the proviso that R5, R6 or R12 is not a reporter group if the radicals (5) to (7) are substituted by —NR5R6, NHR12, OR12, or SR12;

said alkyl, alkenyl, alkynyl or aryl in substituents (5) to (10) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
with the proviso that R5, R6 or R12 is not a reporter group if the radicals (5) to (7) are substituted by —NR5R6, NHR12, OR12, or SR12;
R2, R3 is independent from X, R1, R2 and R3 and is selected from the group of,
(1) —H
(2) (C1-C10)-alkyl,
(3) (C2-C10)-alkenyl,
(4) (C2-C10)-alkynyl,
(5) (C6-C22)-aryl,
(6) —Z—(C1-C10)-alkyl, —Z—(C2-C10)-alkenyl, —Z—(C2-C10)-alkynyl, —Z—(C6-C22)-aryl or Z—H, wherein Z=—CO—, —CO—NH—, —CS—NH—, —(CH2)n-[O—(CH2)r]s-, where r and s are, independently of each other, an integer between 1 to 18 and n is 1 or 2 independently from r and s,
(7) substituents (2) to (6)
wherein any alkyl, alkenyl, alkynyl or aryl can be substituted by one or more moieties selected from the group consisting of -halogen, —NO2, —OR12, —CN, —SH, —S—(C1-C6)-alkyl, —NR5R6, —N+R5R6R12, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12 and OR12,
wherein R5, R6 and R12 are selected independently from the group consisting of —H, —(C1-C10)-alkyl, —(C2-C10)-alkenyl, —(C2-C10)-alkynyl, —(C6-C22)-aryl and a reporter group,
said alkyl, alkenyl, alkynyl or aryl in substituents (2) to (7) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR$^5$R$^6$, r and s are independently of each other an integer of from 1 to 18 and n is 0 or 1 independently from r and s;
X is independent from R$^1$, R$^2$ or R$^3$ and is selected from the group consisting of N and CH
D is the position of attachment of the group to the rest of the nucleic acid binding compound.
with the proviso that one or two hydrogen atoms of any —OH, —SH, —NH$_2$, —NH-alkyl, —NH— alkenylene, —NH— alkynylene, or —NH-aryl group are substituted by a protecting group, and any salts thereof.

After suitable protective groups for the amino groups at position 2 and 6 and for the free 5'-hydroxyl group of the sugar moiety have been introduced, the monomers are converted into the corresponding phosphonate or phosphoramidite derivatives. Suitable amino protective groups, for example in the form of acyl protective groups (e.g. isobutyryl, acetyl or phenoxyacetyl), are inserted using well-known methods [J. C. Schulhof, D. Molko, R. Teoule, (1987), Nucleic Acids Res., 15, 397-416]. An example of a suitable protective group for the free 5'-OH group of the sugar is the 4,4'-dimethoxytrityl residue, whose insertion is likewise effected using known methods [C. B. Reese (1978), Tetrahedron, 34, 3143; D. Flockerzi et al., (1981), Liebigs Ann. Chem., 1568]. The monomers which have been protected in this way can be converted into the corresponding phosphonates in accordance with a protocol due to Froehler et al. [B. C. Froehler et al., (1986), Nucleic Acids Res., 14, 5399]. Cyanoethyl-phosphoramidite derivatives can, for example, be prepared by reacting the monomers with chloro-□-cyanoethoxy-(N,N-diisopropylamino)phosphane in anhydrous dichlormethane [N. D. Sinha et al., (1984), Nucleic Acids Res., 12, 4539].

Further subject of the invention are compounds of the general formula IX

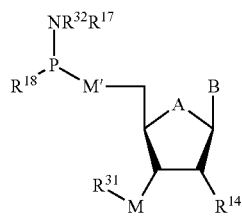

Formula IX wherein
- A is selected from the group consisting of O, S, $CH_2$ and N—$(C_1-C_6)$-alkyl,
- M and M' are independently selected from the group consisting of oxy, sulfanediyl, —$NR^{22}$, —$(C_1-C_{10})$-alkyl, or —O—$(C_1-C_{10})$-alkyl-O—, and —S—$(C_1-C_{10})$-alkyl-O— and —$NR^{22}$—$(C_1-C_6)$-alkyl-O—,
- $R^{22}$ is selected from the group of —H and —$(C_1-C_{10})$-alkyl,
- $R^{14}$ is selected from the group consisting of —H, —$OR^{31}$, —$(C_1-C_{10})$-alkoxy, —$(C_2-C_{10})$-alkenyloxy, —$(C_2-C_{10})$-alkynyloxy, -halogen, -azido, $NHR^{31}$, $SR^{31}$, or O-reporter group,
- $R^{31}$ is a protecting group or a reporter group,
- $R^{32}$ and $R^{17}$ are independently selected from the group consisting of —H, —$(C_1-C_{10})$-alkyl, —$(C_2-C_{10})$-alkenyl, —$(C_6-C_{22})$-aryl, or wherein $NR^{32}R^{17}$ can form together with N a 5-6-membered heterocyclic ring,
- $R^{18}$ is selected from the group consisting of —$(C_2-C_6)$-alkenyloxy, substituted or unsubstituted —$(C_1-C_6)$-alkyl, unsubstituted —$(C_1-C_6)$-alkoxy or —$(C_1-C_6)$-alkoxy substituted one or more times by a group selected from the group consisting of -halogen, p-nitroaryloxy and -cyano, and
- B is a group of formula I

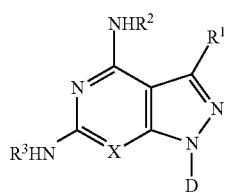

Formula I

R1 is independent from X, R2 or R3 and is selected from the group consisting of
(1) —F, —Cl, —Br or —I,
(2) Nitro
(3) Cyano
(4) —COO—
(5) —(C1-C10)-alkyl substituted according to (10)
(6) —(C2-C10)-alkenyl substituted according to (10)
(7) —(C2-C10)-alkynyl substituted according to (10)
(8) —(C6-C22)-aryl substituted according to (10)
(9) —W—(C1-C10)-alkyl, —W—(C2-C10)-alkenyl, —W—(C2-C10)-alkynyl, —W—(C6-C22)-aryl or W—H, wherein W=—S—, —O—, —NH—, —S—S—, —CO—, —COO—, —CO—NH—, —NH—CO—, —NH—CO—NH—, —NH—CS—NH—, —(CH2)n-[O—(CH2)r]s-, where r and s are, independently of each other, an integer between 1 to 18 and n is 0 or 1 independently from r and s,
(10) substituents (5) to (9) wherein any alkyl, alkenyl, alkynyl or aryl can be substituted by one or more moieties selected from the group consisting of -halogen, —SH, —NO2, —CN, —S—(C1-C6)-alkyl, —NR5R6, —N+R5R6R12, —OR12, —COR11, —NH—CO—NR5R6, —NH—CS—NR5R6 and —(CH2)$_n$-[O—-(CH2)r]s-NR5R6, r and s are independently of each other an integer of from 1 to 18 and n is 0 or 1 independently from r and s,
wherein R11 is selected from the group consisting of —NHR12, OR12, and —SR12
wherein R5, R6 and R12 are selected independently from the group consisting of —H, —$(C_1-C_{10})$-alkyl, —$(C_2-C_{10})$-alkenyl, —(C2-C10)-alkinyl, —(C6-C22)-aryl and a reporter group, a group which facilitates intracellular uptake or a group that, when the nucleic acid binding compound hybridizes to its complementary nucleic acid, attacks the latter while binding, cross-linking or cleaving, (11)

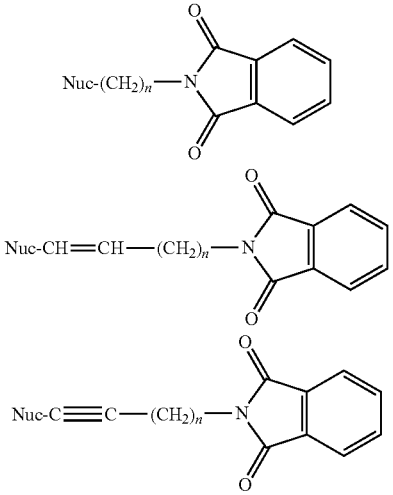

wherein Nuc is the link to formula I and n is any integer from 1 to 18 said alkyl, alkenyl, alkynyl or aryl in substituents (5) to (10) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
with the proviso that R5, R6 or R12 is not a reporter group if the radicals (5) to (7) are substituted by —NR5R6, NHR12, OR12, or SR12;

R2, R3 is independent from X, R1, R2 and R3 and is selected from the group of,
(1) —H
(2) (C1-C10)-alkyl,
(3) (C2-C10)-alkenyl,
(4) (C2-C10)-alkynyl,
(5) (C6-C22)-aryl,
(6) —Z—(C1-C10)-alkyl, —Z—(C2-C10)-alkenyl, —Z—(C2-C10)-alkynyl, —Z—(C6-C22)-aryl or Z—H, wherein Z=—CO—, —CO—NH—, —CS—NH—, —(CH2)n-[O—(CH2)r]s-, where r and s are, independently of each other, an integer between 1 to 18 and n is 1 or 2 independently from r and s,
(7) substituents (2) to (6)
wherein any alkyl, alkenyl, alkynyl or aryl can be substituted by one or more moieties selected from the group consisting of -halogen, —NO2, —OR12, —CN, —SH, —S—(C1-C6)-alkyl, —NR5R6, —N+R5R6R12, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12 and OR12,
wherein R5, R6 and R12 are selected independently from the group consisting of —H, —(C1-C10)-alkyl, —(C2-C10)-alkenyl, —(C2-C10)-alkynyl, —(C6-C22)-aryl and a reporter group,
said alkyl, alkenyl, alkynyl or aryl in substituents (2) to (7) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR$^5$R$^6$, r and s are independently of each other an integer of from 1 to 18 and n is 0 or 1 independently from r and s;
X is independent from R$^1$, R$^2$ or R$^3$ and is selected from the group consisting of N and CH
D is the position of attachment of the group to the rest of the nucleic acid binding compound.
with the proviso that one or two hydrogen atoms of any —OH, —SH, —NH$_2$, —NH-alkyl, —NH-alkenylene, —NH— alkynylene, or —NH-aryl group are substituted by a protecting group, and any salts thereof.
Those compounds can be used like those of formula VII in chemical synthesis.
A further subject of the invention are compounds of the general formula X wherein

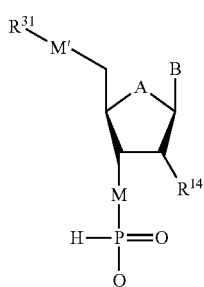

Formula X

M and M' are independently selected from the group consisting of oxy, sulfanediyl, —NR$^{22}$, —(C$_1$-C$_{10}$)-alkyl, or —O—(C$_1$-C$_{10}$)-alkyl-O—, and —S—(C$_1$-C$_{10}$)-alkyl-O— and —NR$^{22}$—(C$_1$-C$_6$)-alkyl-O—,
R$^{22}$ is selected from the group of —H and —(C$_1$-C$_{10}$)-alkyl,
R$^{14}$ is selected from the group consisting of —H, —OR$^{31}$, (C$_1$-C$_{10}$)-alkoxy, —(C$_2$-C$_{10}$)-alkenyloxy, —(C$_2$-C$_{10}$)-alkynyloxy, -halogen, -azido, NHR$^{31}$, SR$^{31}$, or O-reporter,
R$^{31}$ is a protecting group or a reporter group,

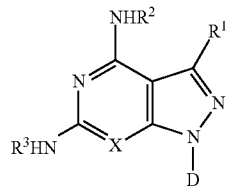

Formula I

R1 is independent from X, R2 or R3 and is selected from the group consisting of
(1) —F, —Cl, —Br or —I,
(2) Nitro
(3) Cyano
(4) —COO—
(5) —(C1-C10)-alkyl substituted according to (10)
(6) —(C2-C10)-alkenyl substituted according to (10)
(7) —(C2-C10)-alkynyl substituted according to (10)
(8) —(C6-C22)-aryl substituted according to (10)
(9) —W—(C1-C10)-alkyl, —W—(C2-C10)-alkenyl, —W—(C2-C10)-alkynyl, —W—(C6-C22)-aryl or W—H, wherein W=—S—, —O—, —NH—, —S—S—, —CO—, —COO—, —CO—NH—, —NH—CO—, —NH—CO—NH—, —NH—CS—NH—, —(CH2)n-[O—(CH2)r]s-, where r and s are, independently of each other, an integer between 1 to 18 and n is 0 or 1 independently from r and s,
(10) substituents (5) to (9) wherein any alkyl, alkenyl, alkynyl or aryl can be substituted by one or more moieties selected from the group consisting of -halogen, —SH, —NO2, —CN, —S—(C1-C6)-alkyl, —NR5R6, —N+R5R6R12, —OR12, —COR11, —NH—CO—NR5R6, —NH—CS—NR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12, OR12, and —SR12
wherein R5, R6 and R12 are selected independently from the group consisting of —H, —(C1-C10)-alkyl, —(C2-C10)-alkenyl, —(C2-C10)-alkinyl, —(C6-C22)-aryl and a reporter group, a group which facilitates intracellular uptake or a group that, when the nucleic acid binding compound hybridizes to its complementary nucleic acid, attacks the latter while binding, cross-linking or cleaving, (11)

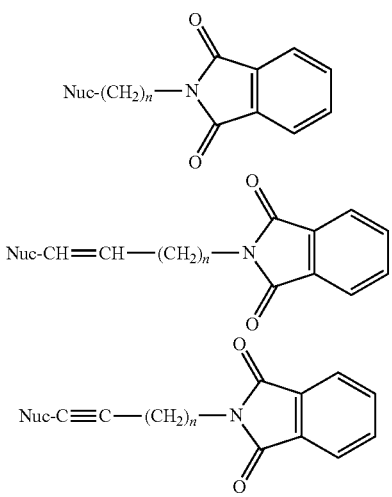

wherein Nuc is the link to formula I and n is any integer from 1 to 18 said alkyl, alkenyl, alkynyl or aryl in substituents (5) to (10) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s, with the proviso that R5, R6 or R12 is not a reporter group if the radicals (5) to (7) are substituted by —NR5R6, NHR12, OR12, or SR12;

R2, R3 is independent from X, R1, R2 and R3 and is selected from the group of, (1) —H
(2) (C1-C10)-alkyl,
(3) (C2-C10)-alkenyl,
(4) (C2-C10)-alkenyl,
(5) (C6-C22)-aryl,
(6) —Z—(C1-C10)-alkyl, —Z—(C2-C10)-alkenyl, —Z—(C2-C10)-alkynyl, —Z—(C6-C22)-aryl or Z—H, wherein Z=—CO—, —CO—NH—, —CS—NH—, —(CH2)n-[O—(CH2)r]s-, where r and s are, independently of each other, an integer between 1 to 18 and n is 1 or 2 independently from r and s,
(7) substituents (2) to (6)
wherein any alkyl, alkenyl, alkynyl or aryl can be substituted by one or more moieties selected from the group consisting of -halogen, —NO2, —OR12, —CN, —SH, —S—(C1-C6)-alkyl, —NR5R6, —N+R5R6R12, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12 and OR12,
wherein R5, R6 and R12 are selected independently from the group consisting of —H, —(C1-C10)-alkyl, —(C2-C10)-alkenyl, —(C2-C10)-alkynyl, —(C6-C22)-aryl and a reporter group, said alkyl, alkenyl, alkynyl or aryl in substituents (2) to (7) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR$^5$R$^6$, r and s are independently of each other an integer of from 1 to 18 and n is 0 or 1 independently from r and s;

X is independent from R$^2$ or R$^3$ and is selected from the group consisting of N and CH D is the position of attachment of the group to the rest of the nucleic acid binding compound.

with the proviso that one or two hydrogen atoms of any —OH, —SH, —NH$_2$, —NH-alkyl, —NH-alkenylene, —NH— alkynylene, or —NH-aryl group are substituted by a protecting group, and any salts thereof. Those compounds are useful in chemical synthesis of nucleic acid binding compounds as mentioned above and the precursors thereof.

In another option which is more suited for long oligomers and those based on natural backbones, the oligomers are produced enzymatically. In this case, a starting oligomer is reacted with a polymerase and a triphosphate or modified triphosphate such that a monophosphate or a modified monophosphate is attached to a terminus of the oligomer, thus elongating the oligomer. Also for this method, the man skilled in the art will know several possible formates, like the nick-translation approach, or the simple primer extension (J. Sambrook. E. F. Fritsch, T. Maniatis, Molecular Cloning—A laboratory Manual, Cold Spring Harbor Laboratory Press 1989).

A further subject of the invention is therefore a method for the enzymatic synthesis of a nucleic acid binding compound according to the invention comprising reacting a triphosphate subunit with a primer using a nucleic acid as a template for the elongation of the primer, wherein the triphosphate subunit contains a heterocyclic group of formula I. Preferably, the triphosphate subunit has the formula VI. For example, 7- or 8-substituted 7-deaza-2'-deoxyadenosine and guanosine-triphosphates can be easily incorporated enzymatically into DNA by various DNA polymerases (WO 00/68422).

A further subject of the present invention are therefore compounds of the general formula VI

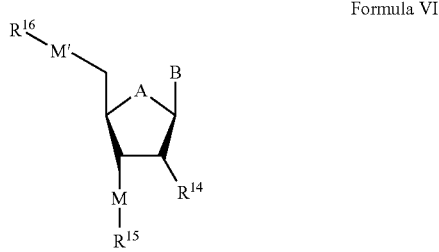

Formula VI wherein

A is selected from the group consisting of O, S, CH$_2$ and N—(C$_1$-C$_6$)-alkyl, M and M' are independently selected from the group consisting of oxy, sulfanediyl, —NR$^{22}$—, —(C$_1$-C$_{10}$)-alkyl-, or —O—(C$_1$-C$_{10}$)-alkyl-O—, and —S—(C$_1$-C$_{10}$)-alkyl-O— and —NR$^{22}$—(C$_1$-C$_6$)-alkyl-O—, R$^{22}$ is selected from the group of —H, —(C$_1$-C$_{10}$)-alkyl, a protecting group and a reporter group, R$^{14}$ is selected from the group consisting of —H, —OR$^{31}$, —(C$_1$-C$_{10}$)-alkoxy, O-protecting group, S-protecting group, NH$_2$-protecting group, —(C$_2$-C$_{10}$)— alkenyloxy, —(C$_2$-C$_{10}$)-alkynyloxy, -halogen, -azido, SH, —(C$_1$-C$_{10}$-alkylmercapto, and —O-solid phase, R$^{15}$ and R$^{16}$ are independently selected from the group consisting of —H, —(C$_1$-C$_6$)-alkyl, —(C$_2$-C$_{10}$)-alkenyl, —(C$_2$-C$_{10}$)-alkynyl, —(C$_2$-C$_{10}$)-alkyl-carbonyl, —(C$_3$-C$_{19}$)-alkenyl-carbonyl, —(C$_3$-C$_{19}$)-alkynyl-carbonyl, —(C$_6$-C$_{14}$)-aryl-(C$_1$-C$_{10}$)-alkyl, protecting group and a solid phase B is the link to a moiety of formula I,

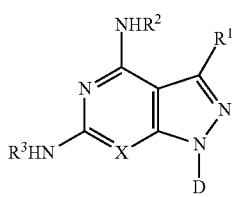

Formula I

R1 is independent from X, R2 or R3 and is selected from the group consisting of (1) —F, —Cl, —Br or —I, (2) Nitro (3) Cyano (4) —COO—

(5) —(C1-C10)-alkyl substituted according to (10)

(6) —(C2-C10)-alkenyl substituted according to (10)

(7) —(C2-C10)-alkynyl substituted according to (10)

(8) —(C6-C22)-aryl substituted according to (10)

(9) —W—(C1-C10)-alkyl, —W—(C2-C10)-alkenyl, —W—(C2-C10)-alkynyl, —W—(C6-C22)-aryl or W—H, wherein W=—S—, —O—, —NH—, —S—S—, —CO—, —COO—, —CO—NH—, —NH—CO—, —NH—CO—NH—, —NH—CS—NH—, —(CH2)n-[O—(CH2)r]s-, where r and s are, independently of each other, an integer between 1 to 18 and n is 0 or 1 independently from r and s,

(10) substituents (5) to (9) wherein any alkyl, alkenyl, alkynyl or aryl can be substituted by one or more moieties selected from the group consisting of -halogen, —SH, —NO2, —CN, —S—(C1-C6)-alkyl, —NR5R6, —N+R5R6R12, —OR12, —COR11, —NH—CO—NR5R6, —NH—CS—NR5R6 and —(CH2)n—[O—(CH2)r]s-NR5R6, r and s are independently of each other an integer of from 1 to 18 and n is 0 or 1 independently from r and s, wherein R11 is selected from the group consisting of —NHR12, OR12, and —SR12 wherein R5, R6 and R12 are selected independently from the group consisting of —H, —(C1-C10)-alkyl, —(C2-C10)-alkenyl, —(C2-C10)-alkynyl, —(C6-C22)-aryl and a reporter group, a group which facilitates intracellular uptake or a group that, when the nucleic acid binding compound hybridizes to its complementary nucleic acid, attacks the latter while binding, cross-linking or cleaving, (11)

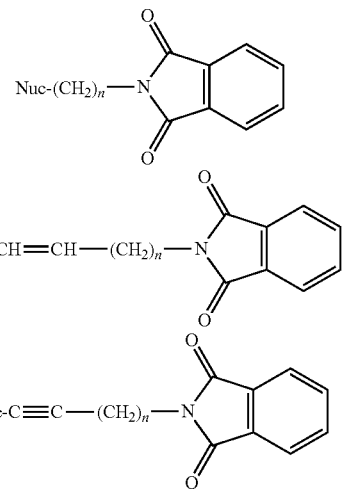

wherein Nuc is the link to formula I and n is any integer from 1 to 18 said alkyl, alkenyl, alkynyl or aryl in substituents (5) to (10) being unsubstituted or substituted by one or more moieties selected from the group consisting of -halogen, —SH, —S—(C$_1$-C$_6$)-alkyl, —(C$_1$-C$_6$)-alkoxy, —OH, —NR5R6, —COR11, —NH—CONR5R6, —NH—CSNR5R6 and —(CH2)n—[O—(CH2)r]s-NR5R6, r and s are independently of each other an integer of from 1 to 18 and n is 0 or 1 independently from r and s, with the proviso that R5, R6 or R12 is not a reporter group if the radicals (5) to (7) are substituted by —NR5R6, NHR12, OR12, or SR12;

R2, R3 is independent from X, R1, R2 and R3 and is selected from the group of, (1) —H (2) (C1-C10)-alkyl, (3) (C2-C$_{10}$)-alkenyl, (4) (C2-C10)-alkynyl, (5) (C6-C22)-aryl, (6) —Z—(C1-C10)-alkyl, —Z—(C2-C10)-alkenyl, —Z—(C2-C10)-alkynyl, —Z—(C6-C22)-aryl or Z—H, wherein Z=—CO—, —CO—NH—, —CS—NH—, —(CH2)n-[O—(CH$_2$)$_r$]s where r and s are, independently of each other, an integer between 1 to 18 and n is 1 or 2 independently from r and s, (7) substituents (2) to (6)

wherein any alkyl, alkenyl, alkynyl or aryl can be substituted by one or more moieties selected from the group consisting of -halogen, —NO2, —OR12, —CN, —SH, —S—(C1-C6)-alkyl, —NR5R6, —N+R5R6R12, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s, wherein R11 is selected from the group consisting of —NHR12 and OR12, wherein R5, R6 and R12 are selected independently from the group consisting of —H, —(C1-C10)-alkyl, —(C2-C10)-alkenyl, —(C2-C10)-alkynyl, —(C6-C22)-aryl and a reporter group, said alkyl, alkenyl, alkynyl or aryl in substituents (2) to (7) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(C2)r]s-NR$^5$R$^6$, r and s are independently of each other an integer of from 1 to 18 and n is 0 or 1 independently from r and s;

X is independent from R$^1$, R$^2$ or R$^3$ and is selected from the group consisting of N and CH D is the position of attachment of the group to the rest of the nucleic acid binding compound.

whereby optionally at least one protecting group substitutes one or two hydrogen atoms of a —OH, —SH, NH$_2$, NH-alkyl, —NH-alkenylene, —NH-alkynylene, or a —NH-aryl group, and any salts thereof.

Most preferred in these compounds -M'R$^{16}$ is a triphosphate group and -MR$^{15}$ is OH. The most preferred compound is the one in which R$^{14}$ is —H.

Most preferred compounds for enzymatic synthesis of a nucleic acid binding compound according to the invention are of formula VIII

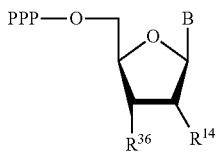

Formula VIII wherein
PPP is a triphosphate group, a thiotriphosphate group or analogues thereof,
R$^{14}$ is selected from the group consisting of —H, —OH, —(C$_1$-C$_{10}$)-alkoxy, —(C$_2$-C$_{10}$)-alkenyloxy, —(C$_2$-C$_{10}$)-alkynyloxy halogen, -azido and NH$_2$,
R$^{36}$ is selected from the group of —H and —OH, and
B is a group of formula I.

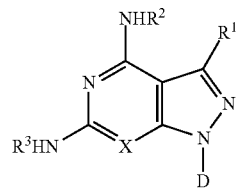

Formula I wherein
R$^1$ is independent from X, R2 or R3 and is selected from the group consisting of
(1) —F, —Cl, —Br or —I,
(2) Nitro
(3) Cyano
(4) —COO—
(5) —(C1-C10)-alkyl substituted according to (10)
(6) —(C2-C10)-alkenyl substituted according to (10)
(7) —(C2-C10)-alkynyl substituted according to (10)
(8) —(C6-C22)-aryl substituted according to (10)
(9) —W—(C1-C10)-alkyl, —W—(C2-C10)-alkenyl, —W—(C2-C10)-alkynyl, —W—(C6-C22)-aryl or W—H, wherein W=—S—, —O—, —NH—, —S—S—, —CO—, —COO—, —CO—NH—, —NH—CO—, —NH—CO—NH—, —NH—CS—NH—, —(CH2)n-[O—(CH2)r]s-, where r and s are, independently of each other, an integer between 1 to 18 and n is 0 or 1 independently from r and s,

(10) substituents (5) to (9) wherein any alkyl, alkenyl, alkynyl or aryl can be substituted by one or more moieties selected from the group consisting of -halogen, —SH, —NO2, —CN, —S—(C1-C6)-alkyl, —NR5R6, —N+R5R6R12, —OR12, —COR11, —NH—CO—NR5R6, —NH—CS—NR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12, OR12, and —SR12
wherein R5, R6 and R12 are selected independently from the group consisting of —H, —(C1-C10)-alkyl, —(C2-C10)-alkenyl, —(C2-C10)-alkinyl, —(C6-C22)-aryl and a reporter group, a group which facilitates intracellular uptake or a group that, when the nucleic acid binding compound hybridizes to its complementary nucleic acid, attacks the latter while binding, cross-linking or cleaving,
said alkyl, alkenyl, alkynyl or aryl in substituents (5) to (10) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
with the proviso that R5, R6 or R12 is not a reporter group if the radicals (5) to (7) are substituted by —NR5R6, NHR12, OR12, or SR12;

R2, R3 is independent from X, R1, R2 and R3 and is selected from the group of,
(1) —H
(2) (C1-C10)-alkyl,
(3) (C2-C10)-alkenyl,
(4) (C2-C10)-alkynyl,
(5) (C6-C22)-aryl,
(6) —Z—(C1-C10)-alkyl, —Z—(C2-C10)-alkenyl, —Z—(C2-C10)-alkynyl, —Z—(C6-C22)-aryl or Z—H, wherein Z=—CO—, —CO—NH—, —CS—NH—, —(CH2)n-[O—(CH2)r]s-, where r and s are, independently of each other, an integer between 1 to 18 and n is 1 or 2 independently from r and s,
(7) substituents (2) to (6)
wherein any alkyl, alkenyl, alkynyl or aryl can be substituted by one or more moieties selected from the group consisting of -halogen, —NO2, —OR12, —CN, —SH, —S—(C$_1$-C$_6$)-alkyl, —NR5R6, —N+R5R6R12, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12 and OR12,
wherein R5, R6 and R12 are selected independently from the group consisting of —H, —(C1-C10)-alkyl, —(C2-C10)-alkenyl, —(C2-C10)-alkynyl, —(C6-C22)-aryl and a reporter group,
said alkyl, alkenyl, alkynyl or aryl in substituents (2) to (7) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s;

X is independent from $R^1$, $R^2$ or $R^3$ and is selected from the group consisting of N and CH D is the position of attachment of the group to the rest of the nucleic acid binding compound.

whereby optionally at least one protecting group substitutes one or two hydrogen atoms of a —OH, —SH, $NH_2$, NH-alkyl, —NH-alkenylene, —NH-alkynylene, or a —NH-aryl group, and any salts thereof.

3' deoxy- and 2'-3'-didesoxytriphosphate subunits according to formula VIII for example can be used as terminating nucleotides in sequencing methods.

More preferable, above mentioned method for enzymatic synthesis uses as a triphosphate subunit a compound of formula VIII as defined above.

By the above methods, it is principally possible to introduce only one monomer containing the moiety of the invention into one nucleic acid binding component, but also more than one, as the case may be. This is especially possible using chemical methods for the synthesis of nucleic acid binding compounds.

These nucleic acid compounds according to the invention can be usefully applied in hybridization methods. Therefore, a further subject of the invention is a method for the determination of a nucleic acid comprising the steps of providing a sample suspected to contain said nucleic acid, providing a nucleic acid binding compound, which is essentially complementary to a part or all of said nucleic acid, contacting said sample with said nucleic acid binding compound under conditions for binding said nucleic acid binding compound to said nucleic acid, and determining the degree of hybridization or the binding product formed from said nucleic acid and said nucleic acid binding compound as a measure of the presence of said nucleic acid.

Methods for determination of nucleic acids by hybridization are generally known, for example from Sambrook et al. (cited above). They can easily adopted for the use of probes of the present invention.

Probes of the present invention also allow the determination of pathogens like bacteria or viruses, for example hepatitis A, B or C virus (HBV, HCV), the human immunodeficiency virus (HIV), the human papilloma virus or parvovirus B19. However, any other viruses are possible.

In a preferred embodiment of the invention, a nucleic acid binding compound, hereinafter termed a first nucleic acid binding compound, is used in a hybridization reaction to form a parallel or antiparallel duplex with a second nucleic acid binding compound wherein the first and/or the second nucleic acid binding compound comprise a backbone, said backbone having attached heterocyclic groups capable of base pairing to nucleobases characterized in that a heterocyclic groups, i.e. at least one of said heterocyclic groups, is a substituted pyrazolo[3,4-d]pyrimidine or an analogue thereof. Preferably, the hybridization reaction is a multiplex hybridization reaction, i.e. multiple target nucleic acids as second nucleic acid binding compounds and multiple first nucleic acid binding compounds are present. This is done preferably in the form of an array, i.e. the first nucleic acid binding compound comprises a multitude of different nucleic acid binding compounds with different sequences and is attached in the form of an array to a solid phase on different addressable locations. In a further embodiment, a nucleic acid binding compound is used as a capture probe, whereby the nucleic acid binding compound has a backbone whereto heterocyclic groups capable of base pairing to nucleobases are attached characterized in that a heterocyclic group, i.e. at least one of said heterocyclic groups, is a substituted pyrazolo[3,4-d]pyrimidine or an analogue thereof. Most preferred the nucleic acid binding compound is a nucleic acid binding compound with a heterocyclic group of the formula I and the substituents described therefor. Most preferred are the halogen substituents in the 7-position as e.g. brom and iod.

In another preferred embodiment, the substituted pyrazolo[3,4-d]pyrimidine or the analogue thereof is used in place of a heterocyclic group in a first nucleic acid binding compound to increase the melting temperature of a parallel or antiparallel duplex with a second nucleic acid binding compound whereby the increase in melting temperature is increased in comparison to the melting temperature of a duplex of the first nucleic acid binding compound with the second nucleic acid binding compound wherein the heterocyclic group in the first nucleic acid binding compound is complementary to a heterocyclic group in the second nucleic acid binding compound. Preferably, a natural heterocyclic group as an adenine base is substituted in the first nucleic acid binding compound by the heterocyclic group according to the invention.

In another preferred embodiment, the substituted pyrazolo [3,4-d]pyrimidine or the analogue thereof is used in place of a heterocyclic group in a first nucleic acid binding compound used as a probe in an amplification reaction, to increase the melting temperature of a duplex with a second nucleic acid binding compound in comparison to the melting temperature of a primer used in the amplification reaction, whereby the increase in melting temperature is compared to the melting temperature of a duplex of the first nucleic acid binding compound with the second nucleic acid binding compound wherein the heterocyclic group in the first nucleic acid binding compound is complementary to a heterocyclic group in the second nucleic acid binding compound. Preferably, the amplification reaction is in the TaqMan® format which is described in more detail below. Preferably, a naturally occurring heterocyclic group as an adenine base is substituted by the heterocyclic group according to the invention.

In another embodiment the substituted pyrazolo[3,4-d]pyrimidine or the analogue thereof is used in place of a heterocyclic group in a first nucleic acid binding compound to harmonize the contribution of each base pair to the melting temperature of a parallel or antiparallel duplex with a second nucleic acid binding compound. This is particularly interesting when other non-natural compounds are present which contribute to the melting temperature in the order of the contribution of the heterocyclic group according to the invention. Then it is of interest to use the heterocyclic group according to the invention to equalize (or harmonize) the contribution of each heterocyclic group or base. This has already been described supra. This use is particularly interesting for multiplex reactions and in arrays.

In a further preferred embodiment, the substituted pyrazolo [3,4-d]pyrimidine or the analogue thereof is used in place of a heterocyclic group in a first nucleic acid binding compound for enhanced detection of sequences in a second nucleic acid binding compound having mismatches in a duplex with the first nucleic acid binding compound. Preferably the second nucleic acid binding compound is a target nucleic acid e.g. different subtypes of a virus. The substituted pyrazolo[3,4-d] pyrimidine or the analogue thereof can in principle be positioned anywhere in the nucleic acid binding compound. This use is of particular interest when the second nucleic acid binding compound is a target nucleic acid, in particular a viral target, and different subtypes of a virus have to be amplified and detected. Therefore, in another embodiment of the invention the substituted pyrazolo[3,4-d]pyrimidine or an analogue thereof is used in place of a heterocyclic group in a nucleic acid binding compound for enhanced detection of subtypes in a target nucleic acid.

In another embodiment, the substituted pyrazolo[3,4-d]pyrimidine or an analogue thereof is used in place of a heterocyclic group in a nucleic acid binding compound to increase the melting temperature of an intramolecular duplex or hairpin of the nucleic acid binding compound whereby the increase in melting temperature is compared to the melting temperature of the intramolecular duplex of the nucleic acid binding compound wherein the heterocyclic group in the nucleic acid binding compound is complementary to a heterocyclic group in the hybridizing part of the nucleic acid binding compound. This is particularly interesting in the Molecular beacons, Scorpion and TaqMan technology (WO92/02638 and corresponding U.S. Pat. Nos. 5,210,015, 5,804,375, 5,487,972) when two fluorescent labels have to be brought into close proximity for efficient quenching.

Selecting the length of nucleic acid binding compounds or probes is also an important consideration when optimizing hybridization specificity. In general, shorter probe sequences are more specific than longer ones, in that the occurrence of a single-base mismatch has a greater destabilizing effect on the hybrid duplex. However, as the overall thermodynamic stability of hybrids decreases with length, in some embodiments it is desirable to enhance duplex stability for short probes globally. Therefore, in a further embodiment the substituted pyrazolo[3,4-d]pyrimidine or an analogue thereof is used in place of a heterocyclic group in a nucleic acid binding compound to reduce the length of the nucleic acid binding compound in detection reactions as the heterocyclic group according to the invention has a high contribution to the melting temperature and therefore duplex stability of short probes.

Preferably, in the above described uses, at least one, preferably one or two, reporter groups are attached to the nucleic acid binding compound or a probe. Preferably, the substituted pyrazolo[3,4-d]pyrimidine or the analogue thereof used in place of a heterocyclic group is 1 to 5 nucleotides separated from the point of attachment of one or of all of the reporter groups. Preferably, the substituted pyrazolo[3,4-d]pyrimidine or the analogue thereof is used in place of an adenine in the nucleic acid binding compound.

All uses described above are preferably performed in the form of multiplex hybridization reactions, i.e. multiple target nucleic acids as second nucleic acid binding compounds and multiple first nucleic acid binding compounds are present. This is done preferably in the form of an array, i.e. the first nucleic acid binding compound comprises a multitude of different nucleic acid binding compounds with different sequences and is attached in the form of an array to a solid phase on different addressable locations.

In all the uses of the invention, the substituted pyrazolo[3,4-d]pyrimidine analogue is preferably a substituted pyrazolo[3,4-d]pyrimidine analogue of adenine or guanine or a 7-substituted pyrazolo[3,4-d]pyrimidine analogue of adenine or guanine, wherein the adenine or guanine analogues may preferably carry the same substituents $R^1$ in the 7-position or N-substituents $R^2$ and $R^3$ as set out directly below for the substituted 7-deaza-8-aza-2,6-diamino-purine or a derivative thereof or a 7-substituted 7-deaza-8-aza-2,6-diamino-purine or a derivative thereof. More preferably, the substituted pyrazolo[3,4-d]pyrimidine or an analogue thereof is a substituted 7-deaza-8-aza-2,6-diamino-purine or a derivative thereof or a 7-substituted 7-deaza-8-aza-2,6-diamino-purine or a derivative thereof. Even more preferred, the substituted 7-deaza-8-aza-2,6-diamino-purine or a derivative thereof or the 7-substituted 7-deaza-8-aza-2,6-diamino-purine or a derivative thereof has the formula I with the substituents as defined in the following.

In the uses described above, in the most preferred embodiment the substituted 7-deaza-8-aza-2,6-diamino-purine or a derivative thereof or the 7-substituted 7-deaza-8-aza-2,6-diamino-purine or a derivative thereof has the general formula I

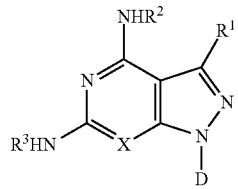

Formula I wherein
R1 is independent from X, R2 or R3 and is selected from the group consisting of
(1) —F, —Cl, —Br or —I,
(2) Nitro
(3) Cyano
(4) —COO—
(5) —(C1-C10)-alkyl substituted according to (10)
(6) —(C2-C10)-alkenyl substituted according to (10)
(7) —(C2-C10)-alkynyl substituted according to (10)
(8) —(C6-C22)-aryl substituted according to (10)
(9) —W—(C1-C10)-alkyl, —W—(C2-C10)-alkenyl, —W—(C2-C10)-alkynyl, —W—(C6-C22)-aryl or W—H, wherein W=—S—, —O—, —NH—, —S—S—, —CO—, —COO—, —CO—NH—, —NH—CO—, —NH—CO—NH—, —NH—CS—NH—, —(CH2)n-[O—(CH2)r]s-, where r and s are, independently of each other, an integer between 1 to 18 and n is 0 or 1 independently from r and s,
(10) substituents (5) to (9) wherein any alkyl, alkenyl, alkynyl or aryl can be substituted by one or more moieties selected from the group consisting of -halogen, —SH, —NO2, —CN, —S—(C1-C6)-alkyl, —NR5R6, —N+R5R6R12, —OR12, —COR11, —NH—CO—NR5R6, —NH—CS—NR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12, OR12, and —SR12
wherein R5, R6 and R12 are selected independently from the group consisting of —H, —(C1-C10)-alkyl, —(C2-C10)-alkenyl, —(C2-C10)-alkinyl, —(C6-C22)-aryl and a reporter group, a group which facilitates intracellular uptake or a group that, when the nucleic acid binding compound hybridizes to its complementary nucleic acid, attacks the latter while binding, cross-linking or cleaving,
said alkyl, alkenyl, alkynyl or aryl in substituents (5) to (10) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-

NR5R6, r and s are independently of each other an integer of from 1 to 18 and n is 0 or 1 independently from r and s, with the proviso that R5, R6 or R12 is not a reporter group if the radicals (5) to (7) are substituted by —NR5R6, NHR12, OR12, or SR12;

R2, R3 is independent from X, R1, R2 and R3 and is selected from the group of,
(1) —H
(2) (C1-C10)-alkyl,
(3) (C2-C10)-alkenyl,
(4) (C2-C10)-alkynyl,
(5) (C6-C22)-aryl,
(6) —Z—(C1-C10)-alkyl, —Z—(C2-C10)-alkenyl, —Z—(C2-C10)-alkynyl, —Z—(C6-C22)-aryl or Z—H, wherein Z=—CO—, —CO—NH—, —CS—NH—, —(CH2)n-[O—(CH2)r]s-, where r and s are, independently of each other, an integer between 1 to 18 and n is 1 or 2 independently from r and s,
(7) substituents (2) to (6)
wherein any alkyl, alkenyl, alkynyl or aryl can be substituted by one or more moieties selected from the group consisting of -halogen, —NO2, —OR12, —CN, —SH, —S—(C1-C6)-alkyl, —NR5R6, —N+R5R6R12, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12 and OR12,
wherein R5, R6 and R12 are selected independently from the group consisting of —H, —(C1-C10)-alkyl, —(C2-C10)-alkenyl, —(C2-C10)-alkynyl, —(C6-C22)-aryl and a reporter group,
said alkyl, alkenyl, alkenyl or aryl in substituents (2) to (7) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s;
X is independent from $R^1$, $R^2$ or $R^3$ and is selected from the group consisting of N and CH; and
D is the position of attachment of the group to the rest of the nucleic acid binding compound
or any salts thereof.

In the most preferred embodiment, the nucleic acid binding compound is a nucleic acid binding compound according to the invention preferably wherein $R^1$=Br or $R^1$=I.

Nucleic acid binding compounds according to the present invention also can be applied in nucleic acid determination methods in the case the nucleic acid to be determined is amplified. Since the original publication of nucleic acid amplification, various primer-based nucleic acid amplification methods have been described including, but are not limited to, Ligase Chain Reaction (LCR, Wu and Wallace, 1989, Genomics 4:560-569 and Barany, 1991, Proc. Natl. Acad. Sci. USA 88:189-193); Polymerase Ligase Chain Reaction (Barany, 1991, PCR Methods and Applic. 1:5-16); Gap-LCR (PCT Patent Publication No. WO 90/01069); Repair Chain Reaction (European Patent Publication No. 439,182 A2), 3SR (Kwoh et al., 1989, Proc. Natl. Acad. Sci. USA 86:1173-1177; Guatelli et al., 1990, Proc. Natl. Acad. Sci. USA 87:1874-1878; PCT Patent Publication No. WO 92/0880A), and NASBA (U.S. Pat. No. 5,130,238). Further, there are strand displacement amplification (SDA), transcription mediated amplification (TMA), and Qβ-amplification (for a review see e.g. Whelen and Persing (1996). Annu. Rev. Microbiol. 50, 349-373; Abramson and Myers, 1993, Current Opinion in Biotechnology 4:41-47). A preferred method is the polymerase chain reaction (PCR). The invention is also related to the amplification of the target nucleic acid in the presence of the triphophates of heterocyclic groups according to the invention as pyrazolo-[3,4-d]-pyrimidines, substituted variants thereof or analogues thereof, particularly preferred are 7-substituted variants thereof. Most preferred are the triphosphates of the heterocylic groups according to formula I with the substituents as defined above.

The nucleic acid binding compounds according to the present invention can be used as primers and probes as e.g. as a capture probe. In the case, that the nucleic acid binding compound should be used as probe, it will preferably contain a detectable reporter group. Any hybrids formed from the nucleic acid binding compound and a nucleic acid can then be determined via the detectable reporter group. This group of assays can further be divided into two groups, one being the group of homogeneous assays and the other being the heterogeneous assays. In heterogeneous assays, preferably the hybrid (binding product) will be determined when bound to a solid phase. This embodiment has the advantage that any excess of probe and other components can be removed easily from the hybrid, thus make the determination easier. The hybrid formed can be captured to a solid phase either covalently, noncovalently, specifically or unspecifically. There are several embodiments which are known to a man skilled in the art.

In the so-called homogeneous assays, the hybrid formed will not be bound to a solid phase, but will be determined either directly or indirectly in solution. A preferred example of such assays is disclosed in PCT/US 91/05571 which is incorporated by reference here.

In particular, when using several nucleic acid binding compounds, for example when conducting PCR-, multiplex-PCR- or multiplex-hybridization-methods it is often difficult to find appropriate hybridization conditions ensuring a good specificity without loosing some specific hybridization complexes resulted from a lower $T_m$, which also means a lower stability. In the case of diagnostic methods this can lead to false negative results, which should be avoided. A further difficulty lies in the complexity of biological samples, for example blood or sputum. Such samples often have background nucleic acids, which may disturb the determination method, for example leading to false positive results.

Therefore the heterocyclic groups of formula I can also be used in multiplex hybridization methods in order to increase the $T_m$ of one or more hybridization complexes formed in an assay. By introducing a heterocyclic group of formula I instead of a natural base contained in a nucleic acid binding compound used in that assay the $T_m$ of the hybridization complex formed with its target nucleic acid can be increased. Such changes of the $T_m$ still allows the specific hybridization of the nucleic acid compound with its target nucleic acid at a different temperature. A preferred application field are multiplex hybridization methods on chips which often use hundreds to thousands hybridization probes.

Also included in the present invention are intermediates and precursor compounds for the chemical synthesis of the described nucleic acid binding compounds. Preferred intermediates and precursor compounds are described below.

Preferred is a solid phase bound precursor for the synthesis of a nucleic acid binding compound comprising a backbone, wherein the backbone comprises a moiety of the general formula VI

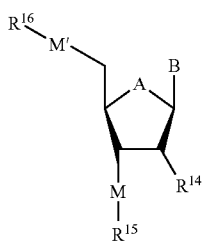

Formula VI wherein
- A is selected from the group consisting of O, S, $CH_2$ and N—$(C_1$-$C_6)$-alkyl,
- M and M' are independently selected from the group consisting of oxy, sulfanediyl, —$NR^{22}$—, —$(C_1$-$C_{10})$-alkyl-, or —O—$(C_1$-$C_{10})$-alkyl-O—, and —S—$(C_1$-$C_{10})$-alkyl-O— and —$NR^{22}$—$(C_1$-$C_6)$-alkyl-O—,
- $R^{22}$ is selected from the group of —H, —$(C_1$-$C_{10})$-alkyl, a protecting group and a reporter group,
- $R^{14}$ is selected from the group consisting of —H, —$OR^{31}$, —$(C_1$-$C_{10})$-alkoxy, O-protecting group, S-protecting group, $NH_2$-protecting group, —$(C_2$-$C_{10})$-alkenyloxy, —$(C_2$-$C_{10})$-alkynyloxy, -halogen, -azido, SH, —$(C_1$-$C_{10})$-alkylmercapto, and —O-solid phase,
- $R^{15}$ and $R^{16}$ are independently selected from the group consisting of —H, —$(C_1$-$C_6)$-alkyl, —$(C_2$-$C_{10})$-alkenyl, —$(C_2$-$C_{10})$-alkynyl, —$(C_2$-$C_{10})$-alkyl-carbonyl, —$(C_3$-$C_{19})$-alkenyl-carbonyl, —$(C_3$-$C_{19})$-alkynyl-carbonyl, —$(C_6$-$C_{14})$-aryl-$(C_1$-$C_{10})$-alkyl, protecting group and a solid phase
- B is the link to a moiety of formula I,

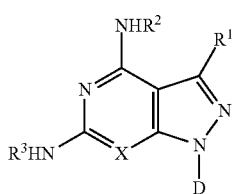

Formula I wherein
- $R^1$ is independent from X, $R^2$ or $R^3$ and is selected from the group consisting of
  (1) —F, —Cl, —Br or —I,
  (2) Nitro
  (3) Cyano
  (4) —COO—
  (5) —(C1-C10)-alkyl substituted according to (10)
  (6) —(C2-C10)-alkenyl substituted according to (10)
  (7) —(C2-C10)-alkynyl substituted according to (10)
  (8) —(C6-C22)-aryl substituted according to (10)
  (9) —W—(C1-C10)-alkyl, —W—(C2-C10)-alkenyl, —W—(C2-C10)-alkynyl, —W—(C6-C22)-aryl or W—H, wherein W=—S—, —O—, —NH—, —S—S—, —CO—, —COO—, —CO—NH—, —NH—CO—, —NH—CO—NH—, —NH—CS—NH—, —(CH2)n-[O—(CH2)r]s-, where r and s are, independently of each other, an integer between 1 to 18 and n is 0 or 1 independently from r and s,
  (10) substituents (5) to (9) wherein any alkyl, alkenyl, alkynyl or aryl can be substituted by one or more moieties selected from the group consisting of -halogen, —SH, —NO2, —CN, —S—(C1-C6)-alkyl, —NR5R6, —N+R5R6R12, —OR12, —COR11, —NH—CO—NR5R6, —NH—CS—NR5R6 and —(CH2)n-[O—(CH2)r]s-NR5R6, r and s are independently of each other an integer of from 1 to 18 and n is 0 or 1 independently from r and s,
    wherein R11 is selected from the group consisting of —NHR12, OR12, and —SR12
    wherein R5, R6 and R12 are selected independently from the group consisting of —H, —(C1-C10)-alkyl, —(C2-C10)-alkenyl, —(C2-C10)-alkinyl, —(C6-C22)-aryl and a reporter group, a group which facilitates intracellular uptake or a group that, when the nucleic acid binding compound hybridizes to its complementary nucleic acid, attacks the latter while binding, cross-linking or cleaving,
  (11)

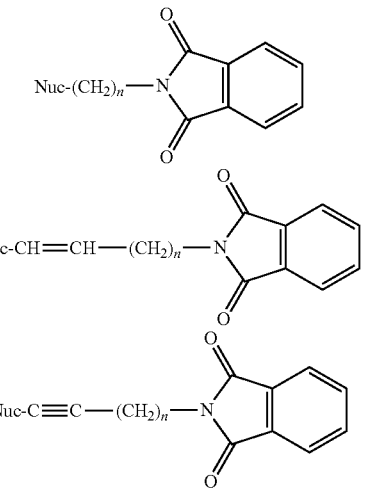

wherein Nuc is the link to formula I and n is any integer from 1 to 18
R2, R3 is independent from X, R1, R2 and R3 and is selected from the group of,
  (1) —H
  (2) (C1-C10)-alkyl,
  (3) (C2-C10)-alkenyl,
  (4) (C2-C10)-alkynyl,
  (5) (C6-C22)-aryl,
  (6) —Z—(C1-C10)-alkyl, —Z—(C2-C10)-alkenyl, —Z—(C2-C10)-alkynyl, —Z—(C6-C22)-aryl or Z—H, wherein Z=—CO—, —CO—NH—, —CS—NH—, —(CH2)n-[O—(CH2)r]s-, where r and s are, independently of each other, an integer between 1 to 18 and n is 1 or 2 independently from r and s,
  (7) substituents (2) to (6)
    wherein any alkyl, alkenyl, alkynyl or aryl can be substituted by one or more moieties selected from the group consisting of -halogen, —NO2, —OR12, —CN, —SH, —S—(C1-C6)-alkyl, —NR5R6, —N+R5R6R12, —COR11, —NH—CONR5R6, —NH—CSNR5R6 and —(CH2)n-[O—(CH2)r]s-

NR5R6, r and s are independently of each other an integer of from 1 to 18 and n is 0 or 1 independently from r and s,
wherein R11 is selected from the group consisting of —NHR12 and OR12,
wherein R5, R6 and R12 are selected independently from the group consisting of —H, —(C1-C10)-alkyl, —(C2-C10)-alkenyl, —(C2-C10)-alkynyl, —(C6-C22)-aryl and a reporter group,
said alkyl, alkenyl, alkynyl or aryl in substituents (2) to (7) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR$^5$R$^6$, r and s are independently of each other an integer of from 1 to 18 and n is 0 or 1 independently from r and s;
X is independent from R$^1$, R$^2$ or R$^3$ and is selected from the group consisting of N and CH
D is the position of attachment of the group to the rest of the nucleic acid binding compound.
with the proviso that one or two hydrogen atoms of any —OH, —SH, —NH$_2$, —NH-alkyl, —NH-alkenylene, —NH— alkynylene, or —NH-aryl group are substituted by a protecting group, and any salts thereof. Such compounds of Formula VI can be used for chemical synthesis of nucleic acid binding compounds according to the invention as precursors. In this case the compounds are linked to a solid phase, preferred R$^{14}$, R$^{15}$, or R$^{16}$ is O-solid phase, most preferred R$^{15}$ is solid phase. It is also preferred that reactive groups are protected by protective groups.

Also included in the present invention are precursors and intermediates of a nucleic acid binding compound, wherein the backbone comprises a moiety of the general formula III

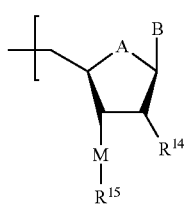

Formula III wherein
A is selected from the group consisting of O, S, CH$_2$ and N—(C$_1$-C$_6$)-alkyl,
M is selected from the group consisting of oxy, sulfanediyl, —NR$^{22}$—, —(C$_1$-C$_{10}$)-alkyl-, or —O—(C$_1$-C$_{10}$)-alkyl-O—, and —S—(C$_1$-C$_{10}$)-alkyl-O—, O—CO—, —NR$^{22}$—(C$_1$-C$_6$)-alkyl-O—,
R$^{22}$ is selected from the group of —H, —(C$_1$-C$_{10}$)-alkyl, a protecting group and a reporter group,
R$^{14}$ is selected from the group consisting of —H, —OH, —(C$_1$-C$_{10}$)-alkoxy, —(C$_2$-C$_{10}$)-alkenyloxy, —(C$_2$-C$_{10}$)-alkynyloxy, -halogen, -azido, SH, —(C$_1$-C$_{10}$)-alkylmercapto, O-reporter group, O-solid phase and —NH$_2$ linked to a protecting group,
R$^{15}$ is selected from the group consisting of —H, —(C$_1$-C$_6$)-alkyl, —(C$_2$-C$_{10}$)-alkenyl, —(C$_2$-C$_{10}$)-alkynyl, —(C$_2$-C$_{10}$)-alkyl-carbonyl, —(C$_3$-C$_{19}$)-alkenyl-carbonyl, —(C$_3$-C$_{19}$)-alkynyl-carbonyl, —(C$_6$-C$_{14}$)-aryl-(C$_1$-C$_{10}$)-alkyl and a solid phase, B is the link to a moiety of formula I,

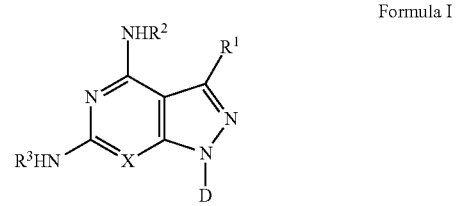

Formula I wherein
R1 is independent from X, R2 or R3 and is selected from the group consisting of
(1) —F, —Cl, —Br or —I,
(2) Nitro
(3) Cyano
(4) —COO—
(5) —(C1-C10)-alkyl substituted according to (10)
(6) —(C2-C10)-alkenyl substituted according to (10)
(7) —(C2-C10)-alkynyl substituted according to (10)
(8) —(C6-C22)-aryl substituted according to (10)
(9) —W—(C1-C10)-alkyl, —W—(C2-C10)-alkenyl, —W—(C2-C10)-alkynyl, —W—(C6-C22)-aryl or W—H, wherein W=—S—, —O—, —NH—, —S—S—, —CO—, —COO—, —CO—NH—, —NH—CO—, —NH—CO—NH—, —NH—CS—NH—, —(CH2)n-[O—(CH2)r]s-, where r and s are, independently of each other, an integer between 1 to 18 and n is 0 or 1 independently from r and s,
(10) substituents (5) to (9) wherein any alkyl, alkenyl, alkynyl or aryl can be substituted by one or more moieties selected from the group consisting of -halogen, —SH, —NO2, —CN, —S—(C1-C6)-alkyl, —NR5R6, —N+R5R6R12, —OR12, —COR1', —NH—CO—NR5R6, —NH—CS—NR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12, OR12, and —SR12
wherein R5, R6 and R12 are selected independently from the group consisting of —H, —(C1-C10)-alkyl, —(C2-C10)-alkenyl, —(C2-C10)-alkinyl, —(C6-C22)-aryl and a reporter group, a group which facilitates intracellular uptake or a group that, when the nucleic acid binding compound hybridizes to its complementary nucleic acid, attacks the latter while binding, cross-linking or cleaving,
(11)

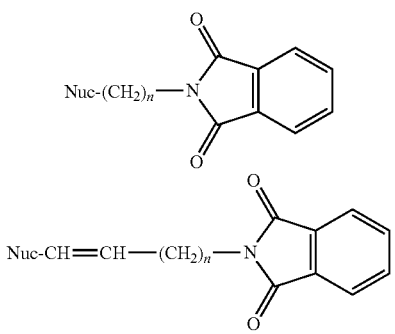

-continued

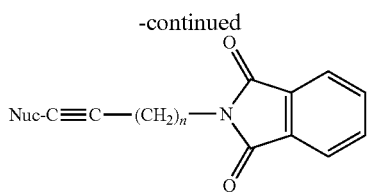

wherein Nuc is the link to formula I and n is any integer from 1 to 18 said alkyl, alkenyl, alkynyl or aryl in substituents (5) to (10) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s, with the proviso that R5, R6 or R12 is not a reporter group if the radicals (5) to (7) are substituted by —NR5R6, NHR12, OR12, or SR12;

R2, R3 is independent from X, R1, R2 and R3 and is selected from the group of,
(1) —H
(2) (C1-C10)-alkyl,
(3) (C2-C10)-alkenyl,
(4) (C2-C10)-alkynyl,
(5) (C6-C22)-aryl,
(6) —Z—(C1-C10)-alkyl, —Z—(C2-C10)-alkenyl, —Z—(C2-C10)-alkynyl, —Z—(C6-C22)-aryl or Z—H, wherein Z=—CO—, —CO—NH—, —CS—NH—, —(CH2)n-[O—(CH2)r]s-, where r and s are, independently of each other, an integer between 1 to 18 and n is 1 or 2 independently from r and s,
(7) substituents (2) to (6)
wherein any alkyl, alkenyl, alkynyl or aryl can be substituted by one or more moieties selected from the group consisting of -halogen, —NO2, —OR12, —CN, —SH, —S—(C1-C6)-alkyl, —NR5R6, —N+R5R6R12, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12 and OR12,
wherein R5, R6 and R12 are selected independently from the group consisting of —H, —(C1-C10)-alkyl, —(C2-C10)-alkenyl, —(C2-C10)-alkynyl, —(C6-C22)-aryl and a reporter group,
said alkyl, alkenyl, alkynyl or aryl in substituents (2) to (7) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s;

X is independent from $R^1$, $R^2$ or $R^3$ and is selected from the group consisting of N and CH D is the position of attachment of the group to the rest of the nucleic acid binding compound with the proviso that one or two hydrogen atoms of any —OH, —SH, —NH2, —NH-alkyl, —NH-alkenylene, —NH— alkynylene, or —NH-aryl group are substituted by a protecting group, and any salts thereof, wherein $R^{14}$ is O-solid phase or $R^{15}$ is solid phase.

Solid phases for chemical synthesis of a nucleic acid binding compound according to the invention preferably also include linkers to fix the growing nucleic acid binding compound. Such linkers are known in the art. Preferably such linkers can be cleaved after synthesis to free said nucleic acid binding compound and can for example also be used to generate a free 3'-hydroxy group in said nucleic acid binding compound. Such linkers are known in the art, for example succinic acid linked via an amide bond to the solid phase and via an ester to the precursor or intermediate. Preferred $R^{15}$ is solid phase, but in the precursor for chemical synthesis of a nucleic acid binding compound according to formula III alternatively $R^{14}$ may also be solid phase. Reactive groups of said compound are preferably protected by a protective group.

A more general formula of preferred precursors and intermediates according to the present invention are compounds comprising a backbone, said backbone having attached heterocyclic groups characterized in that a heterocyclic group is a group of the general formula I

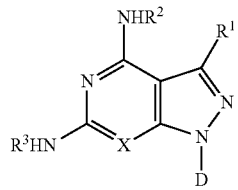

Formula I

R1 is independent from X, R2 or R3 and is selected from the group consisting of
(1) —F, —Cl, —Br or —I,
(2) Nitro
(3) Cyano
(4) —COO—
(5) —(C1-C10)-alkyl substituted according to (10)
(6) —(C2-C10)-alkenyl substituted according to (10)
(7) —(C2-C10)-alkynyl substituted according to (10)
(8) —(C6-C22)-aryl substituted according to (10)
(9) —W—(C1-C10)-alkyl, —W—(C2-C10)-alkenyl, —W—(C2-C10)-alkynyl, —W—(C6-C22)-aryl or W—H, wherein W=—S—, —O—, —NH—, —S—S—, —CO—, —COO—, —CO—NH—, —NH—CO—, —NH—CO—NH—, —NH—CS—NH—, —(CH2)n-[O—(CH2)r]s-, where r and s are, independently of each other, an integer between 1 to 18 and n is 0 or 1 independently from r and s,
(10) substituents (5) to (9) wherein any alkyl, alkenyl, alkynyl or aryl can be substituted by one or more moieties selected from the group consisting of -halogen, —SH, —NO2, —CN, —S—(C1-C6)-alkyl, —NR5R6, —N+R5R6R12, —OR12, —COR11, —NH—CO—NR5R6, —NH—CS—NR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12, OR12, and —SR12
wherein R5, R6 and R12 are selected independently from the group consisting of —H, —(C1-C10)-alkyl, —(C2-C10)-alkenyl, —(C2-C10)-alkinyl, —(C6-C22)-aryl and a reporter group, a group which facilitates intracellular uptake or a group that, when the nucleic acid binding compound hybridizes to its complementary nucleic acid, attacks the latter while binding, cross-linking or cleaving, said alkyl, alkenyl, alkynyl or aryl in substituents (5) to (10) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s, with the proviso that R5, R6 or R12 is not a reporter group if the radicals (5) to (7) are substituted by —NR5R6, NHR12, OR12, or SR12;

R2, R3 is independent from X, R1, R2 and R3 and is selected from the group of,
(1) —H
(2) (C1-C10)-alkyl,
(3) (C2-C10)-alkenyl,
(4) (C2-C10)-alkynyl,
(5) (C6-C22)-aryl,
(6) —Z—(C1-C10)-alkyl, —Z—(C2-C10)-alkenyl, —Z—(C2-C10)-alkynyl, —Z—(C6-C22)-aryl or Z—H, wherein Z=—CO—, —CO—NH—, —CS—NH—, —(CH2)n-[O—(CH2)r]s-, where r and s are, independently of each other, an integer between 1 to 18 and n is 1 or 2 independently from r and s,
(7) substituents (2) to (6)
wherein any alkyl, alkenyl, alkynyl or aryl can be substituted by one or more moieties selected from the group consisting of -halogen, —NO2, —OR12, —CN, —SH, —S—(C1-C6)-alkyl, —NR5R6, —N+R5R6R12, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12 and OR12,
wherein R5, R6 and R12 are selected independently from the group consisting of —H, —(C1-C10)-alkyl, —(C2-C10)-alkenyl, —(C2-C10)-alkynyl, —(C6-C22)-aryl and a reporter group,
said alkyl, alkenyl, alkynyl or aryl in substituents (2) to (7) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s;

X is independent from $R^1$, $R^2$ or $R^3$ and is selected from the group consisting of N and CH D is the position of attachment of the group to the rest of the nucleic acid binding compound.

wherein said backbone is solid phase bound,
with the proviso that one or two hydrogen atoms of any —OH, —SH, —NH2, —NH-alkyl, —NH-alkenylene, —NH—alkynylene, or —NH-aryl group are substituted by a protecting group,
and any salts thereof.

Beside the possibility that the precursor compound or intermediate is coupled to the solid phase at the backbone, it can also be linked at the heterocyclic group of formula I included in said compound, for example using a —OH, —SH or —NH2 groups as attachment site. Preferably the other reactive groups of said compound are protected by protective groups.

A preferred embodiment of the invention is a method for the determination of the presence, absence or amount of a nucleic acid comprising the steps of providing a sample suspected to contain the nucleic acid, providing a nucleic acid binding compound compound comprising a backbone, said backbone having attached heterocyclic groups capable of base pairing to nucleobases characterized in that a heterocyclic group is a substituted pyrazolo[3,4-d]pyrimidine or an analogue thereof, which is essentially complementary to a part or all of the nucleic acid, contacting said sample with the nucleic acid binding compound under conditions for binding the nucleic acid binding compound to the nucleic acid, determining the binding product or the degree of hybridization between the nucleic acid and the nucleic acid binding compound as a measure of the presence, absence or amount of the nucleic acid.

A further embodiment of the invention is a method for the determination of the presence, absence or amount of a nucleic acid wherein a nucleic acid binding compound is used as a capture probe, wherein the nucleic acid binding compound comprises a backbone, said backbone having attached heterocyclic groups capable of base pairing to nucleobases characterized in that a heterocyclic group is a substituted pyrazolo [3,4-d]pyrimidine or an analogue thereof.

Yet another embodiment of the invention is a method for distinguishing related nucleotide sequences in a nucleic acid, the method comprising the steps of providing a nucleic acid binding compound comprising a backbone, said backbone having attached heterocyclic groups capable of base pairing to nucleobases characterized in that a heterocyclic group is a substituted pyrazolo[3,4-d]pyrimidine or an analogue thereof and having a defined sequence, providing a nucleic acid with two related nucleotide sequences, each of which comprises a target sequence, wherein one of the nucleotide sequence is a target sequence that is perfectly complementary to the nucleic acid binding compound and at least one other of the segments is a related target sequence, incubating the nucleic acid with the nucleic acid binding compound under hybridization conditions, and determining the degree of hybridization between the nucleic acid binding compound and each of the segments.

Preferably any substituted pyrazolo[3,4-d]pyrimidine or an analogue thereof is located in said compound to pair with dT and to increase the melting point of the nucleic binding compound hybridized to its complementary nucleic acid. The expert in the field is aware of the fact that the increase of the melting point of a nucleic acid binding compound according to the invention is influenced by the environment of the heterocyclic group according to the invention. Preferably however, the melting point is 4.5 to 7° C. higher, preferably 5 or 5.5 to 7° C., more preferably 6 to 7° C. than the $T_m$ of a dA-dT pair.

In a very preferred embodiment, in the methods according to the invention the nucleic acids are isolated from biological material, preferably from a human or an animal. Preferably the methods according to the invention are used in the diagnostical field.

In still another embodiment of the invention a method as described above is contemplated wherein the nucleic acid binding compound according to the invention comprises a reporter group which is a fluorescent label, preferably fluorescein. Preferably, the nucleic acid binding compound according to the invention comprises multiple fluorescent labels wherein the emission wavelengths of one of the fluorescent labels overlaps the absorption wavelengths of another of the fluorescent labels. The nucleic acid binding compound may further comprise a quenching agent which quenches the fluorescence emission of the fluorescent label, which can be fluorescein. Preferably the quenching agent is a fluorescent rhodamine or cyanine. Preferably the method further comprises the step of altering the spatial relationship between the fluorescent label and the quenching agent subsequent to hybridization, preferably by exonuclease hydrolysis of the nucleic acid binding compound whereby release of label occurs as a result of exonuclease hydrolysis. In a preferred embodiment, the degree of hybridization between the nucleic acid binding compound and the nucleic acid is determined by the quantity of label that is released from the nucleic acid binding compound subsequent to hybridization.

In a preferred embodiment of the invention, a method for distinguishing related nucleotide sequences is disclosed, wherein the related sequences preferably differ by a single nucleotide. Preferably, the degree of hybridization between the nucleic acid binding compound and the nucleic acid is determined by the priming ability of the nucleic acid binding compound, wherein most preferably priming occurs as part of an amplification reaction which may be an amplification reaction described above. The amplification reaction is preferably a polymerase chain reaction.

In methods for the determination of the presence, absence or amount of a nucleic acid or the method for distinguishing related nucleotide sequences more than one nucleic acid binding compound may be used, wherein the nucleic acid binding compound comprises a backbone, said backbone having attached heterocyclic groups capable of base pairing to nucleobases characterized in that a heterocyclic group is a substituted pyrazolo[3,4-d]pyrimidine or an analogue thereof. Preferably, two nucleic acid binding compounds are used. In a preferred embodiment the first of the two nucleic acid binding compounds comprises a fluorescence donor and the second of the two nucleic acid binding compounds comprises a fluorescence acceptor, wherein the emission wavelengths of the fluorescence donor overlap the absorption wavelengths of the fluorescence acceptor. Then, the degree of hybridization can be measured by the quantity of light transferred between the fluorescence donor and the fluorescence acceptor and emitted by the fluorescence acceptor. In another embodiment the degree of hybridization is determined by the measurement of the melting temperature between the nucleic acid binding compound and the nucleic acid.

In yet another embodiment of the invention, a method for detecting the presence of a target sequence in a nucleic acid is disclosed, the method comprising the steps of providing a nucleic acid which is to be tested for the presence of the target sequence, providing a nucleic acid binding compound having a sequence that is substantially complementary to the target sequence and comprising a backbone, said backbone having attached heterocyclic groups capable of base pairing to nucleobases characterized in that a heterocyclic groups is a substituted pyrazolo[3,4-d]pyrimidine or an analogue thereof, incubating the nucleic acid and the nucleic acid binding compound under hybridization conditions; and identifying hybridized nucleic acids. Preferably, multiple nucleic acids are tested for the presence of the target sequence, whereby the nucleic acids have related target sequences. Most preferably, the nucleic acids differ from one another by a single nucleotide within the target sequence. Preferably, the nucleic acid binding compound is a primer comprising an extendible 3'-hydroxyl group. In a preferred embodiment, the hybridized nucleic acids are identified by extending the primer with a polymerizing enzyme, which can be a thermostable enzyme and wherein the nucleic acid binding compound is a primer in an amplification reaction, preferably a polymerase chain reaction. Preferably the thermostable enzyme is the DNA polymerase from *Thermus aquaticus*, the so-called Taq-Polymerase.

In still another embodiment of the invention, a method for primer extension is disclosed which comprises the steps of providing a nucleic acid containing a target sequence, providing one or more nucleic acid binding compounds complementary to the target sequence, wherein nucleic acid binding compound comprises a backbone, said backbone having attached heterocyclic groups capable of base pairing to nucleobases characterized in that a heterocyclic group is a substituted pyrazolo[3,4-d]pyrimidine or an analogue thereof, providing a polymerizing enzyme and nucleotide substrates, and incubating the nucleic acid, the nucleic acid binding compounds, the enzyme and the substrates under conditions favorable for polymerization. Preferably, the method is part of an amplification reaction, most preferably a polymerase chain reaction. The method can be used in the synthesis of a cDNA molecule.

Another embodiment of the invention is a method for determining the nucleotide sequence of a nucleic acid, the method comprising the steps of providing an array of nucleic acid binding compounds having different known sequences and comprising a backbone, said backbone having attached heterocyclic groups capable of base pairing to nucleobases characterized in that a heterocyclic group is a substituted pyrazolo[3,4-d]pyrimidine or an analogue thereof, with the proviso that the nucleic acid binding compounds do not contain a reporter group, incubating the nucleic acid with the array under hybridization conditions, and determining to which of the nucleic acid binding compounds in the array the nucleic acid hybridizes.

Still another embodiment of the invention is a method for determining the nucleotide sequence of a target sequence in a nucleic acid, the method comprising the steps of providing a nucleic acid comprising the target sequence, providing at least two nucleic acid binding compounds with a known sequence comprising a backbone, said backbone having attached heterocyclic groups capable of base pairing to nucleobases characterized in that a heterocyclic group is a substituted pyrazolo[3,4-d]pyrimidine or an analogue thereof, and wherein one of the at least two nucleic acid binding compounds has a sequence that is perfectly complementary to the target sequence and at least one other of the nucleic acid binding compounds has a related target sequence, incubating the nucleic acid binding compounds with the nucleic acid under hybridization conditions, and determining the degree of hybridization between each of the nucleic acid binding compounds and the nucleic acid. Preferably, the at least one other nucleic acid binding compounds has a single-nucleotide mismatch with the target sequence.

Further, the invention contemplates a method for examining gene expression in a cell, the method comprising the steps of providing a population of nucleic acids representative of the genes expressed in the cell, providing an array of nucleic acid binding compounds comprising a backbone, said backbone having attached heterocyclic groups capable of base pairing to nucleobases characterized in that a heterocyclic group is a substituted pyrazolo[3,4-d]pyrimidine or an analogue thereof, with the proviso that the nucleic acid binding compounds do not contain a reporter group, incubating the population of nucleic acids with the array under hybridization conditions, and determining which of the nucleic acid binding compounds in the array become hybridized to nucleic acids which is optionally labelled by incorporation of e.g. of adenosinetriphosphate coupled to a label.

Still another embodiment of the invention is a method for identifying a mutation in a target sequence of a gene of interest, the method comprising the steps of providing a nucleic acid that comprises the target sequence, providing an array of nucleic acid binding compounds of different sequences, wherein the different sequences include the wildtype target sequence and different mutant target sequences, wherein the nucleic acid binding compounds comprise a backbone, said backbone having attached heterocyclic groups capable of base pairing to nucleobases characterized in that a heterocyclic group is a substituted pyrazolo[3,4-d] pyrimidine or an analogue thereof with the proviso that the nucleic acid binding compounds do not contain a reporter group, incubating the nucleic acid with the array under hybridization conditions, and determining which of the nucleic acid binding compounds in the array become hybridized to the nucleic acid.

In all methods presented above the substituted pyrazolo[3, 4-d]pyrimidine analogue may be preferably the substituted pyrazolo[3,4-d]pyrimidine or an analogue thereof is a substituted 7-deaza-8-aza-2,6-diamino-purine or a derivative thereof or a 7-substituted 7-deaza-8-aza-2,6-diamino-purine or a derivative thereof. In another embodiment of the invention the substituted pyrazolo[3,4-d]pyrimidine analogue is a substituted pyrazolo[3,4-d]pyrimidine analogue of adenine or guanine or a 7-substituted pyrazolo[3,4-d]pyrimidine analogue of adenine or guanine, wherein the adenine or guanine analogues may preferably carry the same substituents $R^1$ in the 7-position or N-substituents $R^2$ and $R^3$ as set out directly below for the substituted 7-deaza-8-aza-2,6-diamino-purine or a derivative thereof or a 7-substituted 7-deaza-8-aza-2,6-diamino-purine or a derivative thereof.

In a preferred embodiment the substituted 7-deaza-8-aza-2,6-diamino-purine or a derivative thereof or the 7-substituted 7-deaza-8-aza-2,6-diamino-purine or a derivative thereof has the general formula I

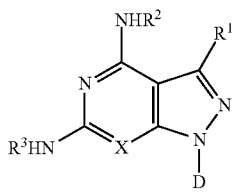

Formula I wherein
R1 is independent from X, R2 or R3 and is selected from the group consisting of
(1) —F, —Cl, —Br or —I,
(2) Nitro
(3) Cyano
(4) —COO—
(5) —(C1-C10)-alkyl substituted according to (10)
(6) —(C2-C10)-alkenyl substituted according to (10)
(7) —(C2-C10)-alkynyl substituted according to (10)
(8) —(C6-C22)-aryl substituted according to (10)
(9) —W—(C1-C10)-alkyl, —W—(C2-C10)-alkenyl, —W—(C2-C10)-alkynyl, —W—(C6-C22)-aryl or W—H, wherein W=—S—, —O—, —NH—, —S—S—, —CO—, —COO—, —CO—NH—, —NH—CO—, —NH—CO—NH—, —NH—CS—NH—, —(CH2)n-[O—(CH2)r]s-, where r and s are, independently of each other, an integer between 1 to 18 and n is 0 or 1 independently from r and s,
(10) substituents (5) to (9) wherein any alkyl, alkenyl, alkynyl or aryl can be substituted by one or more moieties selected from the group consisting of -halogen, —SH, —NO2, —CN, —S—(C1-C6)-alkyl, —NR5R6, —N+R5R6R12, —OR12, —COR11, —NH—CO—NR5R6, —NH—CS—NR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12, OR12, and —SR12 wherein R5, R6 and R12 are selected independently from the group consisting of —H, —(C1-C10)-alkyl, —(C2-C10)-alkenyl, —(C2-C10)-alkinyl, —(C6-C22)-aryl and a reporter group, a group which facilitates intracellular uptake or a group that, when the nucleic acid binding compound hybridizes to its complementary nucleic acid, attacks the latter while binding, cross-linking or cleaving,
said alkyl, alkenyl, alkynyl or aryl in substituents (5) to (10) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
with the proviso that R5, R6 or R12 is not a reporter group if the radicals (5) to (7) are substituted by —NR5R6, NHR12, OR12, or SR12;
R2, R3 is independent from X, R1, R2 and R3 and is selected from the group of,
(1) —H
(2) (C1-C10)-alkyl,
(3) (C2-C10)-alkenyl,
(4) (C2-C10)-alkynyl,
(5) (C6-C22)-aryl,
(6) —Z—(C1-C10)-alkyl, —Z—(C2-C10)-alkenyl, —Z—(C2-C10)-alkynyl, —Z—(C6-C22)-aryl or Z—H, wherein Z=—CO—, —CO—NH—, —CS—NH—, —(CH2)n-[O—(CH2)r]s-, where r and s are, independently of each other, an integer between 1 to 18 and n is 1 or 2 independently from r and s,
(7) substituents (2) to (6)
wherein any alkyl, alkenyl, alkynyl or aryl can be substituted by one or more moieties selected from the group consisting of -halogen, —NO2, —OR12, —CN, —SH, —S—(C1-C6)-alkyl, —NR5R6, —N+R5R6R12, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s,
wherein R11 is selected from the group consisting of —NHR12 and OR12,
wherein R5, R6 and R12 are selected independently from the group consisting of —H, —(C1-C10)-alkyl, —(C2-C10)-alkenyl, —(C2-C10)-alkynyl, —(C6-C22)-aryl and a reporter group,
said alkyl, alkenyl, alkynyl or aryl in substituents (2) to (7) being unsubstituted or substituted by one or more moieties selected from the group consisting of -halogen, —SH, —S—(C1-C6)-alkyl, —(C1-C6)-alkoxy, —OH, —NR5R6, —COR11, —NH—CONR5R6, —NH—CSNR5R6 and —(CH2)n-[O—(CH2)r]s-NR5R6, r and s are independently of each other an integer of from 1 to 18 and n is 0 or 1 independently from r and s;
X is independent from $R^1$, $R^2$ or $R^3$ and is selected from the group consisting of N and CH; and
D is the position of attachment of the group to the rest of the nucleic acid binding compound
or any salts thereof.

In still another preferred embodiment, the nucleic acid binding compound is a nucleic acid binding compound according to the invention, preferably $R^1$ is a hydrophobic or electron-withdrawing substituent as defined previously, preferably a halogen substituent whereby Br or I is most preferred.

In all the methods or uses of the present invention the nucleic acid binding compound having incorporated a heterocylic group according to the present invention can bind to an opposite strand to form a parallel or antiparallel duplex.

The invention furthermore relates to pharmaceutical compositions comprising one or more nucleic acid binding compounds containing a heterocyclic group of formula I, together with a physiologically acceptable excipients and, where appropriate, suitable additives and/or conventional auxiliary substances. Therefore, one embodiment of the invention is a pharmaceutical composition comprising a nucleic acid binding compound according to the invention. Another embodiment is a nucleic acid binding compound according to the invention for use in medicine. In a quite general manner, the present invention extends to the use of such nucleic acid binding compounds in therapeutically effective compositions. Such compositions are understood to mean to include the nucleic acid binding compounds according to the invention as antisense oligonucleotides, triple helix forming oligonucleotides, aptamers or ribozymes, in particular antisense oligonucleotides.

The invention further contemplates protecting groups derived from phthalic acid (see e.g. Ramzaeva et al. (1999). Nucleosides & Nucleotides 18, 1439-1440; Rich B. Meyer in Methods in Molecular Biology 26 (1994), pp. 73-91, Humana Press Inc. Totowa, N.J., USA; Griffey et al. (1996). J. Med. Chem. 39, 5100-5109; Gibson and Benkovic (1987). Nucl. Acids Res. 15, 6455-6467). Aminoalkinyl or aminoalkenyl side chains of the pyrazolo[3,4-d]pyrimidin analogues of desoxyadenosine, desoxy-guanosine or desoxy-isoguanosine may be protected with phthalic whereby an imide is formed. In contrast to the trifluoroacetyl protecting group which may be removed relatively easy from an oligonucleotide, the removal of a phthaloyl group from aliphatic side chains is not easy as e.g. for peptides. Therefore, hydrazine would have to be used which cannot however be used in the case of oligonucleotides, as pyrimidine nucleosides are degraded. The amino groups of alkynyl compounds, in particular of propargylamine as well as those which are in allyl position on other positions in the chain are less basic. Thereby, a phthaloyl group may be more easily removed and no methyl amine has to be used. The deprotection is performed under standard conditions, i.e. concentrated ammonia solution at 60° C., 12 hours. The advantage of the phthaloyl group is that both H-atom positions of the amino group are acylated. For normal acyl groups as e.g. the trifluoroacetyl (TFA) group used in U.S. Pat. No. 5,151,507, the amino group is capped by acylation and is monofunctionalized thereafter. Later the TFA group is removed whereby the acetyl group remains bound and is difficult to remove. The advantage of the phthaloyl group for such purposes is obvious.

Hence, in one embodiment of the invention a building block for the synthesis of an oligonucleotide comprising the nucleosides adenosine or desoxyadenosine, guanosine or desoxyguanosine, isoguanosine or desoxyisoguanosine, cytidine or deoxycytidine, uridine or desoxyuridine, thymidine or desoxythymidine, or analogues of these nucleosides wherein a substituent is attached to the base moiety selected from the group of phthalimidoalkyl, phthalimidoalkenyl, or phthalimidoalkynyl groups with the following formulas

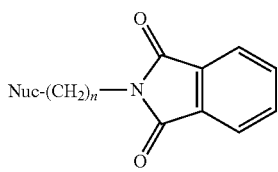

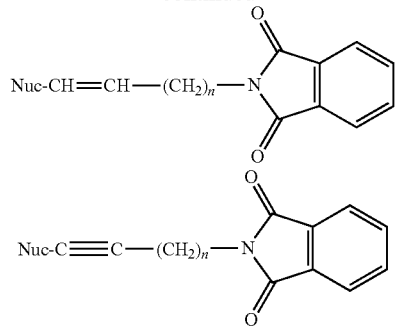

wherein Nuc is the position of attachment of the substituent to the base moiety and n is any integer from 1 to 18, with the proviso that the phthalimidoalkynyl or phthalimidoalkyl group is not attached to the C5-atom of deoxyuridine and the proviso that the phthalimidoalkynyl group is not attached to the C7-atom of 7-deaza-deoxyguanosine. In a preferred embodiment the analogue of these nucleosides is a pyrazolo [3,4-d]pyrimidine analogue. In a further preferred embodiment, the building block according to the invention is a phosphoramidite derivative.

Further the invention contemplates the use of a building block according to the invention for the synthesis of an oligonucleotide. Further, the use of a phthaloyl group as a protecting group is contemplated in a method for the synthesis of an oligonucleotide from building blocks comprising the nucleosides adenosine or desoxyadenosine, guanosine or desoxyguanosine, isoguanosine or desoxyisoguanosine, cytidine or deoxycytidine, uridine or desoxyuridine, thymidine or desoxythymidine, or analogues of these nucleosides wherein the amino groups of —$(CH_2)_n$—$NH_2$, —CH=CH— $(CH_2)_n$—$NH_2$, or —C≡C—$(CH_2)_n$—$NH_2$ attached to the base moiety are derivatized with the phthaloyl group and n is any integer from 1 to 18, with the proviso that the —$(CH_2)_n$—$NH_2$ or —C≡C—$(CH_2)_n$—$NH_2$ group is not attached to the C5-atom of deoxyuridine and the proviso that the —C≡C—$(CH_2)_n$—$NH_2$ group is not attached to the C7-atom of 7-deaza-deoxyguanosine. In a preferred embodiment the analogue of these nucleosides is a pyrazolo[3,4-d] pyrimidine analogue. In a further preferred embodiment, the building block is a phosphoramidite derivative.

In yet another embodiment of the invention, a method for the synthesis of an oligonucleotide from building blocks according to the invention is disclosed.

These examples are intended to illustrate possible applications and should not limit the scope of the invention.
The present invention is explained in more detail by the following examples:

EXAMPLES

Example 1

Synthesis and data on the 7-promo-8aza-7-deazapurin-2,6-diamine nucleosides 1.1. Synthesis and Properties of Monomers The alkoxy nucleosides 4a,b [18] served as precursor for the synthesis of the 8-aza-7-deazapurin-2,6-diamine (pyrazolo[3,4-d]pyrimidin-4,6-diamine) nucleosides 2a,b (purine numbering is used throughout the discussion section) The amination was performed in a steel bomb (4 days, 25% aq. $NH_3$, 70°. Both nucleosides (2a,b) were isolated crystalline. A few related 8-aza-7-deazapurin-2,6-diamine nucleosides have been prepared earlier [19-22].

Treatment of compound 2a with adenosine deaminase (ADA) resulted in the formation of 8-aza-7-deaza-2'-deoxyguanosine [18]. The reaction was followed UV-spectrophoto-metrically (FIG. 1a).

The time-dependent spectra show two isosbestic points ($\lambda$=234 nm and 267 nm) indicating the conversion of the starting material into only one reaction product. The deamination of 2a occurs much slower than that of the purine nucleoside 1. The 7-bromo derivative 2b [18] was not deaminated under these conditions even at high enzyme concentrations as it was observed earlier [20].

Next, the half-lives of the N-glycosylic bonds of compounds 2a,b in acidic medium were measured and compared with that of compound 1. The reaction was performed in 0.5 N HCl at room temperature and was followed UV-spectrophotometrically as well as by HPLC-analysis (Table 1).

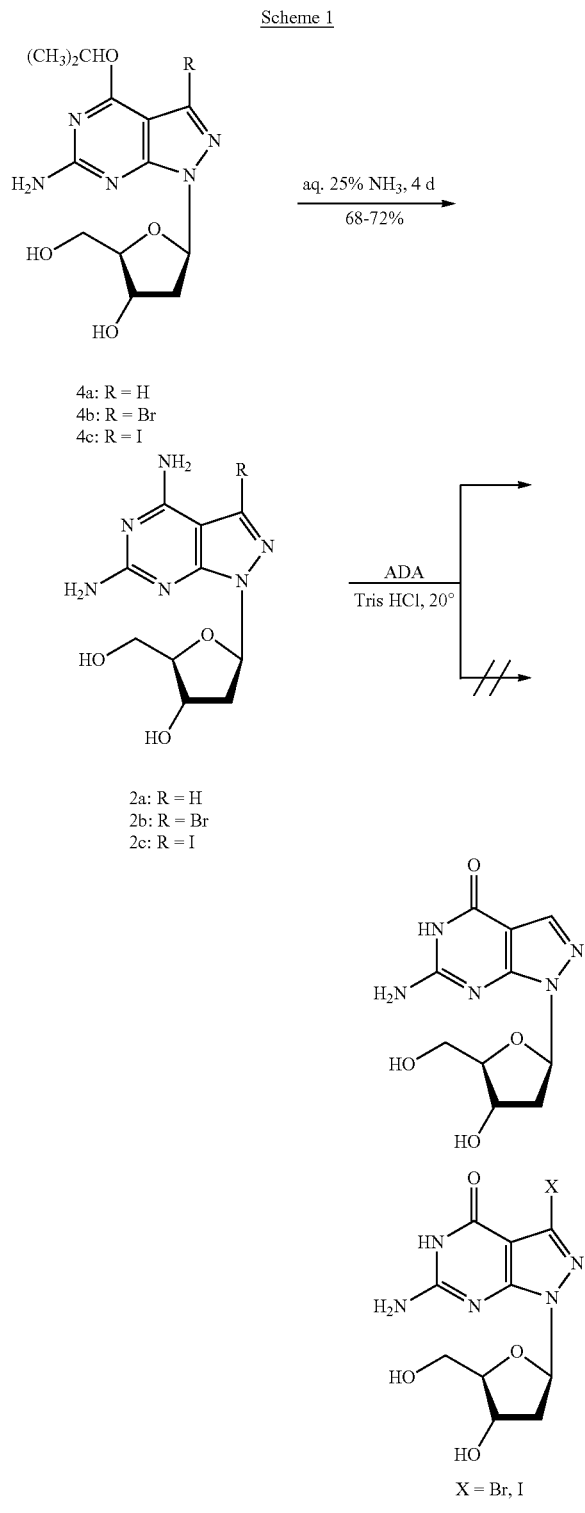

Scheme 1

TABLE 1

Half-life Values ($\tau$) of 2'-Deoxyadenosine Derivatives in HCl at 25°.

| Compound | $\tau$ [min][a]) | $\lambda$(nm) |
|---|---|---|
| 1 | 6 | 252 |
| 2a | 91 | 255 |
| 2b | Stable[b]) | 242 |
| 2b | 87[c]) | 242 |

[a])Measured in 0.5 N HCl.
[b])Within 4 h.
[c])Measured in 2 N HCl.
[d]) Determined by HPLC.

Figure 1B:
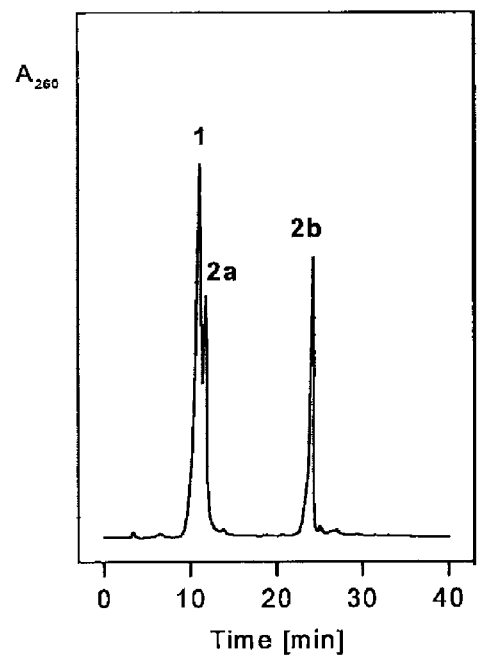
FIG. 1b: High pressure liquid chromatography (HPLC) profile of compounds 1, 2a and 2b

From the data of the table it is apparent that the 8-aza-7-deazapurin-2,6-diamine nucleoside (2a) shows an about 15-fold higher glycosylic bond stability than the parent 2-amino-2'-deoxyadenosine (1). The glycosylic bond of 2b is stable under these conditions. Hydrolysis occurs when the reaction is performed in 2 N HCl (Table 1). Furthermore, the 7-bromo substituent increases the lipophilic character of the molecule thereby decreasing the chromatographic mobility of compound 2b, in comparison to compounds 2a or 1 on reverse phase HPLC (FIG. 1b).

In order to study the influence of the nucleobases on the N↔S pseudorotational equilibrium of the sugar moiety, the $^1$H-NMR spectra of the nucleosides 1-3 were measured in $D_2O$. The analysis was performed on the basis of five vicinal $^1$H,$^1$H coupling constants using the PSEUROT program [23]. According to Table 2 the 8-aza-7-deazapurin-2,6-diamine nucleoside 2a shows a more pronounced N-conformer population than the corresponding purine nucleoside 1, while the N-type population of the related 7-deazapurine nucleoside 3 is decreased. This is in line with an increase of the □-electron deficiency of the 8-aza-7-deazapurine system. An additional effect of the electron-withdrawing 7-bromo substituent is not observed (2b) but was found for the more electron-attracting cyano group introduced into the 7-position of 8-aza-7-deaza-2'-deoxyguanosine [24]. The conformation around the C(4')—C(5') bond indicates that the 8-aza-7-deazapurin-2,6-diamine nucleosides 2a and b as the 8-aza-7-deaza-2'-deoxyguanosines [24], prefer the $\gamma^t$-(-sc)-rotamer population, while for the regular purine nucleosides the $\gamma^{(+)g}$-(+sc)- or the $\gamma^{(-)g}$-(ap)-conformation is predominant [25].

TABLE 2

$^3$J (H, H) Coupling Constants of the Sugar Moieties and N/S-Conformer Populations of the 2'-Deoxyribonucleosides 1-3 at 303 K.$^a$)

| | $^3J_{H,H}$/Hz | | | | | | | Conformation | | | | |
|---|---|---|---|---|---|---|---|---|---|---|---|---|
| | 1',2' | 1',2" | 2',3' | 2",3' | 3',4' | 4',5' | 4',5" | % N | % S | $\gamma^{(+)g}$ | $\gamma^t$ | $\gamma^{(-)g}$ |
| 1  | 7.30 | 6.10 | 7.00 | 3.10 | 3.40 | 3.20 | 4.30 | 31 | 69 | 62 | 25 | 13 |
| 2a | 6.60 | 6.80 | 6.90 | 3.70 | 3.60 | 4.00 | 5.80 | 37 | 63 | 36 | 42 | 22 |
| 2b | 6.60 | 6.70 | 6.80 | 3.70 | 3.90 | 4.30 | 5.90 | 37 | 63 | 32 | 43 | 25 |
| 3  | 7.90 | 6.40 | 6.20 | 3.10 | 3.00 | 3.87 | 4.82 | 25 | 75 | 48 | 32 | 20 |

$^a$)Solvent D$_2$O; r.m.s. < 0.4 Hz; |ΔJ$_{max}$| < 0.4 Hz.

In the past several laboratories have reported on a straightforward protection protocol for 2-amino-2'-deoxyadenosine (1). Drastic hydrolysis conditions are necessary for the complete removal of benzoyl protecting groups [4] while the more labile phenoxyacetyl (pac) residues were removed without difficulty [26], [27]. Nevertheless, the formation of the N-bis-acylated derivatives is encountered with difficulties due to the monoprotection of the molecule [28] and an increased tendency of the acylated derivatives to be subjected to depurination [4]. According to the observation that the nucleosides 2a,b are significantly more stable than the purine nucleoside 1 (Table 1) the N-acyl derivatives of 2a,b should show similar properties. Therefore, the phenoxyacetyl derivative 5a as well as the benzoyl compound 5b were prepared employing the protocol of transient protection [29]. 2,4,5-Trichlorophenylphenoxy acetate [27] or benzoyl chloride [30] were used as acylation reagents The bis-phenoxyacylated derivative 5a was formed as it was described for the purine compound 1 [19]. However, the yield of 5a was rather low (30%). The bis-benzoylated nucleoside 5b was isolated in much better yield (63%) (Scheme 2; a) 6a: Pyridine; Me$_3$SiCl, 2,4,5-trichlorophenylphenoxyacetate, 40°, 12 h. 6b: Pyridine, Me$_3$SiCl, PhCOCl, r.t., 12 h. b) Pyridine/(MeO)$_2$Tr-Cl, r.t., 4 h. c) THF, 2-cyanoethyl diisopropylphosphoramidochloridite, r.t. 30 min) Both compounds (5a,b) were converted into the DMT-derivatives 6a,b using the standard reaction conditions [31]. Phosphitylation in the presence of 2-cyanoethyl diisopropylphosphoroamidochloridite and ($^i$Pr)$_2$EtN afforded the phosphoramidites 7a,b [32]. However, as the benzoylated derivative 6b is poorly soluble in THF-solution, a large volume had to be used. According to this the phosphitylation was less effective and the yield of the phosphoramidite which is normally in the range of 80% was decreased to 67% (Scheme 2).

Scheme 2

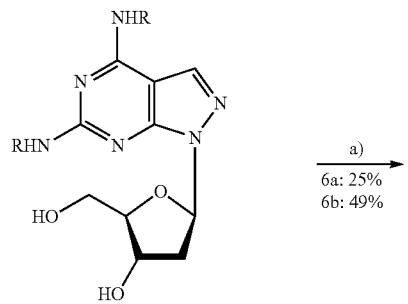

5a: R = Pac
5b: R = Bz

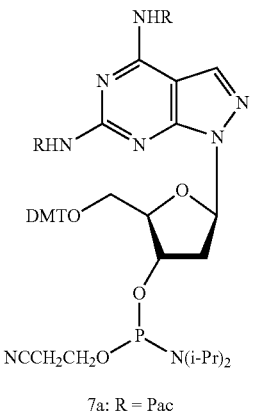

6a: R = Pac
6b: R = Bz

7a: R = Pac
7b: R = Bz

Deprotection of compound 5a (25% aq. NH$_3$, 40°, HPLC-monitoring) showed that the first pac-group is removed within 5 min, while the removal of the second pac-group afforded 20 min. At r.t. a complete deprotection takes place in less than one hour. The complete removal of the two benzoyl groups of compound 5b (25% aq. NH$_3$, 40°, HPLC monitoring) requires 8-9 h while the deprotection of the bis-benzoylated purine nucleoside 1 afforded several days [4] [7]. From this point of view the benzoyl-protected phosphoramidite 7b represents a useful building block for the incorporation of compound 2a in oligonucleotides. Nevertheless, the low solubility of the intermediate 6b represents a problem.

In spite of this the synthesis of the N,N'-dialkylmethyliden derivatives was 8a,b undertaken. Original attempts to introduce N,N'-dimethylaminomethylidene residues into the purine nucleoside 1 failed due to the instability of the protecting groups [28]. The N,N-dibutylaminomethyliden group [33] for the protection of the exocyclic amino function of an 8-aza-7-deazapurine analogue of 2'-deoxyisoguanosine was used previously [34]. The same group was now introduced into the nucleosides 2a,b. The bis-amidines 8a,b were obtained as the major products (50% yield), while the mono adducts (9a,b) were formed as minor components (17%). The formation of the mono adduct might be circumvented when the more vigorous conditions are used. For the protected nucleoside 8a,b the time of complete deprotection (conc. ammonia, 40°, HPLC-monitoring at 260 nm) was determined to be 440 min for 8a and 450 min for 8b. A half-live value cannot be given as a mono-protected intermediate is formed.

group is still carrying the dibutylaminomethylidene residue. The structure of compounds 10a,b was established on the basis of NMR spectra. The amino group (10.77 ppm) and the proton of the formyl residue (9.56 ppm) are split in doublets with J=9.88 Hz. This characteristic coupling pattern has already been observed for the formyl derivatives of 5-aza-7-deaza-2'-deoxyguanosine [35] and 2-amino-8-aza-7-deazapurine 2'-deoxynucleoside [36]. Phosphitylation of the DMT-derivatives 10a,b was performed in THF in the presence of chloro(2-cyanoethyl)-(diisopropylamino)phosphine

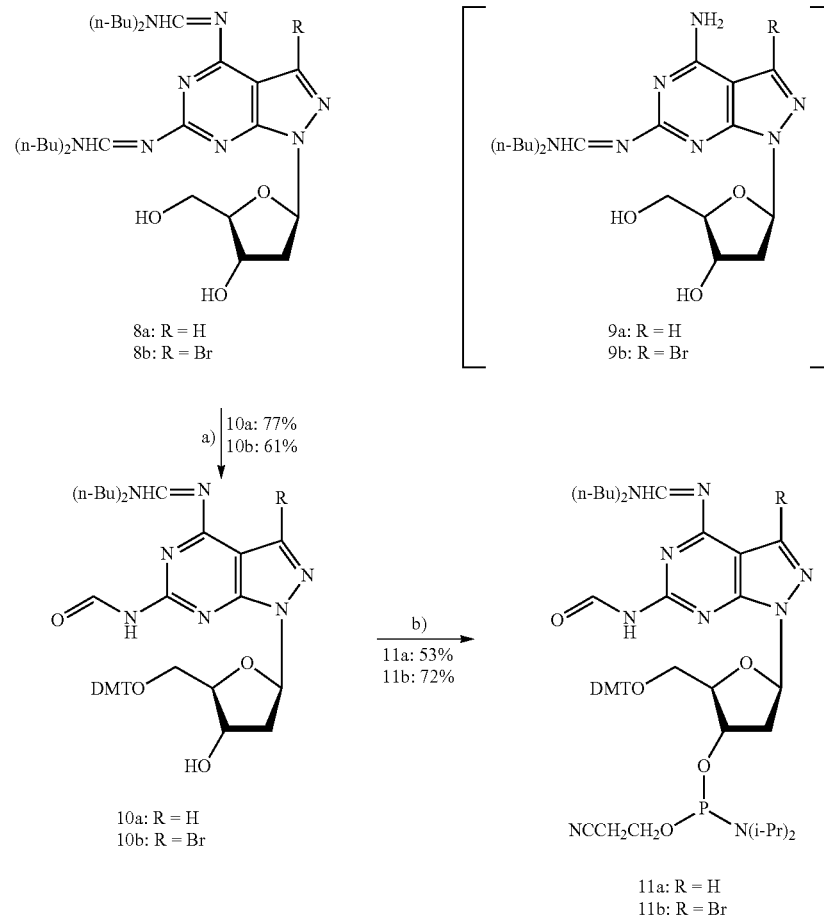

Scheme 3

Subsequently, the 4,4'-dimethoxytrityl residues were introduced. After the work-up of the reaction followed by silica gel flash-chromatography one N,N'-dibutylaminomethylidene residue was hydrolyzed to give a formyl group (Scheme 3; a) Pyridine/(MeO)$_2$Tr-C1, r.t., 4 h. b) THF, 2-cyanoethyl diisopropyl-phosphoramidochloridite, r.t., 30 min). This group is now protecting the 2-amino function, while the 6-amino furnishing the phosphoramidites 11a,b (Scheme 3). These phosphoramidites as well as the corresponding building block 7b carrying benzoyl protecting groups can be efficiently used in solid-phase oligonucleotide synthesis resulting in high coupling yields. All compounds were characterized by $^1$H-, $^{13}$C-, and $^{31}$P-NMR spectra and by elemental analysis (Table 3 and experimental part).

TABLE 3

| | $^{13}$C-NMR Chemical Shifts of Pyrazolo[3,4-d]pyrimidine 2'-Deoxyribonucleosides[a] | | | | | | | | | | | |
|---|---|---|---|---|---|---|---|---|---|---|---|---|
| | C(2)[b,d] C(6)[c] | C(4)[d] C(7a) | C(5) C(3a) | C(6)[d] C(4) | C(7) C(3) | C=O/ =CH | C=O/ =CH | C(1') | C(2') | C(3') | C(4') | C(5') |
| 2a | 156.9 | 158.3 | 95.5 | 162.7 | 133.3 | — | — | 83.3 | 38.0 | 71.3 | 87.4 | 62.7 |
| 2b | 157.4 | 157.6 | 94.5 | 162.7 | 119.2 | — | — | 83.0 | 37.5 | 70.9 | 87.3 | 62.4 |

TABLE 3-continued

13C-NMR Chemical Shifts of Pyrazolo[3,4-d]pyrimidine 2'-Deoxyribonucleosides[a]

| | C(2)[b,d] C(6)[c] | C(4)[d] C(7a) | C(5) C(3a) | C(6)[d] C(4) | C(7) C(3) | C=O/ =CH | C=O/ =CH | C(1') | C(2') | C(3') | C(4') | C(5') |
|---|---|---|---|---|---|---|---|---|---|---|---|---|
| 5a | 152.2 | 154.8 | 100.5 | 156.1 | 136.1 | 168.5 | 169.1 | 83.6 | 37.7 | 71.1 | 87.7 | 62.5 |
| 5b | 153.3 | 155.2 | 102.2 | 156.1 | 134.0 | 165.6 | 166.3 | 83.5 | 37.6 | 70.9 | 87.5 | 62.3 |
| 6a | 152.2 | 154.8 | 100.5 | 155.9 | 135.9 | 168.5 | 169.2 | 83.7 | 38.1 | 70.8 | 85.6 | 64.3 |
| 6b | 153.3 | 155.3 | 102.3 | 156.1 | 132.2 | 165.7 | 166.4 | 83.7 | 38.0 | 70.9 | 85.6 | 64.4 |
| 8a[f] | 157.1 | 157.6 | 106.0 | 158.9 | 134.9 | 164.1 | 166.2 | 86.1 | 41.2 | 73.7 | 89.1 | 64.3 |
| 8b | 156.1 | 156.1 | 103.6 | 157.9 | 121.4 | 162.1 | 164.4 | 83.3 | 37.5 | 70.8 | 87.5 | 62.2 |
| 8b[f] | 157.1 | 157.7 | 104.7 | 159.2 | 122.9 | 163. | 166.7 | 86.2 | 41.0 | 73.8 | 89.0 | 64.2 |
| 9[c] | 156.6 | 157.3 | 102.4 | 162.3 | 133.7 | 162.9 | —[e] | 83.1 | 37.8 | 71.2 | 87.3 | 62.6 |
| 10a[f] | 155.5 | 155.5 | 107.1 | 156.8 | 134.9 | 161.8 | 163.7 | 84.2 | 38.3 | 73.6 | 86.7 | 64.9 |
| 10b | 156.0 | 156.1 | 103.8 | 157.8 | 121.3 | 162.1 | 164.4 | 83.5 | [e] | 70.5 | 85.3 | 64.1 |

[a])Measured in (D6)DMSO at 298 K.
[b])Purine numbering.
[c])Systematic numbering.
[d])Tentative.
[e])Superimposed by (D6)DMSO.
[f])Measured in CDCl3.

1.2. Oligonucleotides
1.2.1 Synthesis and Characterization.

Figure 2A:
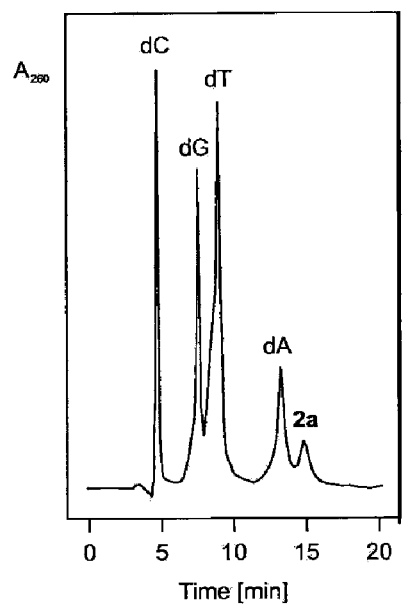
FIG. 2a: High pressure liquid chromatography (HPLC) profile of a snake venom diesterase/alkaline phosphatase hydrolysate of an oligonucleotide containing 2a FIG. 2b: High pressure liquid chromatography (HPLC) profile of a snake venom diesterase/alkaline phosphatase hydrolysate of an oligonucleotide containing 2b

Automated solid-phase synthesis of the oligonucleotides 102-116 (Tables 4-6) was performed using the phosphoramidites 7b and 11b as well as standard phosphoramidites. The oligonucleotides were detritylated and purified on oligonucleotide purification cartridges or by reversed-phase HPLC (conditions for purification see experimental part). The homogeneity of the compounds was proven by ion-exchange chromatography on a 4×250 mm NucleoPac PA-100 column (DIONEX, P/N 043018, USA). The composition of the oligonucleotides was determined by tandem hydrolysis with snake venom phosphodiesterase and alkaline phosphatase as described (see FIG. 2a,b) [2].

Figure 2B:
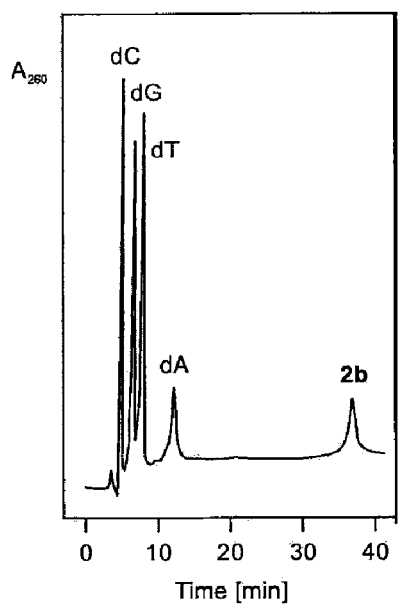

The 8-aza-7-deazapurin-2,6-diamine nucleosides 2a migrates slightly slower than dA. The bromo compound 2b is much more hydrophobic as it can be seen from the FIG. 2b. From the modified oligonucleotides MALDI-TOF mass spectra were taken (Table 6, Experimental part). The correct mass was found in all cases which underlines that all protecting groups were split off during a 10 h ammonia treatment at 60°.

1.2.2 Duplex Stability

Because of the presence of three hydrogen bonds the $n^2A_d$-dT base pair (II) is expected to show the same or a similar stability as a dG-dC pair (III). Experimental data obtained from DNA-melting experiments show that the thermodynamic stability of duplexes containing an $n^2A_d$-dT base pair is somewhat higher than that with a dA-dT pairs but still remains far below that of a dG-dC pair. Various studies have been performed to explain this dilemma but a convincing answer has not been given. A rather detailed examination of this matter has been undertaken by Sagy et al [11]. This author compared the thermal stabilities of a bidentate base pair represented by the motifs dA-dU, dI-dC, dA-dT and dI-$m^5C_d$ with those of tridentade pairs such as $n^2A_d$-dT, dG-dC, dG-$m^5C_d$ and others. The experiments were performed with alternating polynucleotides synthesized enzymatically. As long as a 2-amino group was absent (bidentate bases pairs), the various duplexes show all a very similar stability independently from the particular base structure. By insertion of a 2-amino group, which leads to the tridentate base pair this similarity disappears. The dG-dC base pair is now much more stable than the $n^2A_d$-dT pair. The authors noted also a significant effect of the 5-substituents attached to the pyrimidine moiety; while the presence of a 5-methyl group results in a rather small stabilization; larger alkyl groups destabilize the DNA.

Scheme 4

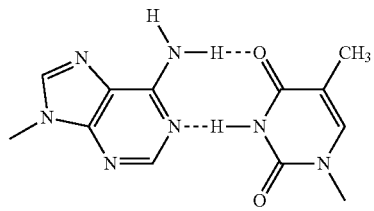

Watson Crick Base Pair I

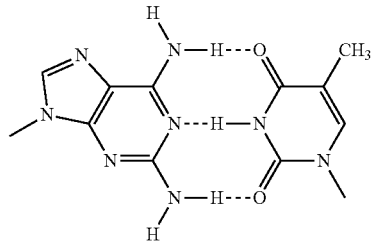

Watson Crick Base Pair II

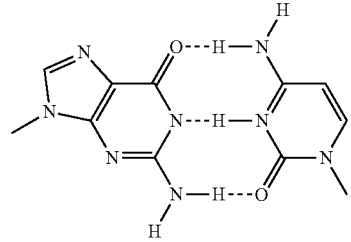

Watson Crick Base Pair III

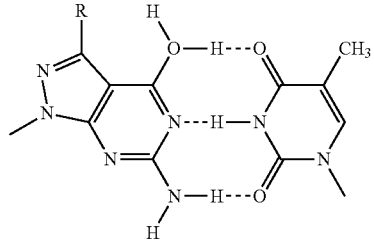

Watson Crick Base Pair IV
R = H, Br

In order to evaluate the influence of the 8-aza-7-deazapurin-2,6-diamine nucleosides 2a,b on the base pair stability in comparison to the purine nucleoside 1 all three compounds were incorporated into the non-self-complementary duplex 5'-d(TAGGTCAATACT) (102) (SEQ ID NO: 2) and 5'-d(AGTATTGACCTA) (103) (SEC) ID NO: 3). This duplex is used as a standard in our laboratory to study the influence of modified nucleosides on the thermal stability and the structural behavior of the helical formation. The $T_m$-value of (102•103) is 46° in 0.1 M NaCl in the presence of 10 mM MgCl$_2$ and 10 mM Na-cacodylate buffer. The incorporation of six n$^2$A$_d$-residues instead of six dA residues increases the $T_m$-value by only 4° (see duplex 104•105, Table 4). This corresponds to a 0.7° $T_m$-increase per residue. Similar findings have been reported from experiments performed in other laboratories [5-12]. When four 8-aza-7-deazapurin-2,6-diamine nucleosides 2a were replacing dA an increase of the $T_m$-value already from 46° to 52° was measured, which corresponds to a 1.5° increase per modified residue (compare duplexes 102•103 vs. 108•109). As the stability increase caused by an n$^2$A$_d$-residue was only 0.7°, the 8-aza-7-deazapurin-2,6-diamine forms a more stable tridentate base pairs with dT than that of the purin-2,6-diamine.

An explanation for this unexpected observation can be given on the basis of the basicity differences of the amino groups of the 8-aza-7-deazapurin-2,6-diamine nucleosides 2a,b compared to that of the purin-2,6-diamine nucleoside 1. As discussed above the third hydrogen bond of compound 1 contributes very little to the n$^2$A$_d$-dT base pair stability (Scheme 4, base pair II) while the 2-amino group of dG makes a large contribution to the stability of a dG-dC pair. With regard to the chemical structure of the molecule, both, the amino group of dG and isoG$_d$ are part of an actylated guanidine moiety which is expected to be considerably less basic than the 2-amino group of n$^2$A$_d$ which is also a part of guanidine system being now aromatic but is not connected to an electron-attracting moiety. These differences cause the low acidity of the 2-amino group of 1 compared to dG or isoG$_d$. This property is already noticeable in the extraordinary resistance of the acylated 2-amino group of 1 against alkaline deprotection (see above). Next, the question has to be answered why compounds 1 and 2a,b are different. Contrary to compound 1, one can draw mesomeric structures of the base of compounds 2a,b with a positive charge either at the 2- or the 6-amino group and a negative one at the pyrazole nitrogen-2.

These mesomeric formulas explain the acidity (reduced basicity) of the 2-amino group of 2a over that of 1. When a

TABLE 4

$T_m$ Value and Thermodynamic Data of Antiparallel Stranded Oligonucleotides Containing Purin-2,6-diamine 2'-Deoxyribonucleoside and Related Pyrazolo[3,4-d]-pyrimidine Analogs.[a]

| | SEQ ID NO: | $T_m$ [° C.] | ΔH° [kcal/mol] | ΔS° [cal/mol · K] | ΔG°$_{310}$ [kcal/mol] |
|---|---|---|---|---|---|
| 5'-d(TAG GTC AAT ACT) (102) · (103)<br>3'-d(ATC CAG TTA TGA) | 2<br>3 | 46 | −86 | −230 | −10.3 |
| 5'-d(T1G GTC 11T 1CT) (104) · (105)<br>3'-d(ATC C1G TT1 TGA) | 4<br>5 | 50 | −58 | −155 | −11.2 |
| 5'-d(TAG GCC GGC ACT) (106) · (107)<br>3'-d(ATC CGG CCG TGA) | 6<br>7 | 65 | −92 | −247 | −16.0 |
| 5'-d(TAG GTC 2a2aT ACT) (108) · (109)<br>3'-d(ATC C2aG TT2a TGA) | 8<br>9 | 52 | −105 | −299 | −12.7 |
| 5'-d(TAG GTC 2b2bT ACT) (110) · (111)<br>3'-d(ATC C2bG TT2b TGA) | 10<br>11 | 68 | −110 | −297 | −17.9 |
| 5'-d(TAG GTC 2b2bT ACT) (110) · (103)<br>3'-d(ATC CAG TTA TGA) | 10<br>3 | 56 | −85 | −232 | −12.9 |
| 5'-d(TAG GTC AAT ACT) (102) · (111)<br>3'-d(ATC C2bG TT2b TGA) | 2<br>11 | 58 | −88 | −239 | −13.4 |

[a]Measured at 260 nm in 0.1 M NaCl, 0.1 M MgCl$_2$, and 10 mM Na-cacodylate buffer, pH 7.0 with 5 + 5 µM oligomer concentration.

It has been shown that 7-substituents of 7-deazapurines as well as of 8-aza-7-deazapurine are well accommodated in the major groove of DNA [1-3]. In particular, halogen substituents show very favorable properties with regard to duplex stability. This prompted us to replace dA-residues now by the 7-bromo derivative 2b. According to Table 4 the duplex (20•21) shows a remarkable stability. The $T_m$-value was 68° compared to 46° of the duplex with dA-dT pairs. The duplex stability is strengthened by 5.5° per modified base. The duplex (106•107) containing four dG-residues at the same positions lead to a $T_m$-value of 65° which corresponds to a 5° $T_m$-increase. Thus, the stability of a base pair motif IV (Scheme 4) which follows a dA-dT recognition motif is now as stable as a dG-dC pair (base pair III).

bromo or other electron-attracting substituents are introduced at the 7-position this effect is even strengthened. Thus, the 2-amino-group of 2a will become a better donor for hydrogen bonds with dT than the 2-amino group of 1. The additional bromo substituent can cause several favorable effects: (i) It acidifies the 2-amino group further; (ii) it represents a hydrophobic group in the major groove of the DNA-duplex; (iii) it can form a hydrogen bond with the 2-amino group. Apart from these properties of the monomeric units the environmental conditions of the base within the nucleic acid duplexes have to modulate the stability of the n$^2$A-dT base pairs. Otherwise, it cannot be explained why the stability of such a base pair is different in DNA-duplexes, DNA-RNA hybrids or PNA-duplexes.

Scheme 5

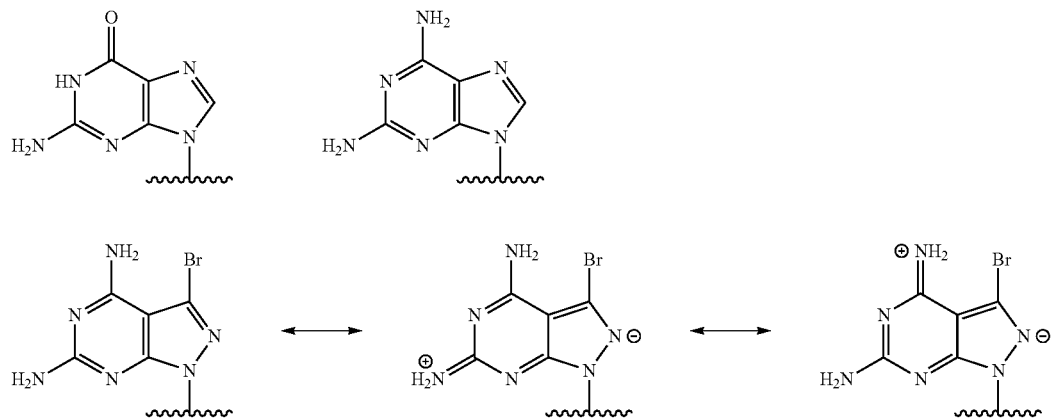

Figure 3A:
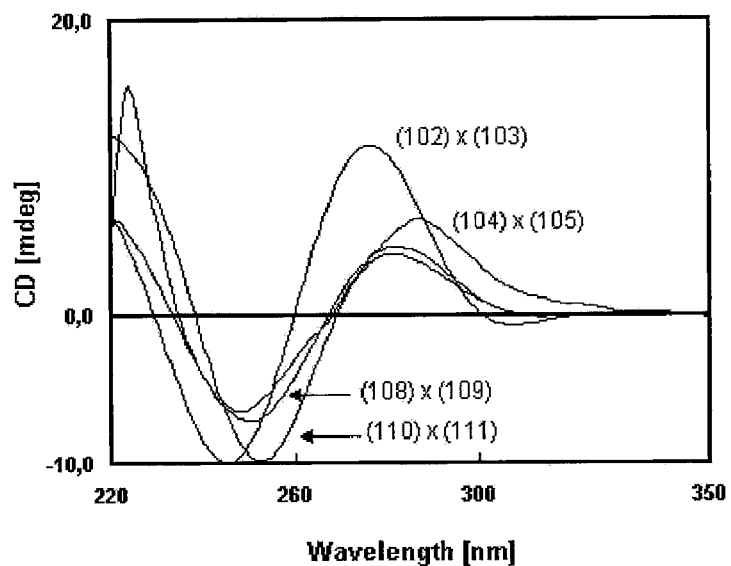
FIG. 3: Circular dichroism spectra of antiparallel DNA/DNA duplexes (FIG. 3a) and antiparallel DNA/RNA duplexes (FIG. 3b)

Yet, it has not been proven whether the $T_m$-value increases linearly with the number of incorporated 8-aza-7-deazapurine residues. In the case of compound 1 such a study has been undertaken, which showed that in poly(dA-dT) a linear relationship exists when the replacement of dA by the $n^2A_d$-residues did not exceed 50%. However, there was no further $T_m$-increase at higher $n^2A_d$-incorporation when the $T_m$-values were measured at low salt concentration. A similar observation as made on synthetic oligonucleotides was obtained for DNA of the cyano phage S-2L which contains $n^2A_d$ instead of dA [38]. In order to identify the helical structure of the duplexes CD-spectra of the duplexes 102•103 to 110•111 were measured [39]. The CD-spectra of all duplexes indicate a B-like DNA structure, with a positive Cotton effect around 270 nm to 290 nm and a negative lobe around 250 nm (see FIG. 3a).

Figure 3B:
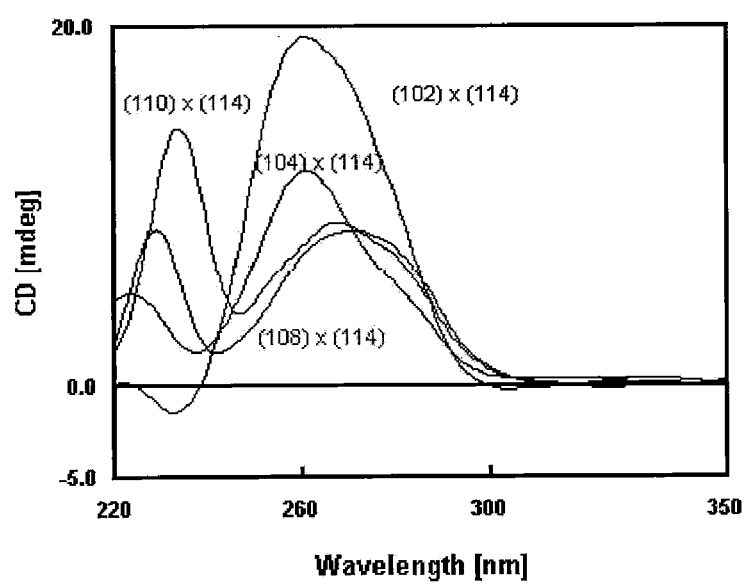

It has been reported that the purine nucleoside 1 forms more stable duplexes with complementary RNA than with DNA [40]. Therefore, oligonucleotides containing 1 or 2a,b were hybridized with a complementary oligoribonucleotide 114 (Table 5). According to Table 5 the DNA-RNA hybrid 104•114 shows a $T_m$-increase over that of the parent 102•114. The 8-aza-7-deazapurin-2,6-diamine residue 2a shows a similar effect as that of 1. An additional stabilization is observed when the bromo compound 2b was incorporated. All CD-spectra of the DNA-RNA hybrids (see FIG. 3b) adopt the form of an A-DNA.

Figure 4A:
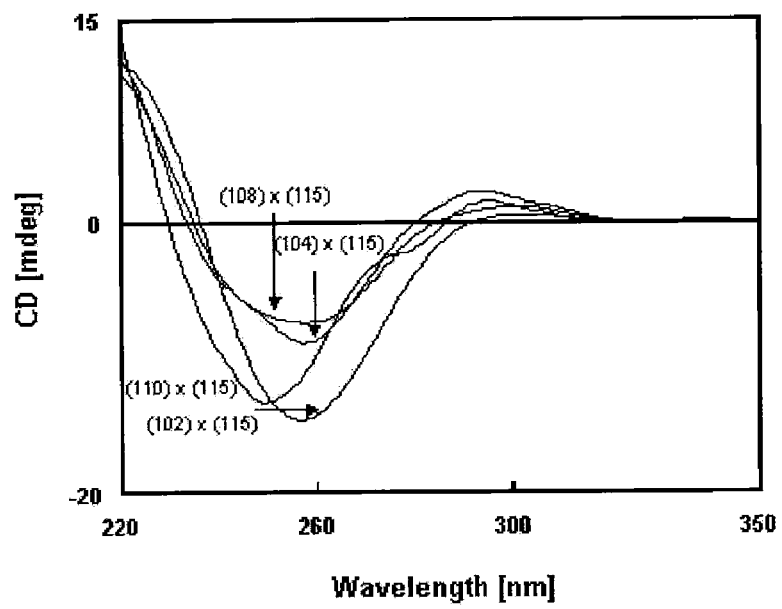
FIG. 4: Circular dichroism spectra of parallel DNA/DNA duplexes (FIG. 4a) and parallel DNA/RNA duplexes (FIG. 4b)
Figure 4B:
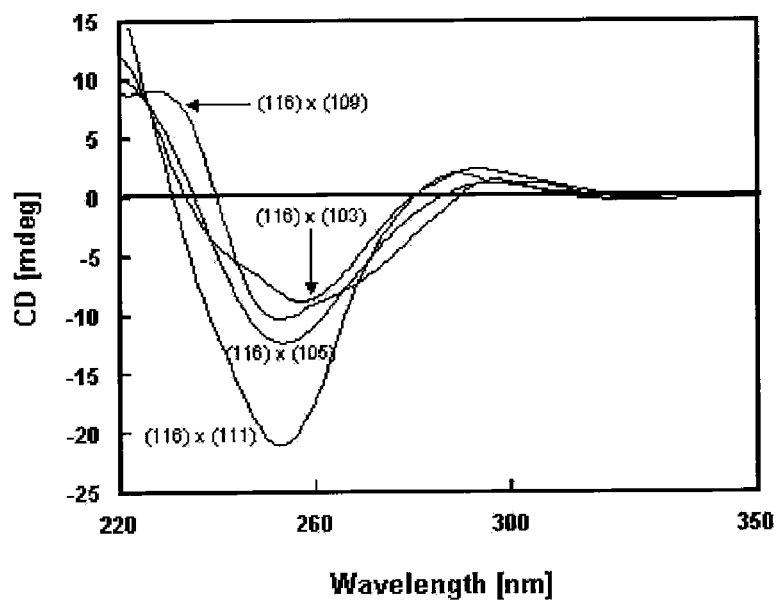

Finally, the base pairing properties of the nucleosides 1 and 2a,b were studied in parallel-stranded DNA (ps-DNA) [37], [42]. For this purpose it was necessary to exchange the dC-dG pair by a $m^5iC_d$-dG and/or dC-$iG_d$ pair. As standard duplexes the hybrids (102•115) or (116•103) were chosen. In both series of experiments the purin-2,6-diamine (1) destabilized the ps-hybrids (104•115 and 116•105). The nucleoside 2a already led to slightly more stable duplexes (see Table 6). As in the case of antiparallel DNA the bromo derivative 2b resulted in a significant increase of the $T_m$-value (110•115 and 116•111). The two sets of CD-spectra (FIG. 4a,b) of the ps-duplexes are rather different to those of aps-hybrids (see FIG. 4a).

From these results it is apparent that the 2-amino group causes destabilization in the series of purine compounds and reduces the stabilizing effect observed in aps-DNA significantly. This behavior is not surprising at it was already observed that mono-substituted purin-2-amine or 8-aza-7-deazapurin-2-amine have a rather unfavorable influence on the stability of the ps-DNA [36] [42].

TABLE 5

$T_m$ Value and Thermodynamic Data of RNA-DNA and DNA-DNA hybrids.[a]

| | SEQ ID NO: | $T_m$ [° C.] | ΔH° [kcal/mol] | ΔS° [cal/mol · K] | ΔG°$_{310}$ [kcal/mol] |
|---|---|---|---|---|---|
| 5'-d(TAG GTC AAT ACT) (102) · (114)<br>3'-(AUC CAG UUA UGA) | 2<br>12 | 45 | −92 | −264 | −10.2 |
| 5'-d(T1G GTC 11T 1CT) (104) · (114)<br>3'-(AUC CAG UUA UGA) | 4<br>12 | 48 | −60 | −162 | −11.0 |
| 5'-d(TAG GTC 2a2aT ACT) (108) · (114)<br>3'-(AUC CAG UUA UGA) | 8<br>12 | 48 | −89 | −263 | −11.0 |
| 5'-d(TAG GTC 2b2bT ACT) (110) · (114)<br>3'-(AUC CAG UUA UGA) | 10<br>12 | 53 | −93 | −258 | −12.4 |

[a] See Table 4.

TABLE 6

$T_m$ value, Thermodynamic Data of Parallel Stranded Oligonucleotides
Formed by Oligonucleotides Containing $iG_d$ and $m^5iC_d$.[a,b]

| | SEQ ID NO: | $T_m$ [° C.] | ΔH° [kcal/mol] | ΔS° [cal/mol · K] | ΔG°$_{310}$ [kcal/mol] |
|---|---|---|---|---|---|
| 5'-d(TAG GTC AAT ACT) (102) · (115) [37]<br>5'-d(ATiC iCAiG TTA TiGA) | 2<br>13 | 39 | −74 | −211 | −8.8 |
| 5'-d(T1G GTC 11T 1CT) (104) · (115)<br>5'-d(ATiC iCAiG TTA TiGA) | 4<br>13 | 36 | −76 | −200 | −7.9 |
| 5'-d(TAG GTC 2a2aT ACT) (108) · (115)<br>5'-d(ATiC iCAiG TTA TiGA) | 8<br>13 | 41 | −62 | −171 | −9.0 |
| 5'-d(TAG GTC 2b2bT ACT) (110) · (115)<br>5'-d(ATiC iCAiG TTA TiGA) | 10<br>13 | 45 | −67 | −184 | −10.2 |
| 5'-d(TiCA TAA iCTiG iGAT) (116) ·<br>(103) [37]<br>5'-d(AGT ATT GAC CTA) | 14<br><br>3 | 44 | −85 | −242 | −10.3 |
| 5'-d(TiCA TAA iCTiG iGAT) (116) · (105)<br>5'-d(AGT 1TT G1C CTA) | 14<br>5 | 39 | −61 | −170 | −8.4 |
| 5'-d(TiCA TAA iCTiG iGAT) (116) · (109)<br>5'-d(AGT 2aTT G2aC CTA) | 14<br>9 | 45 | −80 | −230 | −10.3 |
| 5'-d(TiCA TAA iCTiG iGAT) (116) · (111)<br>5'-d(AGT 2bTT G2bC CTA) | 14<br>11 | 48 | −68 | −186 | −10.9 |

[a]Measured at 260 nm in 1 M NaCl, 0.1 M l$_2$, 60 mM Na-cacodylate buffer, pH 7.0 with 5 + 5 µM oligomer concentration.
[b]d(iC) = $m^5iC_d$ = 2'-deoxy-5-methylisocytidine.

The two amino groups of the 8-aza-7-deazapurine nucleosides 2a,b can be protected with either benzoyl residues or dibutylaminomethylene groups without causing depurination problems during the acidic detritylation or the deprotection under standard conditions in ammonia. The problems of depurination and an extraordinary high stability of the 2-amino protecting groups of the purin-2,6-diamine nucleoside 1 is not observed.

1.3 Experimental Part

Monomers: General. See [2]. Flash chromatography (FC): 0.4 bar on silica gel 60H (Merck, Darmstadt, Germany). Thin-layer chromatography (TLC): Aluminium sheets silica gel 60 F$_{254}$ (0.2 mm, Merck, Germany). TLC Scanning: CS-930 TLC scanner (Shimadzu, Japan). Solvent systems for flash chromatography (FC) and TLC: CH$_2$Cl$_2$ MeOH 98:2 (A) CH$_2$Cl$_2$/MeOH 95:5 (B), CH$_2$Cl$_2$/MeOH 9:1(C), CH$_2$Cl$_2$/acetone 95:5 (D), CH$_2$Cl$_2$/acetone 9:1 (E), CH$_2$Cl$_2$/EtOAc 85:15 (F). M.p.: Büchi-SMP-20 apparatus (Büchi, Switzerland); uncorrected. NMR Spectra: Avance-DPX-250 and AMX-500 spectrometers (Bruker, Germany); δ values are in ppm downfield from internal SiMe$_4$ ($^1$H, $^{13}$C). Microanalyses were performed by Mikroanalytisches Labor Beller (Göttingen, Germany).

Oligonucleotides:

Synthesis and purification of Oligonucleotides 102-116. The synthesis was carried out on an automated DNA synthesizer (Applied Biosystems, model ABI 392-08 for phosphoramidite chemistry) in a 1 µmol scale with 3'-phosphoramidites of [(MeO)$_2$Tr]ib$^2$G$_d$, [(MeO)$_2$Tr]bz$^6$A$_d$, [(MeO)$_2$Tr] bz$^4$C$_d$ and [(MeO)$_2$Tr]T$_d$, together with the phosphoramidites of the derivatives 7b and 11b. The synthesis of the oligomers followed the regular protocol of the DNA synthesizer for phosphoramidites. After cleavage from the solid-support, the oligonucleotides were deprotected in 25% NH$_3$/H$_2$O (12-15 h at 60°). The purification of the 5'-(dimethoxytrityl)-oligomers were performed by OPC cartridges as well as by reversed-phase HPLC(RP-18). The following solvent gradient was used (A, MeCN; B, 0.1 M (Et$_3$NH)OAc (pH 7.0)/MeCN 95:5): 3 min 20% A in B, 12 min 15-40% A in B with a flow rate of 1.0 ml/min To remove the 4,4'-dimethoxytrityl residues they were treated with 2.5% CHCl$_2$COOH/CH$_2$Cl$_2$ for 5 min at r.t. The detritylated oligomers were purified by reversed-phase HPLC with the gradient: 20 min 0-20% A in B with a flow rate of 1 ml/min. The oligomers were desalted on a short column (RP-18, silica gel) using H$_2$O for the elution of the salt, while the oligomers were eluted with MeOH/H$_2$O 3:2. The oligomers were lyophilized on a Speed-Vac evaporator to yield colorless solids which were frozen at −24°.

TABLE 7

Molecular Masses M$^+$ of Oligonucleotides
12,13 and 18-21 determined by MALDI-TOF
Mass Spectroscopy

| Oligomer | SEQ ID NO: | M+ (calc.) | M+ (found) |
|---|---|---|---|
| 5'-d(TAG GTC AAT ACT) (102) | 2 | 3644.4 | 3645 |
| 5'-d(AGT ATT GAC CTA) (103) | 3 | 3644.4 | 3645 |
| 5'-d(TAG GTC 2a2aT ACT) (108) | 8 | 3674.4 | 3677 |
| 5'-d(AGT 2aTT G2aC CTA) (109) | 9 | 3674.4 | 3675 |
| 5'-d(TAG GTC 2b2bT ACT) (110) | 10 | 3832.5 | 3830 |
| 5'-d(AGT 2bTT G2bC CTA) (111) | 11 | 3832.5 | 3832 |

The MALDI-TOF-spectra were measured on a Biflex III by Dr. T. Wenzel (Broker Saxonia, Germany). Nucleoside-Composition Analysis. The analyses were performed as described in [37]. Extinction coefficients of the nucleoside constituents: $\epsilon_{260}$: dA 15400, dT 8800, dG 11700, dC 7600, iG$_d$ 7400, m$^5$iC$_d$ 6300, 2a 8800, 2b 8700. Snake-venom phosphodiesterase (EC 3.1.4.1., *Crotallus durissus*) and alkaline phosphatase (EC 3.1.3.1., *E. coli*) were obtained from Roche Diagnostics GmbH, Germany.

Determination of $T_m$ Values and Thermodynamic Data. Absorbance vs. temperature profiles were measured on a Cary-1/1E UV/VIS spectrometer (Varian, Australia) equipped with a Cary thermoelectrical controller. The $T_m$ values were determined in the reference cell with a Pt-100 resistor, and the thermodynamic data were calculated using the Meltwin 3.0 program [43].

Circular Dichroism Spectra. The CD-spectra were recorded with a Jasco-600 (Jasco, Japan) spectropolarimeter with thermostatically (Lauda-RCS-6 bath) controlled 1 cm cuvettes. UV-Spectra: 150-20 spectrometer (Hitachi, Japan).

3-Bromo-1-[2-deoxy-β-D-erythro-pentofuranosyl]-1H-pyrazolo[3,4-d]-pyrimidin-4,6-diamine (2b). A soln. of compd 4b [18] (1.0 g, 2.6 mmol) in aq. 25% NH$_3$ (80 ml) was heated at 70° for 4 d in a steel vessel. The solvent was evaporated, and the residue was dissolved in hot H$_2$O. Crystallization occurred upon cooling. Colorless needles (646 mg, 72%). M.p. 155°. TLC (C): R$_f$ 0.2. UV (MeOH): 260 (8700), 278 (9000). $^1$H-NMR ((D$_6$)DMSO): 2.16, 2.68 (2m, H$_2$—C(2')); 3.38, 3.48 (2m, H$_2$—C(5')); 3.77 (m, H—C(4')); 4.36 (m, H—C(3')); 4.72 (t, J=4.9, HO—C(55); 5.19 (d, J=4.1, HO—C(3')); 6.32 ('t', J=6.5, H—C(1')); 6.39 (s, NH$_2$); 6.77 (br, NH$_2$). Anal. calc. for C$_{10}$H$_{13}$BrN$_6$O$_3$ (345.2): C, 34.80; H, 3.80; N, 24.35. found: C, 34.97; H, 3.97; N, 24.21.

N$^4$,N$^6$-Bis(phenoxyacetyl)-1-[2-deoxy-β-D-erythro-pentofuranosyl]-1H-pyrazolo[3,4-d]-pyrimidin-4,6-diamine (5a). Compd. 2a [15] (1.5 g, 5.6 mmol) was dried by coevaporation with pyridine. The residue was dissolved in pyridine (25 ml) and trimethylsilyl chloride (3.3 ml, 26 mmol) was added at r.t while stirring. Stirring was continued for 15 min and a soln. of 2,4,5-trichlorophenyl phenoxyacetate (5.4 g, 16.4 mmol) [27] in pyridine (15 ml) was added in one portion. The reaction mixture was stirred for 16 h at 40°. It was cooled (ice bath) and H$_2$O (4.2 ml) was added. After 5 min, aq. 25% NH$_3$ (6 ml) was introduced, and the mixture was concentrated to dryness. The residue was applied FC (eluant: A→C) yielding a colorless foam (900 mg, 30%). TLC (C): R$_f$ 0.4. UV (MeOH): 266 (9100). $^1$H-NMR ((D$_6$)DMSO): 2.26, 2.82 (2m, H$_2$—C(2')); 3.34, 3.48 (2m, H$_2$—C(5')); 3.82 (m, H—C(4')); 4.44 (m, H—C(3')); 4.73 (t, J=5.5, HO—C(5')); 5.14 (s, OCH$_2$)); 5.17 (d, J=4.3, HO—C(3')); 6.60 ('t', J=6.3, H—C(1')); 6.92-7.32 (m, arom. H); 8.41 (s, H—C(3)); 10.77 (s, NH); 11.30 (s, NH). Anal. calc. for C$_{26}$H$_{26}$N$_6$O$_7$ (534.5): C, 58.42; H, 4.90; N, 15.72. found: C, 58.68; H, 4.78; N, 15.20.

N$^4$,N$^6$-Bis(phenoxyacetyl)-1-[2-deoxy-5-O-(4,4'-dimethoxytrityl)-β-D-erythro-pentofuranosyl]-1H-pyrazolo[3,4-d]-pyrimidin-4,6-diamine (6a). Compd. 5a (0.8 g, 1.5 mmol) was coevaporated twice with pyridine. The residue was dissolved in pyridine (2 ml) and 4,4'-dimethoxytrityl chloride (0.6 g, 1.77 mmol) was added. Stirring at r.t. was continued for 4 h than the soln. was diluted with MeOH (5 ml) and washed with 5% aq. sodium bicarbonate (3×20 ml). The organic layer was dried (Na$_2$SO$_4$) and concentrated to dryness. The residue was purified by FC (eluant: D→E) yielding a colorless foam (310 mg, 25%). TLC (E): R$_f$ 0.3. UV (MeOH): 266 (8900). $^1$H NMR: ((D$_6$)DMSO): 2.32, 2.81 (2m, H$_2$—C(2')); 2.99 (2m, H$_2$—C(5')); 3.67 (2s, OCH$_3$); 3.95 (m, H—C(4')); 4.53 (m, H—C(3')); 5.15 (s, OCH$_2$)); 5.33 (d, J=4.7, HO—C(3')); 6.62 ('t', J=6.3, H—C(1')); 6.69-7.31 (m, arom. H); 8.36 (s, H—C(3)); 10.83 (s, NH); 11.56 (s, NH). Anal. calc. for C$_{47}$H$_{44}$N$_6$O$_9$ (836.9): C, 67.45; H, 5.30; N, 10.04. found: C, 66.95; H, 5.41; N, 10.15.

N$^4$,N$^6$-Bis(phenoxyacetyl)-1-[2-deoxy-5-O-(4,4'-dimethoxytrityl)-β-D-erythro-pentofuranosyl]-1H-pyrazolo[3,4-d]-pyrimidin-4,6-diamine 3'-[(2-Cyanoethyl) N,N-Diisopropyl-phosphoramidite] (7a). To a soln. of compd. 7a (0.15 g, 0.18 mmol) in THF (0.5 ml), ($^i$Pr)$_2$EtN (0.12 ml, 0.71 mmol) and 2-cyanoethyl diisopropylphosphoramidochloridite (64 mg, 0.27 mmol) were added. Stirring under argon atmosphere at r.t. was continued for 30 min. Then, the mixture was diluted with CH$_2$Cl$_2$ (20 ml) and 5% aq. NaHCO$_3$. The mixture was extracted with CH$_2$Cl$_2$ (3×15 ml). The combined organic layers were dried (Na$_2$SO$_4$) and evaporated to give an oil. The residue was submitted to FC (eluant: F) yielding (80 mg, 43%) of a colorless foam. TLC (F): R$_f$ 0.8. $^{31}$P-NMR (CDCl$_3$): 149.2, 149.4.

N$^4$,N$^6$-Bis(benzoyl)-1-[2-deoxy-β-D-erythro-pentofuranosyl]-1H-pyrazolo[3,4-d]-pyrimidin-4,6-diamine (5b). Compd. 2a [17] (1 g, 3.8 mmol) was coevaporated twice with toluene and dissolved in pyridine (40 ml) and TMS-Cl (4.0 g, 36.8 mmol). The reaction mixture was stirred under argon atmosphere, cooled to 0° and PhCOCl (6.6 ml, 57 mmol) were added drop-wise to the soln. over a period of 30 min. After stirring overnight at r.t. the mixture was diluted in EtOAc (200 ml) and washed with a sat. sodium bicarbonate soln. (200 ml) and ice cold H$_2$O (200 ml). The aq. layer was extracted with EtOAc (2×400 ml). The combined org. layers were evaporated to dryness and dissolved in THF/MeOH/H$_2$O 5:4:1 (250 ml). The dark orange soln. was cooled to 0°, and 2 N NaOH (25 ml) was added while stirring was continued for 40 min. The residue was purified by FC (eluant: A→B) yielding 1.1 g (61%) of an amorphous solid. TLC (B): R$_f$ 0.3. UV (MeOH): 245 (16400), 274 (15200). $^1$H-NMR ((D$_6$)DMSO): 2.13, 2.67 (2m, H$_2$—C(2')); 3.38, 3.52 (2m, H$_2$—C(5')); 3.84 (m, H—C(4')); 4.46 (m, H—C(3')); 4.72 (t, J=5.7, HO—C(5')); 5.29 (d, J=4.4, HO—C(3')); 6.66 ('t', J=6.5, H—C(1')); 7.51-8.11 (m, arom. H); 8.40 (s, H—C3); 10.95 (s, NH); 11.49 (s, NH). Anal. calc. for C$_{24}$H$_{22}$N$_6$O$_5$ (474.5): C, 60.75; H, 4.67; N, 17.71. found: C, 61.03; H, 4.70; N, 17.58.

N$^4$,N$^6$-Bis(benzoyl)-1-[2-deoxy-5-O-(4,4'-dimethoxytrityl)-β-D-erythro-pentofuranosyl]-1H-pyrazolo[3,4-d]-pyrimidin-4,6-diamine (6a). As described for 6a with 5a (500 mg, 1.05 mmol) and DMT-Cl (460 mg, 1.35 mmol) in pyridine (3 ml). The residue was purified by FC (eluant: D→E) yielding 400 mg (49%) of a colorless foam. TLC (E): R$_f$ 0.4. UV (MeOH): 244 (16400), 275 (15200). $^1$H-NMR ((D$_6$)DMSO): 2.35, 2.67 (2m, H$_2$—C(2'); 3.07, 3.10 (2m, H$_2$—C(5'); 3.68, 3.69 (2s, OCH$_3$); 3.97 (m, H—C(4')); 4.56 (m, H—C(3')); 5.35 (d, J=4.8, HO—C(3')); 6.72-8.11 (m, arom. H); 8.36 (s, H—C(3)); 11.01 (s, NH); 11.54 (s, NH).

N$^4$,N$^6$-Bis(benzoyl)-1-[2-deoxy-5-O-(4,4'-dimethoxytrityl)-β-D-erythro-pentofuranosyl]-1H-pyrazolo[3,4-d]-pyrimidin-4,6-diamine 3'-[(2-Cyanoethyl) N,N-Diisopropylphosphoramidite] (7b). As described for 7a with 6b (110 mg, 0.14 mmol), ($^i$Pr)$_2$EtN (75 µl, 0.43 mmol) and 2-cyanoethyl diisopropylphosphoramidochloridite (38 µl, 0.17 mmol) in THF (3 ml) at 30°. The oily residue was submitted to FC (eluant: F) yielding 92 mg (67%) of a colorless foam. TLC (F): R$_f$ 0.8. $^{31}$P-NMR (CDCl$_3$): 149.82, 149.63.

N$^4$,N$^6$-Bis((di-n-butylamino)methylene)-1-[2-deoxy-β-D-erythro-pentofuranosyl]-1H-pyrazolo[3,4-d]-pyrimidin-4,6-diamine (8a). To a stirred suspension of 2a (300 mg, 1.13 mmol) in MeOH (5 ml) N,N-di-n-butylformamide dimethyl acetal (790 µl, 3.39 mmol) was added. Stirring was continued for 2 h at 40°. The reaction mixture was evaporated to dryness and the residue adsorbed on silica gel. FC (eluant: A→B) afforded two main products. From the faster migrating zone a colorless foam of 8a (330 mg, 53%) was isolated. TLC (B): R$_f$ 0.4. UV (MeOH): 235 (22800), 274 (13800), 322 (25 700). $^1$H-NMR (CDCl$_3$): 0.87-0.95 (m, CH$_2$CH$_3$); 1.26-1.38 (m, CH$_2$CH$_3$); 1.57-1.60 (m, CH$_2$CH$_2$); 2.42-2.92 (m, H$_2$—C(2')); 3.26-3.72 (2m, H$_2$—C(5'), NCH$_2$); 3.88 (m, H—C(4')); 4.39 (m, H—C(3')); 4.78 (t, J=5.8, HO—C(55); 5.21 (d, J=4.8, HO—C(3')); 6.55 ('t', J=6.9, H—C(1')); 7.93 (s, H—C (30; 8.66 (s, N═CH); 8.88 (s, N═CH). Anal. calc. for C$_{28}$H$_{49}$N$_8$O$_3$ (544.7): C, 61.74; H, 8.88; N, 20.57. found: C, 61.71; H, 8.91; N, 20.57. From the slower migrating zone 1-[2-deoxy-β-D-erythro-pentofuranosyl]-N$^6$—((di-n-butylamino)-methylene)-1H-pyrazolo[3,4-d]-pyrimidin-4,6-diamine (9a) (80 mg, 17%) was obtained. TLC (B): R$_f$ 0.3. UV (MeOH): 235 (23000), 275 (14900), 320 (22100). $^1$H-NMR ((D$_6$)DMSO): 0.88-0.95 (m, CH$_2$CH$_3$); 1.27-1.36 (m, CH$_2$CH$_3$); 1.53-1.62 (m, CH$_2$CH$_2$); 2.21 (m, H—C(2')); 2.91 (m, H—C(2')); 3.38-3.59 (2m, H$_2$—C(5'), NCH$_2$); 3.79 (m, H—C(4')); 4.40 (m, H—C(3')); 4.78 (t, J=5.8, HO—C(5')); 5.19 (d, J=4.4, HO—C(3')); 6.36 (s, NH$_2$); 6.40 ('t', J=6.5, H—C(1')); 7.77 (s, H—C(3')); 8.69 (s, N=CH). Anal. calc. for C$_{19}$H$_{31}$N$_7$O$_3$ (405.5): C, 56.28; H, 7.71; N, 24.18. found: C, 55.98; H, 7.52; N, 24.05.

N$^4$,N$^6$-Bis((di-n-butylamino)methylene)-3-bromo-1-[2-deoxy-β-D-erythro-pentofuranosyl]-1H-pyrazolo[3,4-d]-pyrimidin-4,6-diamine (8b). As described for 8a, with 2b (350 mg, 1 mmol) and N,N-di-n-butylformamide dimethyl acetal (720 μl, 3.1 mmol) in MeOH (7 ml) for 2 h at 40°. After FC (eluant: A→B) two main products were isolated. The faster migrating zone gave 8b as a foam (310 mg, 50%). TLC(B): R$_f$ 0.3. UV (MeOH): 235 (22500), 275 (14500), 320 (22100). $^1$H-NMR ((D$_6$)DMSO): 0.94-0.99 (m, CH$_2$CH$_3$); 1.32-1.44 (m, CH$_2$CH$_3$); 1.59-1.73 (m, CH$_2$CH$_2$); 2.21 (m, H—C(2')); 2.91 (m, H—C(2')); 3.32-3.78 (2m, H$_2$—C(5'), NCH$_2$); 3.89 (m, H—C(4')); 4.40 (m, H—C(3')); 4.78 (t, J=5.8, HO—C(5')); 5.19 (d, J=4.4, HO—C(3')); 6.81 ('t', J=6.5, H—C(1')); 8.69 (s, N=CH); 8.94 (s, N=CH). Anal. calc. for C$_{28}$H$_{47}$BrN$_8$O$_3$ (623.6): C, 53.93; H, 7.60; N, 17.97. found: C, 54.01; H, 7.52; N, 18.05. The slower zone furnished 3-bromo-1-[2-deoxy-β-D-erythro-pentofuranosyl]-N$^6$-((di-n-butylamino)methylene)-1H-pyrazolo[3,4-d]-pyrimidin-4,6-diamine (9b) (75 mg, 16%). TLC(B): R$_f$ 0.3. UV (MeOH): 236 (21600), 276 (14000), 320 (21900). $^1$H-NMR ((D6)DMSO): 0.90-0.96 (m, CH$_2$CH$_3$); 1.30-1.39 (m, CH$_2$CH$_3$); 1.59-1.73 (m, CH$_2$CH$_2$); 2.23 (m, H—C(2')); 2.89 (m, H—C(2')); 3.35-3.78 (2m, H$_2$—C(5'), NCH$_2$); 3.84 (m, H—C(4')); 4.43 (m, H—C(3')); 4.80 (t, J=5.7, HO—C(5')); 5.23 (d, J=4.6, HO—C(3')); 6.40 (s, NH$_2$); 6.81 J=6.4, H—C(1')); 8.65 (s, N=CH). Anal. calc. for C$_{19}$H$_{30}$BrN$_7$O$_3$ (484.4): C, 47.11; H, 6.24; N, 20.24. found: C, 47.23; H, 6.52; N, 20.35.

1-[2-Deoxy-5-O-(4,4'-dimethoxytrityl)-13-D-erythro-pentofuranosyl]-N$^4$-((di-n-butylamino)methylene)-N$^6$-formyl-1H-pyrazolo[3,4-d]-pyrimidin-4,6-diamine (10a). As described for 6a with 8a (80 mg, 0.15 mmol), DMT-Cl (60 mg, 0.18 mmol) in pyridine (0.5 ml). The residue was purified by FC (eluant: D→E) yielding 85 mg (77%) of a colorless foam. TLC (E): R$_f$ 0.3. UV (MeOH): 235 (22800), 276 (20000), 320 (24800). $^1$H-NMR (CDCl$_3$): 0.98-1.05 (m, CH$_2$CH$_3$); 1.14-1.48 (m, CH$_2$CH$_3$); 1.65-1.78 (m, CH$_2$CH$_2$); 2.42-2.92 (m, H$_2$—C(2')); 3.35-3.70 (2m, H$_2$—C(5'), NCH$_2$); 3.71 (s, OCH$_3$); 4.06 (m, H—C(4')); 4.39 (m, H—C(3')); 5.21 (d, J=4.8, HO—C(3')); 6.55 J=6.6, H—C(1')); 6.76-7.96 (m, arom. H); 7.94 (d, J=10.5, NH); 7.96 (s, H—C(3')); 8.81 (s, N=CH); 9.57 (d, J=10.5, CHO). Anal. calc. for C$_{41}$H$_{49}$N$_7$O$_6$ (735.9): C, 66.92; H, 6.71; N, 13.32. found: C, 66.85; H, 6.56; N, 13.40.

3-Bromo-1-[2-deoxy-5-O-(4,4'-dimethoxytrityl)-β-D-erythro-pentofuranosyl]-N$^4$-((di-n-butylamino)methylene)-N$^6$-formyl-1H-pyrazolo[3,4-d]-pyrimidin-4,6-diamine (10b). As described for 6a with 8b (310 mg, 0.5 mmol), DMT-Cl (202 mg, 0.6 mmol) in pyridine (2 ml). The residue was purified twice by FC (eluant D→E) yielding 250 mg (61%) of a colorless foam. TLC (E): R$_f$ 0.3. UV (MeOH): 235 (22900), 276 (21100), 320 (25300). $^1$H-NMR (D$_6$)DMSO): 0.90-0.96 (m, CH$_2$CH$_3$); 1.28-1.37 (m, CH$_2$CH$_3$); 1.61-1.68 (m, CH$_2$CH$_2$); 2.21 (m, H—C(2')); 2.91 (m, H—C(2')); 3.03 (2m, H$_2$—C(5')); 3.35-3.52 (m, NCH$_2$); 3.69 (s, OCH$_3$); 3.90 (m, H—C(4')); 4.48 (m, H—C(3')); 5.32 (d, J=4.7, HO—C(3')); 6.46 ('t', J=6.2, H—C(1')); 6.73-7.31 (m, arom. H); 8.99 (s, N=CH); 9.56 (d, J=9.89, NH); 10.77 (d, J=9.88, CHO). Anal. calc. for C$_{41}$H$_{48}$BrN$_7$O$_6$ (814.8): C, 60.44; H, 5.94; N, 12.03. found: C, 60.36; H, 5.73; N, 11.85.

1-[2-Deoxy-5-O-(4,4'-dimethoxytrityl)-β-D-erythro-pentofuranosyl]-N$^4$-((di-n-butylamino)methylene)-N$^6$-formyl-1H-pyrazolo[3,4-d]-pyrimidin-4,6-diamine 3'-[(2-Cyanoethyl) N,N-Diisopropylphosphoramidite] (11a). As described for 7a with 10a (110 mg, 0.15 mmol), ($^i$Pr)$_2$EtN (78 μl, 45 mmol) and 2-cyanoethyl diisopropylphosphoramidochloridite (47 μl, 0.2 mmol) in THF (2 ml). The oily residue was submitted to FC (eluant: F) yielding 75 mg (53%) of a colorless foam. TLC (F): R$_f$ 0.8. $^{31}$P-NMR (CDCl$_3$): 149.58, 149.52.

3-Bromo-1-[2-deoxy-5-O-(4,4'-dimethoxytrityl)-β-D-erythro-pentofuranosyl]-N$^4$-((di-n-butylamino)methylene)-N$^6$-formyl-1H-pyrazolo[3,4-d]-pyrimidin-4,6-diamine 3'-[(2-Cyanoethyl) N,N-Diisopropylphosphoramidite] (11b). As described for 7a with 10b (90 mg, 0.11 mmol), ($^i$Pr)$_2$EtN (63 μl, 0.36 mmol) and 2-cyanoethyl diisopropylphosphoramido-chloridite (31 μl, 0.14 mmol) in THF (1 ml). The oily residue was submitted to FC (eluant: F) yielding 80 mg (72%) of a colorless foam. TLC (F): R$_f$ 0.8. $^{31}$P-NMR (CDCl$_3$): 149.58, 149.53.

Example 2

Synthesis of the 7-Iodo-Derivatives

Oligonucleotides were synthesized containing halogenated "purine" and pyrimidine bases. Bromo and iodo substituents were introduced into the 7-position of 8-aza-7-deazapurin-2,6-diamine (2b, c) or into the 5-position of uracil residues (3b, c). Phosphoramidites were synthesized using the isobutyryl-residue for the protection of 2b and the benzoyl group for 2c. Duplexes containing the residues 2b or 2c gave always higher T$_m$ values than those of the non-modified counterparts containing 2'-deoxyadenosine, the purin-2,6-diamine 2'-deoxyribonucleoside (1) or 2a at the same positions. Six 2b-residues replacing dA in the duplex 5'-d(TAGGT-CAATACT) (102) (SEQ ID NO: 2)•5'-d(AGTATTGACCTA) (103) (SEQ ID NO: 3) raised the T$_m$-value from 48° to 75° (4.5° per modification). Contrary to this, incorporation of the 5-halogenated 2'-deoxyuridines 3b or 3c into oligonucleotide duplexes showed very little influence on the thermal stability, regardless which "purine" nucleoside is located opposite to them. The positive effects on the thermal stability of duplexes observed in DNA were also found in DNA-RNA hybrids or DNA with parallel chain orientation.

The following data compare the effects of halogen substituents such as bromine and iodine introduced into the 7-position of 8-aza-7-deazapurin-2,6-diamine 2'-deoxyribonucleosides 2b, c and the 2'-deoxyuridine derivatives 3b, c (purine numbering is used; see Scheme 6). These nucleosides will be incorporated into various positions of duplex DNA, and the number of incorporations will be increased, stepwise. As the halogen substituents are directed into the major groove, in both the series, the "purine" and pyrimidine nucleosides, it was of interest to quantify the effects. Furthermore, the effect of multiple incorporations will be investigated as it is known from other duplex-stabilizing nucleosides, that the stabilizing effects level off with an increasing number of modified nucleoside incorporations (C. Bailly, M. J. Waring, Nucleic Acids Res. 1998, 26, 4309 and references therein; J. Sági, E. Szakonyi, M. Vorlickova, J. Kypr, J. Biomolec. Struct. Dyn. 1996, 13, 1035.). Oligonucleotide duplexes incorporating 7-halogenated 7-deazapurines (=pyrrolo[2,3-d]pyrimidines) show differences in the series of 7-iodo and 7-bromo compounds (F. Seela, M. Zulauf, Chem. Eur. J. 1998, 4, 1781), which result from the spatial requirements of the halogens (van der Waals radii: Br=1.85 Å; I=1.98 Å (A. Bondi, J. Phys. Chem. 1964, 68, 441) and/or from the more hydrophobic character of the iodo substituents compared to the bromo residues. Thus, the 7-iodo derivative of the 8-aza-7-deazapurin-2,6-diamine nucleoside (2c) was synthesized, converted into a phosphoramidite, and a number of oligonucleotides were synthesized containing the 7-iodinated 8-aza-7-deazapurine-2,6-diamine nucleoside 2c. A comparison of the thermal stability of these duplexes will illustrate the striking differences in duplex stabilization among halogens introduced into pyrimidine or 8-aza-7-deazapurine residues located in a similar environment of the major groove of a B-DNA.

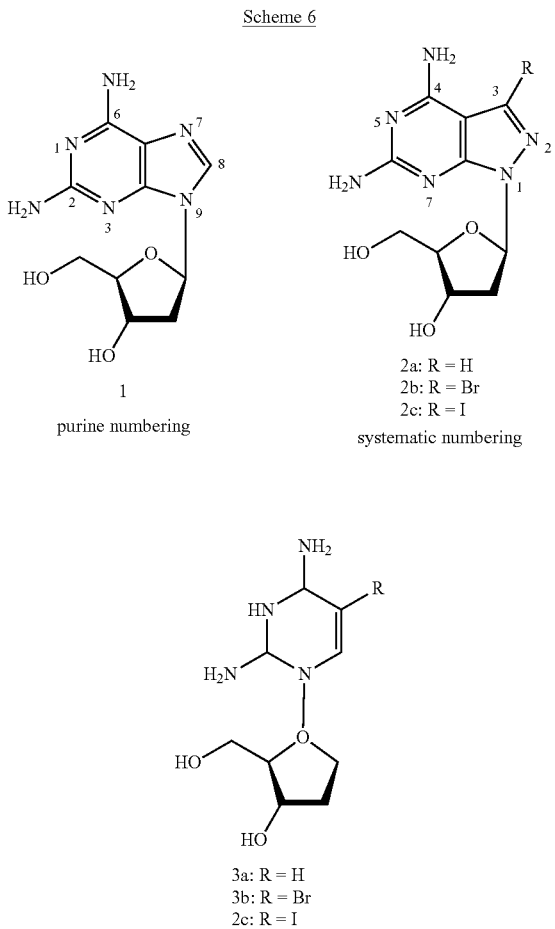

Scheme 6

2a: R = H
2b: R = Br
2c: R = I 1
purine numbering systematic numbering

3a: R = H
3b: R = Br
2c: R = I

2.1. Synthesis and Properties of Monomers

Figures 5A, 5B:
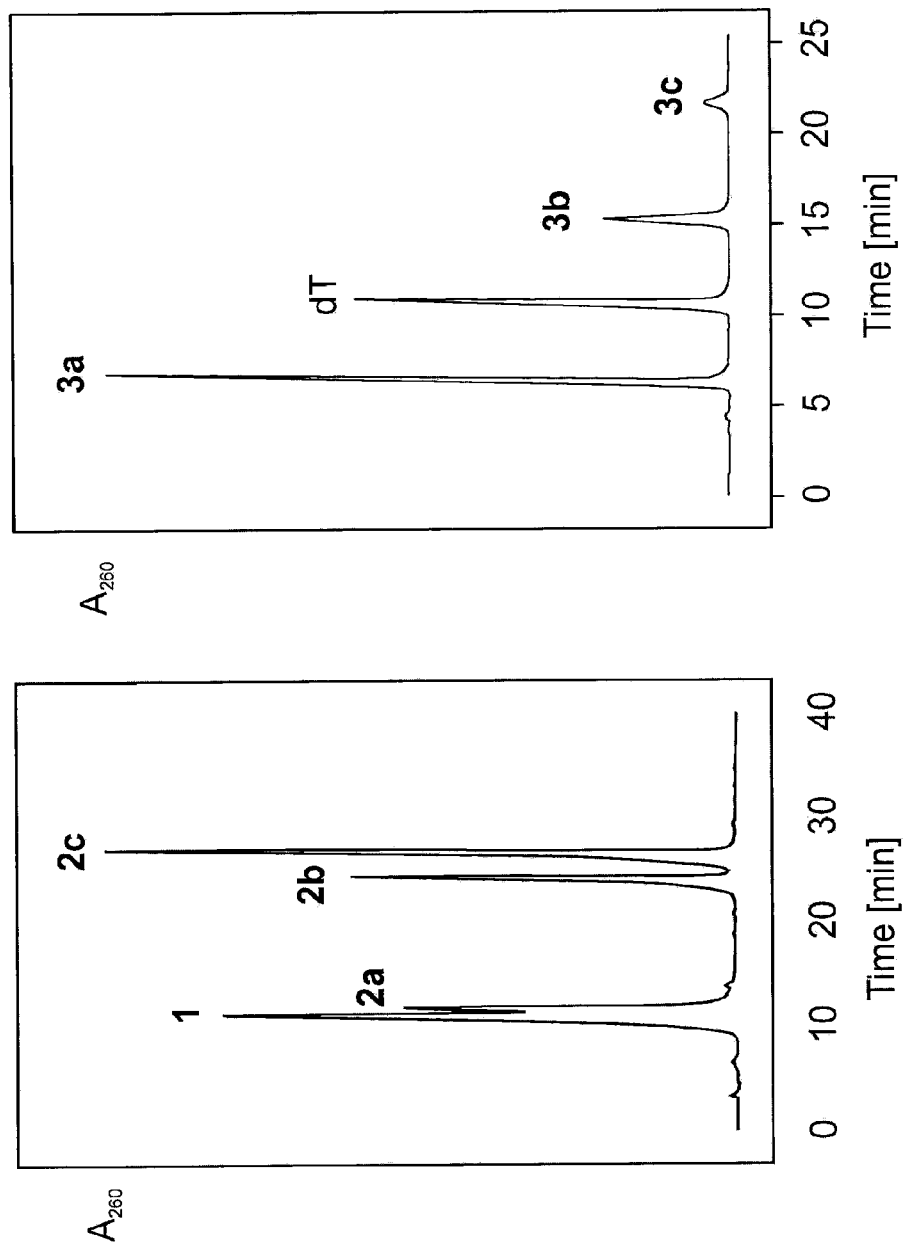
FIG. 5. HPLC profiles of the nucleosides 1,2a-c (a) and 3a-c and dT (b). The mixtures of the nucleosides were analyzed on reversed-phase HPLC at 260 nm (RP-18, gradient: 0-30 min in 0.1M (Et$_3$NH)OAc (pH7.0)/MeCN (95:5), 0.7 ml/min). HPLC profile of oligonucleotides 100 (c) and 304 (d) after enzymatic hydrolysis with snake-venom phosphodiesterase followed by alkaline phosphatase in 0.1 M Tris-HCl buffer (pH 83) at 37°. HPLC was performed on a RP-18 column (200×10 mm), 0-30 min in 0.1 M (Et$_3$NH)OAc (pH 7.0)/MeCN (95:5), 0.7 ml/min. Peak detection: 260 nm.

The 7-iodinated 8-aza-7-deazapurin-2,6-diamine 2'-deoxyribonucleoside 2c was prepared from the 6-isopropoxy compound 4 (F. Seela, G. Becher, *Synthesis* 1998, 2, 207) upon treatment with 25% aq. NH$_3$ at 70° C. for 4 days in an autoclave. The halogenated nucleosides 2a, b F. (Seela, G. Becher, *Synthesis* 1998, 2, 207) as well as the 2'-deoxyuridine derivatives 3a-c have been described elsewhere (J. Asakua, M. J. Robins, *J. Org. Chem.* 1990, 55, 4928). The halogen substituents change the mobility of the nucleosides on an RP-HPLC column with the iodinated 2c and 3c as the slowest migrating compounds (FIG. 5a, b). The retention times refer to the hydrophobic character of the nucleosides; the data were used later for the composition analysis of the base-modified oligonucleotides.

| Data of the Iodo compound - Table 8. Half-life Values (τ) of 2c at 25°. | | |
|---|---|---|
| Compound | τ [min]$^a$) | λ(nm) |
| I$^7$NH$_2$$^2$c$^7$z$^8$A$_d$ (2c) | stable$^b$) | 242 |
| I$^7$NH$_2$$^2$c$^7$z$^8$A$_d$ (2c) | 61$^c$) | 242 |

$^a$)Measured in 0.5 N HCl.
$^b$)Within 3 h.
$^c$)Measured in 2 N HCl.

The nucleobases of the modified nucleosides 2a-c and 3a-c influence the N↔S pseudorotational equilibrium of the sugar moiety. This affects the conformation of the sugar phosphate backbone of DNA. For this reason the $^1$H NMR spectra of the pyrazolo[3,4-d]pyrimidine nucleoside 2c as well as of the pyrimidine nucleosides 3a-c were measured in D$_2$O and $^3$J[$^1$H$^1$H] NMR coupling constants were determined. The conformational analysis was performed on the basis of $^3$J [$^1$H,$^1$H] couplings using the program *PSEUROT* (Van J. Wijk, C. Altona, 'PSEUROT 6.2—A Program for the Conformational Analysis of the Five-Membered Rings', University of Leiden, July 1993) According to Table 9 the 8-aza-7-deazapurin-2,6-diamine nucleoside 2a shows a higher N-conformer population than the corresponding purine nucleoside 1. The conformation around the C(4')—C(5') bond indicates that the 8-aza-7-deazapurin-2,6-diamine nucleoside 2c as the 8-aza-7-deaza-2'-deoxy-guanosines (F. Seela, G. Becher, H. Rosemeyer, H. Reuter, G. Kastner, 1. A. Mikhailopulo, *Helv. Chim. Acta* 1999, 82, 105) prefers the γ'-(–sc)-rotamer population, while for the regular purine nucleosides the γ$^{(+)g}$-(+sc)- or the γ$^{-)g}$-(ap)-conformation is predominant (G. Blackburn, M. J. Gait, 'Nucleic Acids in Chemistry and Biology', IRL Press, Oxford University Press 1990, p. 28) The conformation of the sugar moieties of the pyrimidine nucleosides 3a-c is also influenced by the substitution at the 5-position (Table 9). The main change is observed between 3a without a 5-substituent and the derivatives 3b, c with Me or halogen substituents.

TABLE 9

$^3$J (H, H) Coupling Constants of the Sugar Moieties and N/S-Conformer Populations of the 2'-Deoxyribonucleosides 1-3 at 303 K$^a$)

| | $^3$J$_{H,H}$/Hz | | | | | | | Conformation | | | | |
|---|---|---|---|---|---|---|---|---|---|---|---|---|
| | 1',2' | 1',2'' | 2',3' | 2'',3' | 3',4' | 4',5' | 4',5'' | % N | % S | γ$^{(+)g}$ | γ$^t$ | γ$^{(-)g}$ |
| 1 | 7.30 | 6.10 | 7.00 | 3.10 | 3.40 | 3.20 | 4.30 | 31 | 69 | 62 | 25 | 13 |
| 2a | 6.60 | 6.80 | 6.90 | 3.70 | 3.60 | 4.00 | 5.80 | 37 | 63 | 36 | 42 | 22 |
| 2c | 6.60 | 6.70 | 6.85 | 3.90 | 3.85 | 4.30 | 5.90 | 38 | 62 | 31 | 43 | 26 |
| dT[16] | — | — | — | — | — | — | — | 36 | 64 | — | — | — |
| 3a | 6.70 | 6.60 | 6.50 | 4.30 | 4.10 | 3.60 | 5.20 | 30 | 70 | 47 | 35 | 18 |

TABLE 9-continued $^3$J (H, H) Coupling Constants of the Sugar Moieties and N/S-Conformer Populations of the 2'-Deoxyribonucleosides 1-3 at 303 K$^a$)

| | $^3J_{H,H}$/Hz | | | | | | | Conformation | | | | |
|---|---|---|---|---|---|---|---|---|---|---|---|---|
| | 1',2' | 1',2" | 2',3' | 2",3' | 3',4' | 4',5' | 4',5" | % N | % S | $\gamma^{(+)g}$ | $\gamma^t$ | $\gamma^{(-)g}$ |
| 3b | 6.45 | 6.50 | 6.50 | 4.70 | 4.50 | 3.40 | 4.70 | 34 | 66 | 55 | 30 | 15 |
| 3c | 6.50 | 6.50 | 6.50 | 4.50 | 4.40 | 3.40 | 4.80 | 33 | 67 | 54 | 31 | 15 |

$^a$) Solvent D$_2$O; r.m.s. < 0.4 Hz; |ΔJ$_{max}$| < 0.4 Hz.
[16] C. Thibaudeau, J. Plavec, J. Chattopadhyaya, J. Org. Chem. 1996, 61, 266.

As the reactivity of the amino groups of the nucleoside 2b is rather different to 1, various residues were studied for the base protection. Earlier, the nucleoside 2b was protected with N,N-di-(n-butyl)formamidine (dnb) residue. Now, the isobutyryl group was introduced employing the protocol of transient protection (2b→13a) (G. S. Ti, B. L. Gaffney, R. A. Jones, *J. Am. Chem. Soc.* 1982, 104, 1316) As a side product the mono-protected nucleoside 14 was isolated (22%). The formation of mono-acylated compounds has been observed in the case of other 2,6-diaminopurine nucleosides (I. Luyten, A. V. Aerschot, J. Rozenski, R. Busson, and P. Herdewijn, Nucleosides Nucleotides 1997, 16, 1649) When performing the alkaline hydrolysis of compounds 13a or 14 in 25% aq. NH$_3$ at 40°, a fast deprotection was observed (See Scheme 7). The half-life for 13a and 14 were determined and found to be 4.5 min and 20.5 min, respectively. It indicates that this protecting group is appropriate for the solid-phase oligonucleotide synthesis. For the protection of the iodo nucleoside 2c the transient protection protocol was used as in 2b, but in this case a benzoyl group was chosen (2c→13b). The time for complete deprotection of 13b (25% aq. NH$_3$, 40° C., HPLC-monitoring at 260 nm) was 450 min. A half-life was not determined because of the step-wise reaction.

The base-protected nucleosides 13a, b as well as the pyrimidine nucleosides 3a-c were converted into the DMT-derivatives 15a, b, and 17a-c using standard reaction conditions (Y. S. Sanghvi, G. D. Hoke, S. M. Freier, M. G. Zounes, C. Gonzalez, L. Cummins, H. Sasmor, P. D. Cook, *Nucleic Acids Res.* 1993, 21, 3197) Phosphitylation of the DMT-derivatives 15a, b was performed in THF in the presence of 2-cyanoethyl diisopropylphosphoramidochloridite furnishing the phosphoramidites 16a, b (Scheme 7); the pyrimidine building blocks 18a-c were prepared from 17a-c in dichloromethane (Y. S. Sanghvi, G. D. Hoke, S. M. Freier, M. C. Zounes, C. Gonzalez, L. Cummins, H. Sasmor, P. D. Cook, *Nucleic Acids Res.* 1993, 21, 3197) These phosphoramidites (16a, b and 18a-c) were employed in solid-phase oligonucleotide synthesis. All compounds were characterized by $^1$H-, $^{13}$C-, and $^{31}$P-NMR spectra and by elemental analysis (Table 10). Table 11 summarizes the $^{13}$C NMR data of 8-aza-7-deazapurine as well as those of pyrimidine nucleosides. The assignment was made according to gated-decoupled spectra. The NMR data of 3a-c were included as a search of the literature gave little information on that matter.

Scheme 7

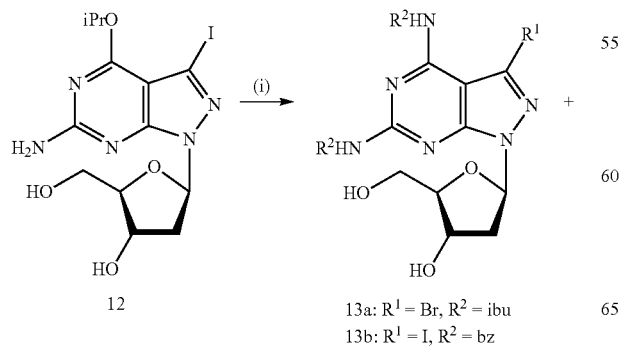

12

13a: R$^1$ = Br, R$^2$ = ibu
13b: R$^1$ = I, R$^2$ = bz

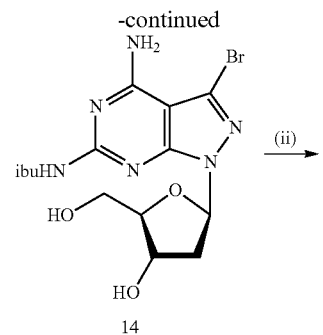

14

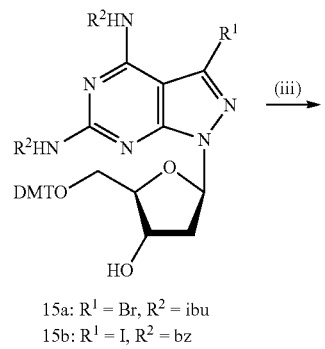

15a: R$^1$ = Br, R$^2$ = ibu
15b: R$^1$ = I, R$^2$ = bz

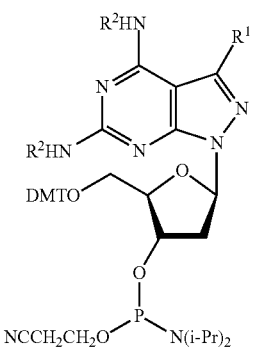

16a: R$^1$ = Br, R$^2$ = ibu(=8a)
16b: R$^1$ = I, R$^2$ = bz

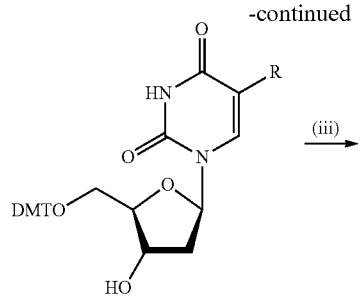

17a: R = H
17b: R = Br
17c: R = I

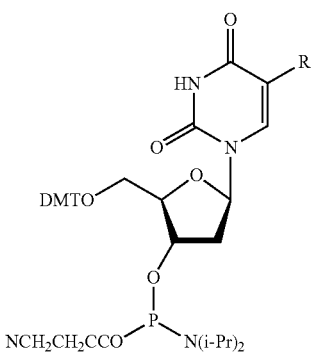

18a: R = H
18b: R = Br
18c: R = I (i)13a: Me₃SiCl, pyridine, isobutyric anhydride, r.t., 4 h; 13b: Me₃SiCl, pyridine, benzoyl chloride, r.t., 24 h. (ii) (MeO)₂TrCl, pyridine, r.t., 4 h; (iii) 2-cyanoethyl diisopropylphosphoramidochloridite, CH₂Cl₂, r.t., 30 min.

2.2. Oligonucleotides 2.2.1 Synthesis and Characterization

Figure 5D:
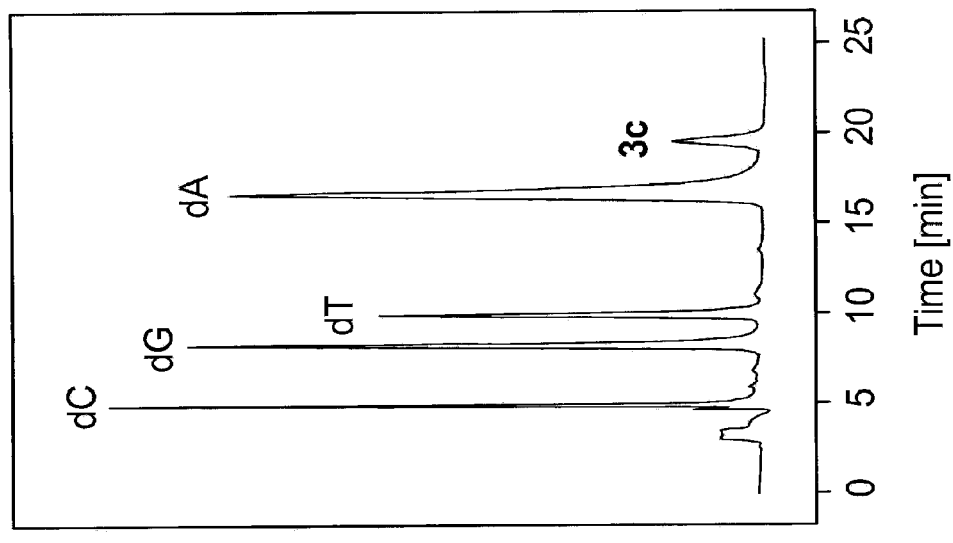
Figure 5C:
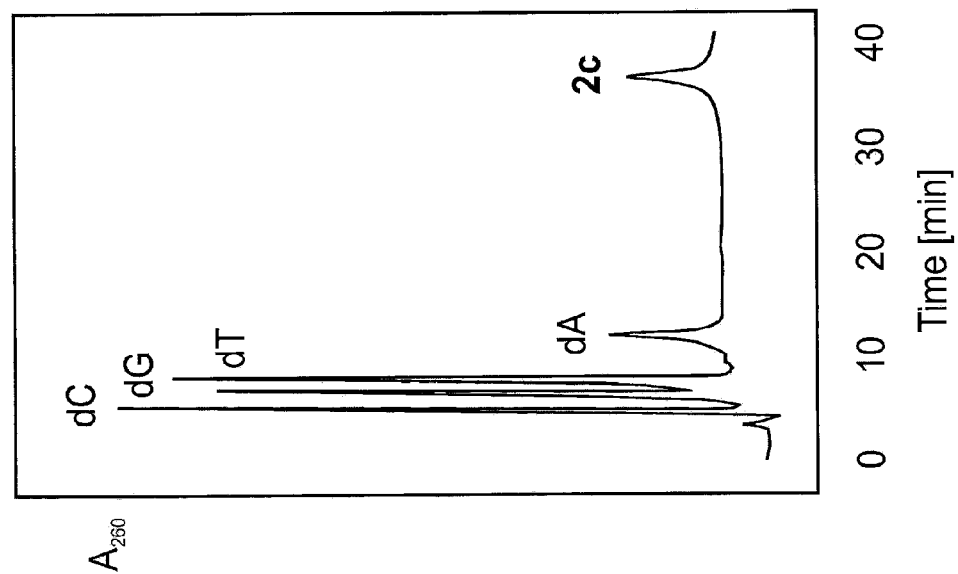

Automated solid-phase synthesis of the oligonucleotides (Tables 11-17) was performed using the phosphoramidites 16a, b and 18a-c as well as the standard building blocks. The syntheses followed the standard protocol (S. L. Beauge, M. Caruthers, *Tetrahedron Lett.* 1981, 22, 1859) and the coupling yields were always higher than 97%. Oligonucleotides containing halogenated dU-residues require the use of the 4-tert-butylphenoxyacetyl (tac) groups for the protection of the canonical phosphoramidites (E. Ferrer, C. Fàbrega, R. G. Garcia, F. Azorín, R. Eritja, *Nucleosides Nucleotides* 1996, 15, 907; J. C. Schulhof, D. Molko, and R. Teoule, *Nucleic Acids Res.* 1987, 15, 397; R. D. Sheardy and N. C. Seeman, *J. Org. Chem.* 1986, 51, 4301). In these cases the deprotection was performed with conc. ammonia at room temperature, while in all other cases the deprotection was carried out at 60° C. The oligonucleotides were detritylated and purified on purification cartridges (Applied Biosystems, 'User's Manual for Oligonucleotide Purification Cartridges)] or by reversed-phase HPLC (conditions for purification see Exper. Part). The homogeneity of the compounds was proven by ion-exchange chromatography (see Exper. Part). The composition of the oligonucleotides was determined by tandem hydrolysis with snake venom phosphodiesterase and alkaline phosphatase followed by RP-18 HPLC as described (F. Seela, C. Wei, *Helv. Chim. Acta* 1999, 82, 726). Typical examples are shown in FIG. 5c,d. The newly incorporated iodonucleosides 2c or 3c migrate slower than the canonical DNA constituents. The oligonucleotides were also characterized by MALDI-TOF mass spectra. The detected masses were in good agreement with the calculated values (Table 18).

TABLE 10

¹³C-NMR Chemical Shifts of Pyrazolo[3,4-d]-pyrimidine-4,6-diamine 2'-Deoxyribo-nucleosides[a]

| | $C(2)^c$ / $C(6)^d$ | $C(4)^c$ / $C(7°)^d$ | $C(5)^c$ / $C(3°)^d$ | $C(6)^e$ / $C(4)^d$ | $C(7)^d$ / $C(3)^d$ | C=O/ =CH | C=O/ =CH | $C(1')$ | $C(2')$ | $C(3')$ | $C(4')$ | $C(5')$ |
|---|---|---|---|---|---|---|---|---|---|---|---|---|
| 2b | 157.6 | 157.4 | 94.5 | 162.7 | 119.2 | | | 83.0 | 37.5 | 70.9 | 87.3 | 62.4 |
| 2c | 157.0 | 157.6 | 91.2 | 162.2 | 98.3 | | | 83.1 | 37.6 | 70.9 | 87.3 | 62.4 |
| 3a | 163.2 | 150.5 | 101.8 | 140.6 | | | | 84.2 | 38.5 | 70.5 | 87.4 | 61.3 |
| 3b | 159.1 | 149.7 | 95.6 | 140.6 | | | | 84.7 | 38.4 | 69.9 | 87.5 | 60.7 |
| 3c | 160.4 | 150.0 | 69.9 | 145.0 | | | | 84.6 | f) | 69.2 | 87.4 | 60.7 |
| 13a | 155.8 | 153.8 | 104.7 | 156.2 | 121.4 | 175.2 | 176.5 | 83.6 | 37.5 | 70.7 | 87.7 | 62.2 |
| 13b | 149.6 | 152.1 | 105.7 | 153.4 | 96.3 | 169.4 | 177.5 | 84.4 | 38.7 | 71.6 | 88.6 | 63.1 |
| 14 | 156.0 | 156.5 | 97.4 | 157.5 | 119.1 | 175.3 | | 83.3 | 37.5 | 70.8 | 87.5 | 62.2 |
| 15a | 155.6 | 154.9 | 98.5 | 157.5 | 117.2 | 174.7 | 175.2 | 83.5 | 37.6 | 72.2 | 85.4 | 63.6 |
| 15b | 149.5 | 152.1 | 105.8 | 153.2 | 96.2 | — | 177.5 | 84.8 | f) | 71.6 | 86.7 | 65.3 |
| 17a | 163.0 | 158.0 | 101.5 | 144.7 | | | | 84.1 | f) | 69.9 | 85.3 | 63.4 |
| 17b | 158.0 | 159.1 | 96.0 | 144.7 | | | | 84.9 | 38.4 | 70.3 | 85.7 | 63.6 |
| 17c | 158.0 | 160.5 | 69.8 | 144.2 | | | | 84.8 | 38.4 | 70.4 | 85.8 | 63.7 |

[a]Measured in (D₆)DMSO at 303 K.
[c]Purine numbering.
[d]Systematic numbering.
[e]Tentative.
[f] Superimposed by (D₆)DMSO.

TABLE 18

Molecular Masses (MH$^+$) of Oligonucleotides
Measured by MALDI-TOF Mass Spectrometry.

| Oligomer | SEQ ID NO: | MH$^+$ (calc.) | MH$^+$ (found) |
|---|---|---|---|
| 5'-d(TAG GTC AAT ACT) (102) | 2 | 3644.4 | 3645 |
| 5'-d(AGT ATT GAC CTA) (103) | 3 | 3644.4 | 3645 |
| 5'-d(TAG GTC 2a2aT ACT) (108) | 8 | 3674.4 | 3677 |
| 5'-d(AGT 2aTT G2aC CTA) (109) | 9 | 3674.4 | 3675 |
| 5'-d(TAG GTC 2b2bT ACT) (110) | 10 | 3832.5 | 3830 |
| 5'-d(AGT 2bTT G2bC CTA) (111) | 11 | 3832.5 | 3832 |
| 5'-d(T2bG GTC 2b2bT 2bCT) (201) | 16 | 4020 | 4021 |
| 5'-d(AGT ATT G2cC CTA) (202) | 17 | 3786? | 3787 |
| 5'-d(AGT 2cTT GAC CTA) (203) | 18 | 3786? | 3792 |
| 5'-d(AGT 2cTT G2cC CTA) (100) | 1 | 3926.5 | 3927 |
| 5'-d(TAG GTC 2c2cT ACT) (204) | 19 | 3927 | 3931 |
| 5'-d(T2cG GTC 2c2cT 2cCT) (205) | 20 | 4206.3 | 4210 |
| 5'-d(TAG G3aC AA3a ACT) (300) | 21 | 3613.1 | 3616 |
| 5'-d(AGT A3a3a GAC CTA) (301) | 22 | 3613.1 | 3615 |
| 5'-d(TAG G3bC AA3b ACT) (302) | 23 | 3774.1 | 3775 |
| 5'-d(AGT A3b3b GAC CTA) (303) | 24 | 3774.1 | 3772 |
| 5'-d(TAG G3cC AA3c ACT) (304) | 25 | 3868.1 | 3871 |
| 5'-d(AGT A3c3c GAC CTA) (305) | 26 | 3868.1 | 3871 |

2.2.2 Base Pair Stabilities of the Oligonucleotides Duplexes

The 7-bromo nucleoside 2b was found to stabilize DNA duplexes strongly while the non-halogenated compound 2a contributes very little to the duplex stability (see also F. Seela, G. Becher, *Helv. Chim. Acta* 2000, 83, 928; F. Seela, G. Becher, M. Zulauf, *Nucleosides Nucleotides* 1999, 18, 1399). The contribution of the purin-2,6-diamine nucleoside 1 on the duplex stability is even lower (C. Cheong, I. J. Tinoco, A. Chollet, *Nucleic Acids Res.* 1988, 16, 5115; J. D. Hoheisel, H. Lehrach, *FEBS Lett.* 1990, 274, 103). Thus, DNA duplexes containing compound 1-thymine base pairs are only slightly more stable than those with dA-dT pairs. As it was not known whether the stabilizing effect of the bromo nucleoside 2b will increase continuously by an increasing number of incorporations or will level off by multiple incorporations—as it is reported for other modified nucleosides (C. Bailly, M. J. Waring, *Nucleic Acids Res.* 1998, 26, 4309 and references therein)—a series of oligonucleotides were synthesized containing the halogenated compound 2b in a consecutive manner or in distant position. The modified residues were incorporated in one or both strands of a double-stranded DNA. The total number of incorporations was increased in duplexes from 1 to 6. The non-halogenated duplexes containing compound 2a were prepared for comparison. Apart from the incorporation of the bromo nucleoside 2b, the iodo compound 2c was also studied. For all experiments the non-self-complementary duplex 5'-d(TAGGTCAATACT) (SEQ ID NO: 2) (102)—5'-d(AGTATTGACCTA) (SEQ ID NO: 3) (103) was chosen.

Figure 6:
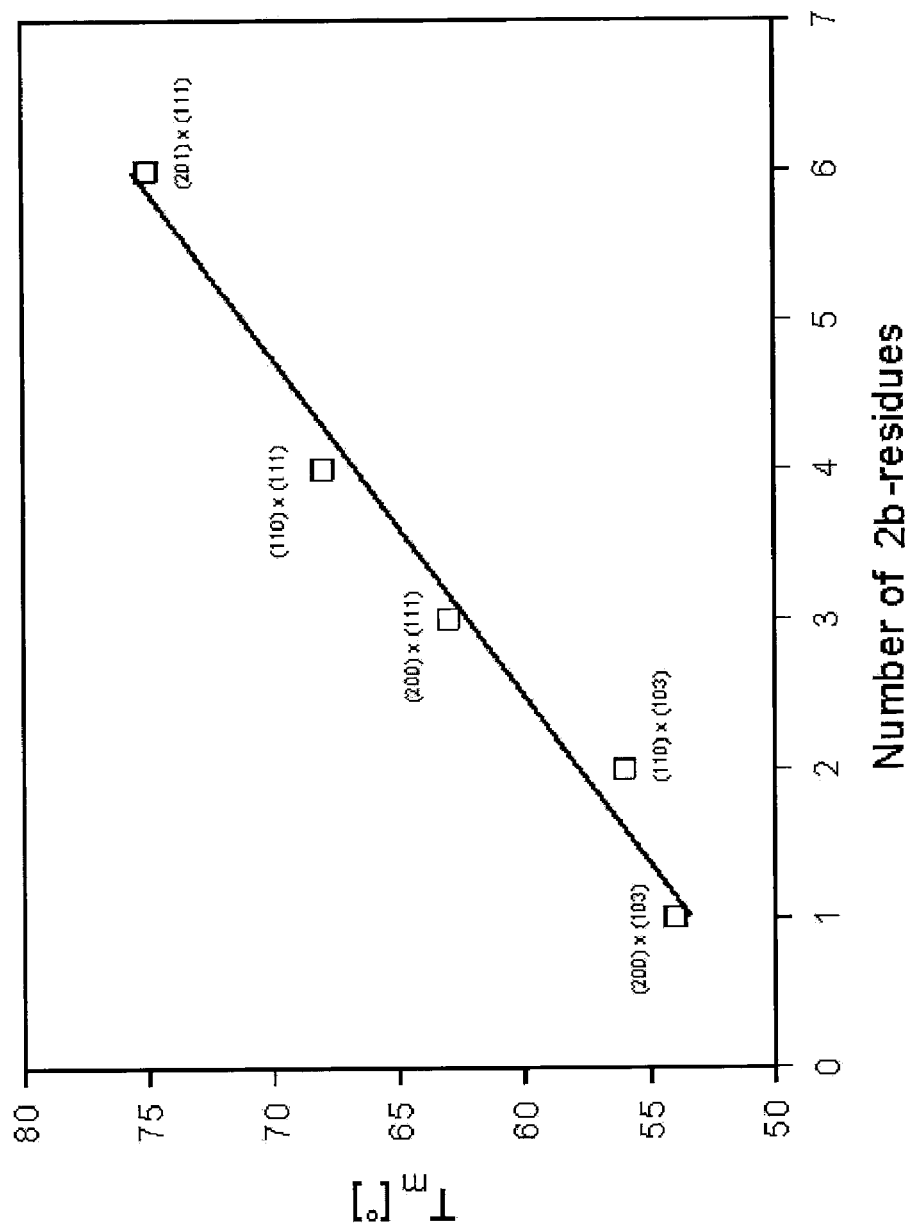
FIG. 6. The tendency of T$_m$-increase vs. the number of 2b residues.

The non-halogenated nucleoside 2a increases the T$_m$-value of the standard duplex 102•103 by only 1° per modified residue (Table 11 and F. Seela, G. Becher, 2001, submitted). Contrary, the bromo compound 2b contributes a 4-5° stabilization per modified residue which represents an outstanding high stabilization induced by a non-canonical base. The strength of this effect is sequence-dependent but the stability of the duplexes increases with an increasing number of 2b—incorporations as shown in FIG. 6. When the iodo nucleoside 2c was replacing the bromo compound 2b, a similar effect regarding duplex stabilization is observed (Table 11). The effects of halogen substituents introduced into the pyrazolo[3,4-d]pyrimidine derivatives of dG (F. Seela, G. Becher, *Helv. Chim. Acta* 1999, 82, 1640) or dA (F. Seela, M. Zulauf, *J. Chem. Soc. Perkin Trans.* 1 1999, 479) amounts only to 2° per modified residue.

A similar set of experiments as described for the duplexes containing the halogenated 8-aza-7-deazapurine nucleosides 2b or 2c was performed with the halogenated T-deoxyuridine derivatives 3b or 3c (Table 12). Neither the bromo nucleoside 3b nor the iodo nucleoside 3c increases the stability of the duplexes significantly compared to that of the non-halogenated 3a or dT. Thus, only the base pairs of type I (Scheme 8) with halogen substituents located at the 7-position of the 8-aza-7-deazapurine (pyrazolo[3,4-d]pyrimidine) moiety are stabilized by the halogen substituents while those of the type II (Scheme 8) with the halogens attached to the 5-positions of the pyrimidine base exert little influence compared to those with dA-dT pairs.

Scheme 8

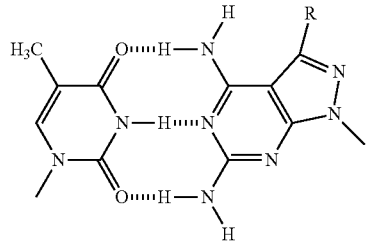

base pair Ia: R = H
Ib: R = Br
Ic: R = I

-continued

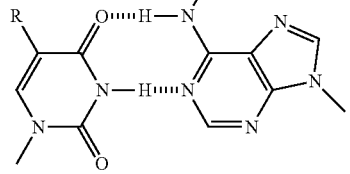

base pair IIa: R = H
IIb: R = Br
IIc: R = I

TABLE 11

$T_m$ Values and Thermodynamic Data of Duplex Formation of Oligonucleotides Containing the Pyrazolo[3,4-d]pyrimidine Nucleosides 2a-c Opposite to dT[a])

| Compound | SEQ ID NO: | Tm [° C.] | ΔH° [kcal/mol] | ΔS° [cal/mol K] | ΔG°$_{310}$ [kcal/mol] |
|---|---|---|---|---|---|
| 5'-d(TAG GTC AAT ACT) (102) | 2 | 47 | −83.8 | −235.9 | −10.6 |
| 3'-d(ATC CAG TTA TGA) (103) | 3 | | | | |
| 5'-d(TAG GTC 2a2aT ACT) (108) | 8 | 50 | −93.3 | −263.09 | −11.7 |
| 3'-d(ATC CAG TTA TGA) (103) | 3 | | | | |
| 5'-d(TAG GTC AAT ACT) (102) | 2 | 50 | −98.79 | −279.63 | −12.06 |
| 3'-d(ATC C2aG TT2a TGA) (109) | 9 | | | | |
| 5'-d(TAG GTC 2a2aT ACT) (108) | 8 | 51 | −98.66 | −278.58 | −12.26 |
| 3'-d(ATC C2aG TT2a TGA) (109) | 9 | | | | |
| 5'-d(TAG GTC 2bAT ACT) (200) | 15 | 54 | −99.96 | −280.74 | −12.89 |
| 3'-d(ATC CAG TTA TGA) (103) | 3 | | | | |
| 5'-d(TAG GTC 2b2bT ACT) (110) | 10 | 56 | −91.42 | −251.66 | −13.37 |
| 3'-d(ATC CAG TTA TGA) (103) | 3 | | | | |
| 5'-d(TAG GTC AT ACT) (102) | 2 | 59 | −91.85 | −251.25 | −13.92 |
| 3'-d(ATC C2bG TT2b TGA) (111) | 11 | | | | |
| 5'-d(TAG GTC 2bAT ACT) (200) | 15 | 63 | −100.70 | −274.04 | −15.70 |
| 3'-d(ATC C2bG TT2b TGA) (111) | 11 | | | | |
| 5'-d(TAG GTC 2b2bT ACT) (110) | 10 | 67 | −105.40 | −285.02 | −17.00 |
| 3'-d(ATC C2bG TT2b TGA) (111) | 11 | | | | |
| 5'-d(T2bG GTC 2b2bT 2bCT) (201) | 16 | 64 | −99.08 | −268.47 | −15.81 |
| 3'-d(ATC CAG TTA TGA) (103) | 3 | | | | |

TABLE 11-continued

T$_m$ Values and Thermodynamic Data of Duplex Formation of Oligonucleotides Containing the Pyrazolo[3,4-d]pyrimidine Nucleosides 2a-c Opposite to dT[a]

| Compound | SEQ ID NO: | Tm [° C.] | ΔH° [kcal/mol] | ΔS° [cal/mol K] | ΔG°$_{310}$ [kcal/mol] |
|---|---|---|---|---|---|
| 5'-d(T2bG GTC 2b2bT 2bCT) (201) | 16 | 75 | −107.43 | −283.41 | −19.53 |
| 3'-d(ATC C2bG TT2b TGA) (111) | 11 | | | | |
| 5'-d(TAG GTC AAT ACT) (102) | 2 | 51 | −90.65 | −254.58 | −11.69 |
| 3'-d(ATC C2cG TTA TGA) (202) | 17 | | | | |
| 5'-d(TAG GTC AAT ACT) (102) | 2 | 54 | −93.22 | −260.43 | −12.45 |
| 3'-d(ATC CAG TT2c TGA) (203) | 18 | | | | |
| 5'-d(TAG GTC AAT ACT) (102) | 2 | 57 | −95.09 | −263.29 | −13.43 |
| 3'-d(ATC C2cG TT2c TGA) (100) | 1 | | | | |
| 5'-d(TAG GTC 2c2cT ACT) (204) | 19 | 55 | −96.46 | −268.72 | −13.12 |
| 3'-d(ATC CAG TTA TGA) (103) | 3 | | | | |
| 5'-d(TAG GTC 2c2cT ACT) (204) | 19 | 59 | −102.95 | −284.63 | −14.67 |
| 3'-d(ATC C2cGT TTA TGA) (202) | 17 | | | | |
| 5'-d(TAG GTC 2c2cT ACT) (204) | 19 | 66 | −104.93 | −284.73 | −16.62 |
| 3'-d(ATC C2cGT TT2c TGA) (100) | 1 | | | | |
| 5'-d(T2cG GTC2c2cT 2cCT) (205) | 20 | 72 | — | — | — |
| 3'-d(ATC C2cG TT2c TGA) (100) | 1 | | | | |

[a]Thermodynamic parameters are derived from the fitting of melting curves measured at 260 nm in 0.1 M NaCl, 10 mM MgCl$_2$, and 10 mM Na-cacodylate buffer, pH 7.0 with 5 μM + 5 μM single strand concentration. The ΔG° are taken directly from the program Meltwin 3.0 referring to 310°. Earlier publications of our laboratory using the fitting program refer to the same temperature and not to 298° as indicated. The thermodynamic data determined from the van't Hoff plots using the concentration dependence of the T$_m$-values are consistent with those obtained from the curve fitting within 15%. The van't Hoff data of the formation of the duplex 102·103 are the following: ΔH° = 86.8 kcal/mol; ΔS° = 243.7 cal/K mol; ΔG°$_{310}$ = 11.3 kcal/mol.

TABLE 12

T$_m$ Values and Thermodynamic Data of Duplex Formulation of Oligonucleotides Containing the Pyrimidine Nucleosides 3a-c Opposite to dA[a]

| Compound | SEQ ID NO: | Tm [° C.] | ΔH° [kcal/mol] | ΔS° [cal/mol K] | ΔG°$_{310}$ [kcal/mol] |
|---|---|---|---|---|---|
| 5'-d(TAG G3aC AA3a ACT) (300) | 21 | 47 | −86.35 | −244.74 | −10.45 |
| 3'-d(ATC CAG TTA TGA) (103) | 3 | | | | |
| 5'-d(TAG GTC AAT ACT) (102) | 2 | 48 | −92.11 | −261.95 | −10.86 |
| 3'-d(ATC CAG 3a3aA TGA) (301) | 22 | | | | |

TABLE 12-continued

T$_m$ Values and Thermodynamic Data of Duplex
Formulation of Oligonucleotides Containing the
Pyrimidine Nucleosides 3a-c Opposite to dA[a])

| Compound | SEQ ID NO: | Tm [° C.] | ΔH° [kcal/mol] | ΔS° [cal/mol K] | ΔG°$_{310}$ [kcal/mol] |
|---|---|---|---|---|---|
| 5'-d(TAG G3aC AA3a ACT) (300) | 21 | 46 | −86.37 | −245.42 | −10.25 |
| 3'-d(ATC CAG 3a3aA TGA) (301) | 22 | | | | |
| 5'-d(TAG G3bC AA3b ACT) (302) | 23 | 48 | −95.76 | −271.88 | −11.44 |
| 3'-d(ATC CAG TTA TGA) (103) | 3 | | | | |
| 5'-d(TAG GTC A A T ACT) (102) | 2 | 49 | −97.43 | −276.95 | −11.53 |
| 3'-d(ATC CAG 3b3bA TGA) (303) | 24 | | | | |
| 5'-d(TAG G3bC AA3b ACT) (302) | 23 | 49 | −94.25 | −267.57 | −11.26 |
| 3'-d(ATC CAG 3b3bA TGA) (303) | 24 | | | | |
| 5'-d(TAG G3cC AA3c ACT) (304) | 25 | 49 | −96.38 | −273.73 | −11.48 |
| 3'-d(ATC CAG TTA TGA) (103) | 3 | | | | |
| 5'-d(TAG GTC AAT ACT) (102) | 2 | 50 | −94.99 | −269.20 | −11.50 |
| 3'-d(ATC CAG 3c3cA TGA) (305) | 26 | | | | |
| 5'-d(TAG G3cC AA3c ACT) (304) | 25 | 50 | −99.14 | −281.47 | −11.85 |
| 3'-d(ATC CAG 3c3cA TGA) (305) | 26 | | | | |

[a])See Table 11.

As the stability of the base pairs of the halogenated pyrimidine nucleosides 3b or 3c with dA was low compared to the halogenated pyrazolo[3,4-d]pyrimidine compounds 2b or 2c incorporated opposite to dT, tridendate base pairs are formed in which the halogenated pyrimidine nucleosides 3a-c are located opposite to the purine-2.6-diamine nucleoside 1 instead of dA (Scheme 9, by type III). In this case a strengthening of the base pair can be expected if the formation of a third hydrogen bond is possible. However, the T$_m$-values of those duple-xes were also not influenced significantly by the replacement of dA-residues by the nucleoside 1 (Table 13). This indicates that the 2-amino group does not participate in possible base pairs as shown in IIIa-c (Scheme 9), a finding which is similar to that observed for a base pair between 1 and dT (F. Seela, G. Becher, 2001, submitted; C. Cheong, I. J. Tinoco, A. Chollet, *Nucleic Acids Res.* 1988, 16, 5115; J. D. Hoheisel, H. Lehrach, *FEBS Lett.* 1990, 274, 103). A similar behaviour was found in the case of duplexes containing the base pair IVa (Scheme 9) formed between nucleoside 2a and the pyrimidine nucleosides 3a-c (Table 13). Nevertheless, the duplexes incorporating the base pairs IVb,c are slightly more stable than those containing the base pairs IIIb,c.

Scheme 9

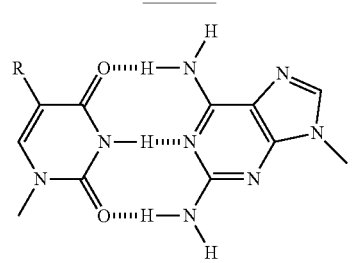

base pair IIIa: R = H
IIIb: R = Br
IIIc: R = I

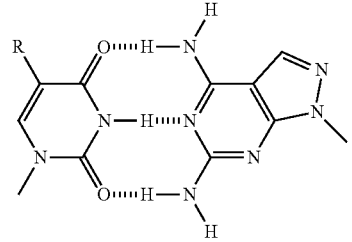

base pair IVa: R = H
IVb: R = Br
IVc: R = I

TABLE 13

T<sub>m</sub> Values and Thermodynamic Data of Oligonucleotide
Duplexes Containing the Halogenated Pyrimidine Nucleosides
3a-c Opposite to the Purin-2,6-diamine Nucleoside 1 or the
Pyrazolo[3,4-d]pyrimidindin-4,6-diamine Nucleoside 2a[a])

| | SEQ ID NO: | $T_m$ [° C.] | $\Delta H°$ [kcal/mol] | $\Delta S°$ [cal/mol K] | $\Delta G°_{310}$ [kcal/mol] |
|---|---|---|---|---|---|
| 5'-d(TAG GTC AAT ACT) (102) | 2 | 49 | −83.15 | −232.81 | −10.94 |
| 3'-d(ATC C1G TT1 TGA) (105) | 5 | | | | |
| 5'-d(TAG G3aC AA3a ACT) (300) | 21 | 48 | −73.03 | −202.44 | −10.25 |
| 3'-d(ATC C1G TT1 TGA) (105) | 5 | | | | |
| 5'-d(TAG G3bC AA3b ACT) (302) | 23 | 49 | −73.84 | −203.94 | −10.59 |
| 3'-d(ATC C1G TT1 TGA) (105) | 5 | | | | |
| 5'-d(TAG G3cC AA3c ACT) (304) | 25 | 49 | −77.60 | −215.48 | −10.76 |
| 3'-d(ATC C1G TT1 TGA) (105) | 5 | | | | |
| 5'-d(T1G GTC 11T 1CT) (104) | 4 | 48 | −54.74 | −144.65 | −9.88 |
| 3'-d(ATC CAG TTA TGA) (103) | 3 | | | | |
| 5'-d(T1G GTC 11T 1CT) (104) | 4 | 48 | −60.03 | −161.49 | −9.94 |
| 3'-d(ATC CAG 3a3aA TGA) (301) | 22 | | | | |
| 5'-d(T1G GTC 11T 1CT) (104) | 4 | 48 | −60.09 | −160.37 | −10.35 |
| 3'-d(ATC CAG 3b3bA TGA) (303) | 24 | | | | |
| 5'-d(T1G GTC 11T 1CT) (104) | 4 | 48 | −62.35 | −167.33 | −10.45 |
| 3'-d(ATC CAG 3c3cA TGA) (305) | 26 | | | | |
| 5'-d(TAG GTC 2a2aT ACT) (108) | 8 | 49 | −87.32 | −245.54 | −11.16 |
| 3'-d(ATC CAG 3a3aA TGA) (301) | 22 | | | | |
| 5'-d(TAG GTC 2a2aT ACT) (108) | 8 | 50 | −89.11 | −250.34 | −11.47 |
| 3'-d(ATC CAG 3b3bA TGA) (303) | 24 | | | | |
| 5'-d(TAG GTC 2a2aT ACT) (108) | 8 | 51 | −81.32 | −225.60 | −11.35 |
| 3'-d(ATC CAG 3c3cA TGA) (305) | 26 | | | | |
| 5'-d(TAG G3aC AA3a ACT) (300) | 21 | 49 | −90.30 | −253.96 | −11.53 |
| 3'-d(ATC C2aG TT2a TGA) (109) | 9 | | | | |
| 5'-d(TAG G3bC AA3b ACT) (302) | 23 | 51 | −93.05 | −261.91 | −11.82 |
| 3'-d(ATC C2aG TT2a TGA) (109) | 9 | | | | |
| 5'-d(TAG G3cC AA3c ACT) (304) | 25 | 50 | −90.58 | −254.11 | −11.77 |
| 3'-d(ATC C2aG TT2a TGA) (109) | 9 | | | | |

[a])See Table 11.

A significant duplex stabilization was observed when the halogenated 8-aza-7-deazapurine nucleosides 2b or 2c were incorporated opposite to the pyrimidine nucleosides 3a-c (Table 14 and Scheme 10, by of type V and VI). The $T_m$- increase amounts to about 4-5° per incorporated residue of the halogenated nucleosides 2b or 2c. All duplexes containing the halogenated nucleosides 2b or 2c (Scheme 10) give very similar $T_m$-values, no matter which pyrimidine monomer is located opposite to it. Thus, only halogen substituents attached to the modified purine residues lead to a duplex stabilization while to halogens linked to the 5-position of the 2′-deoxyuridine moiety contribute very little to the duplex stability (S. M. Freier and K.-H. Altman, *Nucleic Acids Res.* 1997, 25, 4429; F. Seela, Y. He, *Helv. Chim. Acta* 2000, 83, 2527; S. Wang, E. T. Kool, *Biochemistry* 1995, 34, 4125)

Scheme 10

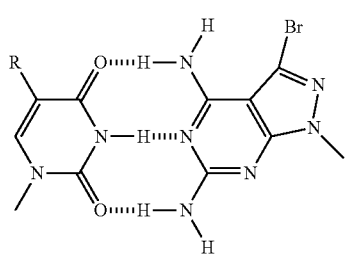

base pair Va: R = H
Vb: R = Br
Vc: R = I

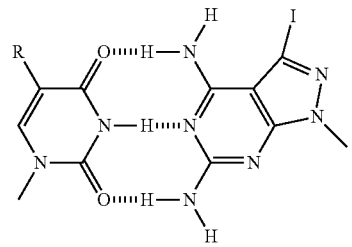

base pair VIa: R = H
VIb: R = Br
VIc: R = I

TABLE 14

$T_m$ Values and Thermodynamic Data of Oligonucleotides Containing the Pyrazolo[3,4-d]pyrimidin-4,6-diamine Nucleosides 2b-c Opposite to dT and 3a-c$^a$)

| Duplex | SEQ ID NO: | Tm [° C.] | ΔH° [kcal/mol] | ΔS° [cal/mol K] | ΔG°$_{310}$ [kcal/mol] |
|---|---|---|---|---|---|
| 5′-d(TAG GTC 2bAT ACT) (200) | 15 | 52 | −92.88 | −260.97 | −11.94 |
| 3′-d(ATC CAG 3a3aA TGA) (301) | 22 | | | | |
| 5′-d(TAG GTC 2b2bT ACT) (110) | 10 | 55 | −96.78 | −269.67 | −13.14 |
| 3′-d(ATC CAG 3a3aA TGA) (301) | 22 | | | | |
| 5′-d(T2bG GTC 2b2bT 2bCT) (201) | 16 | 64 | −101.57 | −276.51 | −15.82 |
| 3′-d(ATC CAG 3a3aA TGA) (301) | 22 | | | | |
| 5′-d(TAG GTC 2bAT ACT) (200) | 15 | 54 | −98.06 | −275.03 | −12.76 |
| 3′-d(ATC CAG 3b3bA TGA) (303) | 24 | | | | |
| 5′-d(TAG GTC 2b2bT ACT) (110) | 10 | 55 | −95.42 | −266.68 | −12.71 |
| 3′-d(ATC CAG 3b3bA TGA) (303) | 24 | | | | |
| 5′-d(T2bG GTC 2b2bT 2bCT) (201) | 16 | 65 | −106.49 | −290.34 | −16.44 |
| 3′-d(ATC CAG 3b3bA TGA) (303) | 24 | | | | |
| 5′-d(TAG GTC 2bAT ACT) (200) | 15 | 54 | −87.97 | −244.29 | −12.20 |
| 3′-d(ATC CAG 3c3cA TGA) (305) | 26 | | | | |
| 5′-d(TAG GTC 2b2bT ACT) (110) | 10 | 55 | −89.17 | −246.44 | −12.74 |
| 3′-d(ATC CAG 3c3cA TGA) (305) | 26 | | | | |
| 5′-d(T2bG GTC 2b2bT 2bCT) (201) | 16 | 65 | −101.57 | −275.34 | −16.18 |
| 3′-d(ATC CAG 3c3cA TGA) (305) | 26 | | | | |

TABLE 14-continued

T$_m$ Values and Thermodynamic Data of Oligonucleotides
Containing the Pyrazolo[3,4-d]pyrimidin-4,6-diamine
Nucleosides 2b-c Opposite to dT and 3a-c[a])

| Duplex | SEQ ID NO: | Tm [° C.] | ΔH° [kcal/mol] | ΔS° [cal/mol K] | ΔG°$_{310}$ [kcal/mol] |
|---|---|---|---|---|---|
| 5'-d(TAG G3aC AA3a ACT) (300) | 21 | 56 | -95.76 | -265.45 | -13.43 |
| 3'-d(ATC C2bG TT2b TGA) (111) | 11 | | | | |
| 5'-d(TAG G3bC AA3b ACT) (302) | 23 | 56 | -96.53 | -268.70 | -13.20 |
| 3'-d(ATC C2bG TT2b TGA) (111) | 11 | | | | |
| 5'-d(TAG G3cC AA3c ACT) (304) | 25 | 57 | -97.07 | -269.07 | -13.62 |
| 3'-d(ATC C2bG TT2b TGA) (111) | 11 | | | | |
| 5'-d(TAG G3aC AA3a ACT) (300) | 21 | 55 | -96.93 | -270.69 | -12.98 |
| 3'-d(ATC C2cG TT2c TGA) (100) | 1 | | | | |
| 5'-d(TAG G3bC AA3b ACT) (302) | 23 | 55 | -100.82 | -282.19 | -13.29 |
| 3'-d(ATC C2cG TT2c TGA) (100) | 1 | | | | |
| 5'-d(TAG G3cC AA3c ACT) (304) | 25 | 55 | -98.00 | -273.26 | -13.25 |
| 3'-d(ATC C2cG TT2c TGA) (100) | 1 | | | | |

[a])See Table 11.

2.2.3 Base Discrimination

In order to investigate the discrimination of the iodo nucleoside 2c towards the four canonical DNA—constituents, hybridization experiments were performed according to Table 15. As expected, the base pair 2c-dT is the strongest (102•100, T$_m$=59°) while those of the duplexes forming mismatches melt at a significantly lower temperature (Table 15). The discrimination of the iodo nucleoside 2c is similar to that of the canonical nucleosides except that the duplex 401•100 (T$_m$=52°) shows a 7° lower T$_m$-value than the duplex 102•100 (T$_m$=59°), while duplex 401•103 (T$_m$=46°) has almost the same stability as the parent duplex 102•103 (T$_m$=48°). The high T$_m$-value of 401•103 is the result of the formation of the dG-dA Hoogsteen pair which is obviously not formed between dG and compound 2c.

TABLE 15

T$_m$-Values of Oligonucleotides Containing the
Pyrazolo[3,4-d]pyrimidin-4,6-diamine Nucleoside 2c
Opposite to the Four Canonical Nucleosides[a])

| Duplex | SEQ ID NO: | T$_m$ [° C.] | | SEQ ID NO: | T$_m$ [° C.] |
|---|---|---|---|---|---|
| 5'-d(TAG GTC AAT ACT) (102) | 2 | 57 | 5'-d(TAG GTC AAT ACT) (102) | 2 | 48 |
| 3'-d(ATC C2cG TT2c TGA) (100) | 1 | | 3'-d(ATC CAG TTA TGA) (103) | 3 | |
| 5'-d(TAG GAC AAT ACT) (400) | 27 | 45 | 5'-d(TAG GAC AAT ACT) (400) | 27 | 38 |
| 3'-d(ATC C2cG TT2c TGA) (100) | 1 | | 3'-d(ATC CAG TTA TGA) (103) | 3 | |
| 5'-d(TAG GGC AAT ACT) (401) | 28 | 50 | 5'-d(TAG GGC AAT ACT) (401) | 28 | 46 |
| 3'-d(ATC C2cG TT2c TGA) (100) | 1 | | 3'-d(ATC CAG TTA TGA) (103) | 3 | |

TABLE 15-continued $T_m$-Values of Oligonucleotides Containing the
Pyrazolo[3,4-d]pyrimidin-4,6-diamine Nucleoside 2c
Opposite to the Four Canonical Nucleosides[a]

| Duplex | SEQ ID NO: | $T_m$ [° C.] | Duplex | SEQ ID NO: | $T_m$ [° C.] |
|---|---|---|---|---|---|
| 5'-d(TAG GCC AATACT) (402)<br>3'-d(ATC C2cG TT2c TGA) (100) | 29<br>1 | 45 | 5'-d(TAG GCC AATACT) (402)<br>3'-d(ATC CAG TTA TGA) (103) | 29<br>3 | 36 |

[a] see Table 11.

Figure 7A:
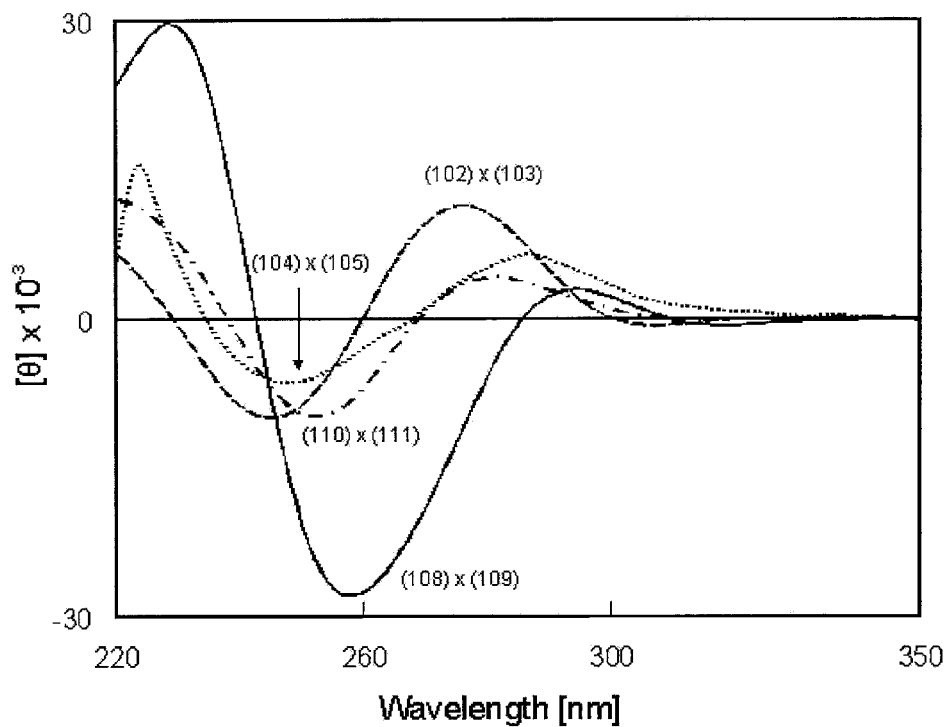
FIG. 7. (a) CD spectra of duplexes 102•103, 108•109, 110•111, 104•105 (in 100 mM NaCl, 100 mM MgCl$_2$, and 60 mM Na-cacodylate (pH 7.0). (b) CD Spectra of duplexes 102•403, 108•403, 110•403, 104•403 in 100 mM NaCl, 100 mM MgCl$_2$, and 60 mM Na-cacodylate (pH 7.0), the concentration of the oligonucleotides is 5 μM+5 μM (single strand concentration).

The CD-spectra of the duplexes containing the 2-amino-8-aza-7-deazaadenine derivatives 2a, b were measured next. A B-like DNA structure can be deduced from the curves displayed in FIG. 7a. A positive Cotton effect around 270 to 290 nm and a negative lobe at 250 nm are observed for the standard duplex (102•103). The CD spectrum of the duplex 104•105 containing 1 shows significant differences similar to that of 110•111 while the duplex 108•109 shows a stronger negative Cotton effect at 260 nm and a positive one at 235 nm. Similar differences were reported for the oligonucleotides containing 7-substituted 8-aza-7-deaza-7-iodoguanine (N. Ramzaeva, F. Seela, Helv. Chim. Acta 1996, 79, 1549).

2.4 DNA-RNA Hybrids

Figure 7B:
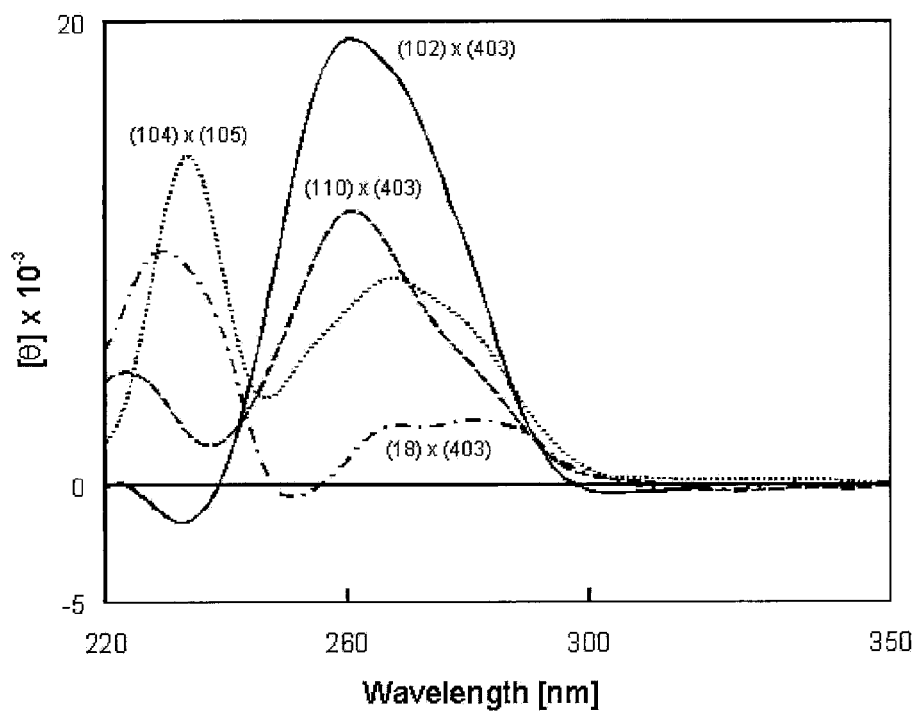

In order to study the influence of the 2,6-diamino nucleosides 1 and 2a,b on the stability of DNA-RNA hybrids, the oligodeoxyribonucleotides 110, 300, 302, 304, 104 and 102 were hybridized with the oligoribonucleotide 403. Table 16 shows that the various modifications exert a significant influence on the duplex stability of the DNA-RNA hybrids. While the incorporation of the non-halogenated nucleosides 1 or 2a stabilizes the DNA-RNA structure very little, the hybridization of the oligonucleotide containing 2b with 403 (110•403) show a significant increase of the duplex stability as in DNA. Compounds 3b and 3c enhance the thermal stability of DNA-RNA to a small degree, which is also observed for other modifications of 2'-deoxyuridine (B. C Froehler, S. Wadwani, T. J. Terhorst, S. R. Gerrard, Tetrahedron 1992, 33, 5307; J. Sági, A. Szemzö, K. Ébinger, A. Szabolcs, G. Sági, E. Ruff, L. Ötvös, Tetrahedron Lett. 1993, 34, 2191). The hypochromicities of the chimeric hybrids are slightly decreased over those of the DNA-DNA duplexes (data not shown). From the CD-spectra of FIG. 7b it can be seen that the DNA-RNA hybrids adopt the A-form (N. Ramzaeva, C. Mittelbach, F. Seela, Helv. Chim. Acta 1997, 80, 1809).

TABLE 16

$T_m$ Values and Thermodynamic Data of DNA-RNA Hybrids[a]

| Duplex | SEQ ID NO: | $T_m$ [° C.] | ΔH° [kcal/mol] | ΔS° [cal/mol · K] | ΔG°$_{310}$ [kcal/mol] |
|---|---|---|---|---|---|
| 5'-d(TAG GTC AAT ACT) (102)<br>3'-(AUC CAG UUA UGA) (403) | 2<br>30 | 45 | −92.1 | −264.0 | −10.2 |
| 5'-d(T1G GTC 11T 1CT) (104)<br>3'-(AUC CAG UUA UGA) (403) | 4<br>30 | 48 | −60.46 | −162.12 | −10.18 |
| 5'-d(TAG GTC 2a2aT ACT) (108)<br>3'-(AUC CAG UUA UGA) (403) | 8<br>30 | 48 | — | — | — |
| 5'-d(TAG GTC 2b2bT ACT) (110)<br>3'-(AUC CAG UUA UGA) (403) | 10<br>30 | 53 | −98.64 | −276.97 | −12.74 |
| 5'-d(TAG G3aC AA3a ACT) (300)<br>3'-(AUC CAG UUA UGA) (403) | 21<br>30 | 44 | −74.43 | −208.26 | −9.84 |
| 5'-d(TAG G3bC AA3b ACT) (302)<br>3'-(AUC CAG UUA UGA) (403) | 23<br>30 | 48 | −77.19 | −215.13 | −10.47 |
| 5'-d(TAG G3cC AA3c ACT) (304)<br>3'-(AUC CAG UUA UGA) (403) | 25<br>30 | 47 | −78.77 | −220.52 | −10.37 |

[a] See Table 11.

2.5 Duplexes with Parallel Chain Orientation

The base pairing of the nucleosides 1,2a-c as well as 3b, c was also investigated in parallel stranded DNA [29]. For this purpose it was necessary to replace the dC-dG pair by a $m^5iC_d$-$iG_d$ pair. The duplexes 102•115 and 116•103 served as standards (F. Seela, C. Wei, G. Becher, M. Zulauf, P. Leonard, Bioorg. Med. Chem. Lett. 2000, 10, 289). Substitution of dA-residues by the diamino nucleoside 1 resulted in a slight stability decrease of the ps-duplexes 104•115 and 116•105 (Table 17). The incorporation of 2a-c into the ps-DNA resulted in a significant increase of the $T_m$-values. The incorporation of the substituted pyrimidine nucleosides 3b, c in place of dT leads only to minor changes of the $T_m$-values. From this it can be concluded that similar to DNA with antiparallel chain orientation, the halogen substituents of the "purine" nucleosides 2b, c stabilize these duplexes while the halogen substituents of the pyrimidine nucleosides contribute very little to the duplex stability.

TABLE 17

$T_m$-Values and Thermodynamic Data of Parallel-Stranded Oligonucleotide Duplexes Containing the Nucleosides 1, 2a-c and 3a-c[a,b]

| Duplex | SEQ ID NO: | $T_m$ [° C.] | ΔH° [kcal/mol] | ΔS° [cal/mol · K] | ΔG°$_{310}$ [kcal/mol] |
|---|---|---|---|---|---|
| 5'-d(TAG GTC AAT ACT) (102) | 2 | 39 | −74.4 | −212.3 | −8.5 |
| 5'-d(AtiC iCAiG TTA TiGA) (115) | 13 | | | | |
| 5'-d(T1G GTC 11T 1CT) (104) | 4 | 36 | −48.12 | −129.68 | −7.90 |
| 5'-d(ATiC iCAiG TTA TiGA) (115) | 13 | | | | |
| 5'-d(TAG GTC 2a2aT ACT) (108) | 8 | 41 | −61.77 | −170.95 | −8.75 |
| 5'-d(ATiC iCAiG TTA TiGA) (115) | 13 | | | | |
| 5'-d(TAG GTC 2b2bT ACT) (110) | 10 | 45 | −66.59 | −183.94 | −9.54 |
| 5'-d(ATiC iCAiG TTA TiGA) (115) | 13 | | | | |
| 5'-d(TAG G3bC AA3b ACT) (302) | 23 | 37 | −50.64 | −137.87 | −7.88 |
| 5'-d(ATiC iCAiG TTA TiGA) (115) | 13 | | | | |
| 5'-d(TAG G3cC AA3c ACT) (304) | 25 | 36 | −55.09 | −152.14 | −7.90 |
| 5'-d(ATiC iCAiG TTA TiGA) (115) | 13 | | | | |
| 5'-d(TiCA TAA iCTiG iGAT) (116) | 14 | 44 | −85.0 | −242.0 | −10.0 |
| 5'-d(AGT ATT GAC CTA) (103) | 3 | | | | |
| 5'-d(TiCA TAA iCTiG iGAT) (116) | 14 | 39 | −61.00 | −169.68 | −8.38 |
| 5'-d(AGT 1TT G1C CTA) (105) | 5 | | | | |
| 5'-d(TiCA TAA iCTiG iGAT) (116) | 14 | 45 | −80 | −230 | −10.3 |
| 5'-d(AGT 2aTT G2aC CTA) (109) | 9 | | | | |
| 5'-d(TiCA TAA iCTiG iGAT) (116) | 14 | 48 | −68.34 | −186.29 | −10.56 |
| 5'-d(AGT 2bTT G2bC CTA) (111) | 11 | | | | |
| 5'-d(TiCA TAA iCTiG iGAT) (116) | 14 | 43 | −76.03 | −215.51 | −9.19 |
| 5'-d(AGT A3b3b GAC CTA) (303) | 24 | | | | |
| 5'-d(TiCA TAA iCTiG iGAT) (116) | 14 | 42 | −67.15 | −187.02 | −9.15 |
| 5'-d(AGT A3c3c GAC CTA) (305) | 26 | | | | |

[a] Measured at 260 nm in 1 M NaCl, 100 M MgCl$_2$, 60 mM Na-cacodylate buffer, pH 7.0 with 5 + 5 μM oligomer concentration.
[b] d(iC) = m$^5$iC$_d$ = 2'-deoxy-5-methylisocytidine.

2.3. Conclusion

The halogen substituents introduced into the 7-position of the 8-aza-7-deazapurine 2'-deoxynucleoside (2b, c) or the 5-position of 2'-deoxyuridine residues (3a-c) have very different influences on the stability of nucleic acid duplexes. In the case of the 7-halogenated 8-aza-7-deazapurine 2'-deoxynucleosides 2b, c, each monomer contributes about 4°-5° to the duplex stabilization, while the pyrimidine nucleosides 3a-c show very little influence or even no effect. This is surprising as the halogens in both series of nucleobases are directed into the major groove of B-DNA both being in a not identical but a very similar environment. When both, the halogenated pyrimidines and the halogenated 8-aza-7-deazapurine nucleosides are present in a DNA-duplex only the latter make a contribution to the duplex stabilization. Consequently, the increase of the hydrophobic character of the major groove induced by the lipophilic halogen substituents and the expelling of water molecules is not the major effect induced by the halogenation of the major groove. Apparently, stacking interaction between the nearest neighbours are strengthened in the case of 2b, c but not with 3b, c.

2.4. Experimental Part

Monomers. General. See preceeding manuscripts (F. Seela, G. Becher, *Helv. Chim. Acta* 2000, 83, 928; F. Seela, G. Becher, M. Zulauf, *Nucleosides Nucleotides* 1999, 18, 1399; F. Seela, M. Zulauf, *J. Chem. Soc. Perkin Trans.* 1 1999, 479.) Flash chromatography (FC): 0.4 bar on silica gel 60H (Merck, Darmstadt, Germany). Thin-layer chromatography (TLC): Aluminum sheets, silica gel 60 F$_{254}$ (0.2 mm, Merck, Germany). Solvent systems for FC and TLC: CH$_2$Cl$_2$/MeOH 9:1(A), CH$_2$Cl$_2$/MeOH 95:5 (B), CH$_2$Cl$_2$/acetone 9:1 (C), CH$_2$Cl$_2$/EtOAc 85:15 (D), CH$_2$Cl$_2$/acetone 95:5 (E). M.p.: Büchi-SMP-20 apparatus (Büchi, Switzerland); uncorrected. NMR Spectra: Avance-DPX-250 and AMX-500 spectrometers (Bruker, Germany); δ values are in ppm downfield from internal SiMe$_4$ (1H, $^{13}$C). Microanalyses were performed by Mikroanalytisches Labor Beller (Göttingen, Germany).

Oligonucleotides

Oligonucleotide synthesis was performed on a DNA synthesizer, model 392 (*Applied Biosystems*, Weiterstadt, Germany). Melting curves were measured with a Cary-1/3 UV/VIS spectrophotometer (Varian, Australia) equipped with a Cary thermoelectrical controller. The temperature was measured continuously in the reference cell with a Pt-100 resistor, and the thermodynamic data of duplex formation were calculated using the Meltwin 3.0 program (J. A. McDowell, D. H. Turner, *Biochemistry* 1996, 35, 14077). The CD-spectra were recorded with a Jasco-600 (Jasco, Japan) spectropolarimeter with thermostatically (Lauda-RCS-6 bath) controlled 1 cm cuvettes. UV-Spectra: 150-20 spectrometer (Hitachi, Japan). The enzymatic hydrolysis of the oligomers was performed as describeda) (F. Seela, G. Becher, *Helv. Chim. Acta* 2000, 83, 928; F. Seela, G. Becher, M. Zulauf, *Nucleosides Nucleotides* 1999, 18, 1399) using the following extinction coefficients: ε$_{260}$: $^7$G$_d$ 2700, dT 8800, dC 7300, dA 15400, dG 11700, 2a 8800, 2b 8700, 2c 8700, 3a 10000, 3b 4800, 3c 3700. Snake-venom phosphodiesterase (EC 3.1.15.1, *Crotallus durissus*) and alkaline phosphatase (EC 3.1.3.1, E. coli) were generous gifts from Roche Diagnostics GmbH, Germany. The MALDI-TOF-spectra were measured on a Biflex III spectrometer (Bruker Saxonia, Leipzig, Germany).

Synthesis and Purification of Oligonucleotides.

The synthesis was carried out in a 1-µmol scale using 3'-phosphoramidites of [(MeO)$_2$Tr]ib$^2$G$_d$, [(MeO)$_2$Tr]bz$^6$A$_d$, [(MeO)$_2$Tr]bz$^4$C$_d$ and [(MeO)$_2$Tr]T$_d$ for the synthesis of oligonucleotides containing 2a-c. and [(MeO)$_2$Tr]tac$^2$G$_d$, [(MeO)$_2$Tr]tac$^6$A$_d$, [(MeO)$_2$Tr]tac$^4$C$_d$ and [(MeO)$_2$Tr]T$_d$ for the synthesis of oligonucleotides containing 3a-c. After cleavage of the oligonucleotides from the solid support, the first were deprotected in 25% aq. NH$_3$ for 12-15 h at 60°. The latter were incubated in 25% aq. NH$_3$ for 1.5-2 h at r. t. for deprotection. The purification of the 5'-(dimethoxytrityl)-oligomers was performed by reversed-phase HPLC(RP-18). The following solvent gradient was used (A, 0.1 M (Et$_3$NH) OAc (pH 7.0)/MeCN 95:5; B, MeCN): 3 min 20% B in A, 12 min 20-40% B in A with a flow rate of 1.0 ml/min. The concentrated oligonucleotide solutions were treated with 2.5% CHCl$_2$COOH/CH$_2$Cl$_2$ for 5 min at r.t. to remove the 4,4'-dimethoxytrityl residues. The detritylated oligomers were purified by reversed-phase HPLC with the gradient 20 min 0-20% B in A with a flow rate of 1 ml/min. The oligomers were desalted on a short column (RP-18, silica gel) and then lyophilized on a Speed-Vac evaporator to yield colorless solids which were frozen at −24°. The purified oligomers were dissolved in 100 µl of double-distilled H$_2$O, and the purity was controlled by ion-exchange chromatography on a Dionex-Nucleopac-PA-100 HPLC column (4×250 mm, P/N 043010; Dionex, Idstein, Germany).

Nucleoside-Composition Analysis.

The oligonucleotides were dissolved in 0.1M Tris-HCl buffer (pH 8.3, 200 µl), and treated with snake-venom phosphodiesterase (3 µl) at 37° for 45 min, and then alkaline phosphatase (3 µl) at 37° for another 30 min The reaction mixtures were analyzed on reversed-phase HPLC(RP-18, at 260 nm, gradient A, 0.7 ml/min). The retention time of 2a-c and 3a-c were used as standards (FIG. 5). The extinction coefficients of the nucleosides and the peak areas were used for quantification of the composition of the oligonucleotides (FIG. 5a-d).

1-(2-Deoxy-β-D-erythro-pentofuranosyl)-3-iodo-1H-pyrazolo[3,4-d]-pyrimidin-4,6-diamine (2c). A soln. of compd. 6-amino-1-[2-deoxy-β-D-erythro-pentofuranosyl]-3-iodo-4-isopropoxy-1H-pyrazolo[3,4-d]pyrimidine 12 (F. Seela, G. Becher, Synthesis 1998, 2, 207.) (1 g, 2.3 mmol) in a aq. 25% NH$_3$ soln. (80 ml) was heated at 70° C. for 4 d. The solvent was evaporated to dryness, the residue dissolved in hot water and crystallized. Colorless needles (640 mg, 71%). M.p. 154°. TLC (A): R$_f$ 0.2. UV (MeOH): 223 (31800), 260 (8700), 278 (9100). $^1$H-NMR ((D$_6$)DMSO): 2.12 (m, H$_\alpha$—C (2')); 2.67 (m, H$_\beta$—C(2')); 3.38, 3.44 (m, H$_2$—C(5')); 3.73 (m, H—C(4')); 4.33 (m, H—C(3')); 4.73 (t, J=5.7, OH—C (5')); 5.17 (d, J=4.3, OH—C(3')); 6.27, J=6.5, H—C(1')); 6.34 (br, NH$_2$); 6.62 (br, NH$_2$). Anal. calc. for C$_{10}$H$_{13}$IN$_6$O$_3$ (392.2): C, 30.63; H, 3.34; N, 21.43. found: C, 30.91; H, 3.61; N, 21.27.

3-Bromo-1-(2-deoxy-β-D-erythro-pentofuranosyl)-4,6 [(2-methylpropanoyl-amino]-1H-pyrazolo[3,4-d]pyrimidine (12a). Compd. 2b (F. Seela, G. Becher, Synthesis 1998, 2, 207) (0.74 g, 2.14 mmol) was co-evaporated with anhyr. pyridine for three times and dissolved in anhydr. pyridine (5 ml) while stirring at r.t. Me$_3$SiCl (1.37 ml, 10.8 mmol), and after 15 min isobutyric anhydride (3.56 ml, 21.5 mmol) were added. Stirring was continued for 3 h. The reaction mixture was cooled in an ice-bath and diluted with H$_2$O (2.5 ml), 5 min later aq. 25% NH$_3$ (4.3 ml) was added. After stirring for 30 min the reaction mixture was evaporated to dryness and coevaporated with toluene (three times). The residue was purified by FC(CH$_2$Cl$_2$/MeOH 9:1) furnishing two zones. From the fast migrating zone compound 13a was obtained as a colorless amorphous solid (500 mg, 48%). R$_f$(A) 0.4. UV (MeOH): 284 (9500), 239 (33900). $^1$H-NMR ((D$_6$)DMSO): 1.15 (m, 2 CH(CH$_3$)$_2$); 2.25 (m, H$_\alpha$—C(2')); 2.75 (m, H$_\beta$—C (2')); 2.86 (m, 2 CH(CH$_3$)$_2$); 3.47 (m, H$_2$—C(5')); 3.81 (m, H—C(4')); 4.44 (m, H—C(3')); 4.73 (t, J=5.5, OH—C(5')); 5.32 (d, J=4.3, OH—C(3')); 6.54 ('t', J=6.6, H—C(1')); 10.59, 10.72 (2 s, 2 NH). Anal. calc. for C$_{18}$H$_{25}$BrN$_6$O$_5$ (485.3): C, 44.55; H, 5.19; N, 17.32. found C, 44.90; H, 5.28; N, 16.81.

4-Amino-3-bromo-1-(2-deoxy-β-D-erythro-pentofuranosyl)-6[(2-methylpropanoyl)amino]-1H-pyrazolo[3,4-d]pyrimidine (14). The slower migrating zone from the above reaction afforded compound 14 as a colorless amorphous solid (0.2 g, 22%). R$_f$ (A) 0.36. UV (MeOH): 282 (10900), 237 (49500). $^1$H-NMR ((D$_6$)DMSO): 1.04, 1.07 (m, CH(CH$_3$)$_2$); 2.21 (m, H$_\alpha$—C(2')); 2.71 (m, H$_\beta$—C(2')); 2.90 (m, CH (CH$_3$)$_2$); 3.46 (m, H$_2$—C(5')); 3.78 (m, H—C(4')); 4.38 (m, H—C(3')); 4.72 (t, J=5.6, OH—C(5')); 5.28 (d, J=4.3, OH—C(3')); 6.42 ('t', J=6.4, H—C(1')); 6.96, 7.76 (br, NH$_2$); 10.08 (br, NH). Anal. calc. for C$_{14}$H$_{19}$BrN$_6$O$_4$ (415.2): C, 40.49; H, 4.61; N, 20.24. found C, 40.58; H, 4.72; N, 19.93.

1-[2-Deoxy-β-D-erythro-pentofuranosyl]-4,6-dibenzamido-3-iodo-1H-pyrazolo-pyrimidine (13b). Compound 2c (1.0 g, 2.55 mmol) was co-evaporated twice with toluene. It was dissolved in anhydr. pyridine (40 ml), and TMS-Cl (3.25 ml, to 25.5 mmol) was added while stirring. The reaction mixture was stirred under argon atmosphere, cooled to 0°, and PhCOCl (3.0 ml, 25.8 mmol) was added dropwise within 30 min. After stirring overnight at r.t, the mixture was diluted with EtOAc (200 ml), washed with a sat. aq. NaHCO$_3$ soln. (200 ml) and ice-cold H$_2$O (200 ml). The aq. phase was extracted with EtOAc (2×400 ml). The combined org. phases were evaporated to dryness and the residue dissolved in THF/ MeOH/H$_2$O (250 ml, 5:4:1). The dark orange soln. was cooled to 0° C., then 2 N NaOH (25 ml) was added, and stirring was continued for another 40 min The residue was purified by FC(CH$_2$Cl$_2$/MeOH, 98:2→CH$_2$Cl$_2$/MeOH, 95:5) to yield an amorphous solid (1.15 g, 75%). TLC (B): R$_f$ 0.4. UV (MeOH): 244 (17400), 276 (14200). $^1$H-NMR ((D$_6$) DMSO)': 2.13 (m, H$_\alpha$—C(2')); 2.67 (m, H$_\beta$—C(2')); 3.38, 3.52 (m, H$_2$—C(5')); 3.84 (m, H—C(4')); 4.46 (m, H—C(3')); 4.72 (t, J=5.7, OH—C(5')); 5.29 (d, J=4.4, OH—C(3')); 6.66 ('t', J=6.5, H—C(1')); 7.51-8.11 (m, arom. H); 10.54, 10.78 (s, 2 NH). Anal. calc. for C$_{24}$H$_{21}$IN$_6$O$_5$ (586.4): C, 48.01; H, 3.53; N, 14.00. found: C, 47.93; H, 3.53; N, 14.05.

3-Bromo-1-[2-deoxy-5-O-(4,4'-dimethoxytrityl)-β-D-erythro-pentofuranosyl]-4,6-diisobutyrylamino-1H-pyrazolo[3,4-d]pyrimidine (15a). Compound 13a (0.5 g, 1.03 mmol) was coevaporated with anhydr. pyridine for three times and dissolved in pyridine (1.5 ml). DMT-Cl (0.45 g, 1.33 mmol) was added, and the mixture was stirred at r.t. for 3 h. The reaction was quenched by addition of MeOH and the mixture evaporated to dryness and coevaporated with toluene for three times. FC(CH$_2$Cl$_2$: MeOH, 10:1)) gave 15a as a colorless foam (0.57 g, 70%). R$_f$ (B) 0.3. UV (MeOH): 237 (52000), 283 (10500). $^1$H-NMR ((D$_6$)DMSO): 1.04-1.17 (m, 2 (CH$_3$)$_2$CH)); 2.29 (m, H$_\alpha$—C(2')); 2.85 (m, H$_\beta$—C(2')); 2.89 (m, 2 (CH$_3$)$_2$CH)); 3.07 (m, H$_2$—C(5')); 3.71 (s, 2 MeO); 3.94 (m, H—C(4')); 4.46 (m, H—C(3')); 5.35 (m, OH—C(3')); 6.57 (m, H—C(1')); 10.57, 10.74 (s, 2 NH). Anal. calc. for C$_{39}$H$_{43}$BrN$_6$O$_7$ (787.2): C, 59.47; H, 5.46; N, 10.67. found: C, 59.08; H, 5.37; N, 10.39.

3-Bromo-1-[2-deoxy-5-O-(4,4'-dimethoxytriphenylmethyl)-β-D-erythro-pentofuranosyl]-4,6-diisobutyrylamino-1H-pyrazolo[3,4-d]pyrimidine 3'-[(2-Cyanoethyl)-N,N-diisopropylphosphoramidite (16a). To a soln. of compound 15a (0.24 g, 0.3 mmol) in anhydr. CH$_2$Cl$_2$ (3 ml) (Ar) (iPr)$_2$EtN (0.16 ml, 0.9 mmol) and 2-cyanoethyl diisopropylphosphoramidochloridite (91 µl, 0.41 mmol) was added, and the mixture was stirred at r. t. for 30 min. The reaction was monitored by TLC. Then, the reaction mixture was diluted with CH$_2$Cl$_2$, and the soln. washed with a 5% aq. NaHCO$_3$ soln. twice and with brine. The organic phase was dried (Na$_2$SO$_4$), concentrated, and the product was separated by FC to yield a colorless foam (0.25 g, 84%). R$_f$(E), 0.63, 0.69. UV (MeOH): 282 (10000), 237 (49500). $^{31}$P-NMR (CDCl$_3$), 149.61, 149.65. $^1$H-NMR ((D$_6$)DMSO): 1.11-1.35 (m, 4 CH(CH$_3$)$_2$); 2.51 (m, H$_\alpha$—C(2)); 2.66 (m, H$_\beta$—C(2')); 2.95-3.91 (m, H$_2$—C (5')); CH(CH$_3$)$_2$; CH$_2$CH$_2$); 3.80 (s, MeO), 4.26 (m, H—C (4')); 4.82 (m, H—C(3')); 6.71 (m, H—C(1')); 6.75-7.44 (m, arom. H); 8.39, 8.59 (br, 2 NH). Anal. calc. for C$_{48}$H$_{60}$BrN$_8$O$_8$P (921.2): C, 58.36; H, 6.08; N, 11.35. found: C, 58.86; H, 6.18; N, 11.55.

1-[2-Deoxy-5-O-(4,4'-dimethoxytrityl)-β-D-erythro-pentofuranosyl]-4,6-dibenzamido-3-iodo-1H-pyrazolo-pyrimidine (15b). Compound 13b (450 mg, 0.75 mmol) was coevaporated twice with anhydr. pyridine. The residue was dissolved in pyridine (2 ml) and dimethoxytrityl chloride (305 mg, 0.9 mmol) was added. After 4 h stirring, the soln. was diluted with 5 ml of MeOH and washed with a 5% aq. NaHCO$_3$ soln. (3×20 ml). The organic phase was dried (Na$_2$SO$_4$) and concentrated to dryness. The residue was purified by FC(CH$_2$Cl$_2$/acetone, 95:5→CH$_2$Cl$_2$/acetone, 9:1) yielding 375 mg (55%) of a colorless foam. TLC(CH$_2$Cl$_2$/acetone 9:1): R$_f$(B) 0.4. UV (MeOH): 244 (16900), 276 (16200). $^1$H-NMR ((D$_6$)DMSO): 2.35 (m, H$_\alpha$—C(2')); 2.67 (m, H$_\beta$—C(2')); 3.07, 3.09 (2 m, H$_2$—C(5')); 3.70 (s, 2 OCH$_3$); 3.96 (m, H—C(4')); 4.56 (m, H—C(3)); (d, J=4.8, OH—C(3')); 6.72-8.11 (m, arom. H); 10.54, 10.78 (2 s, 2 NH). Anal. calc. for C$_{45}$H$_{39}$IN$_6$O$_7$ (902.73): C, 59.87; H, 4.35; N, 9.31. found: C, 59.93; H, 4.33; N, 9.39.

1-[2-Deoxy-5-O-(dimethoxytrityl)-β-D-erythro-pentofuranosyl]-4,6-dibenzamido-3-iodo-1H-pyrazolo[3,4-d]-pyrimidine 3'-[(2-Cyanoethyl-N,N-diisopropylphosphoramidite] (16b). Compound 15b (330 mg, 0.37 mmol) was dissolved in THF (5 ml). (iPr)$_2$EtN (186 μl, 1.07 mmol) and 2-cyanoethyl diisopropylphosphoramidochloridite (108 μl, 0.48 mmol) were added under argon atmosphere. After 30 min the mixture was diluted with CH$_2$Cl$_2$ (20 ml) and a 5% aq. NaHCO$_3$ soln (2×20 ml). The mixture was extracted with CH$_2$Cl$_2$ (3×15 ml). The combined organic layer was dried (Na$_2$SO$_4$) and evaporated to an oil. The residue was submitted to FC(CH$_2$Cl$_2$/EtOAc, 85:15) yielding 280 mg (69%) of a colorless foam. TLC (D): R$_f$ 0.8. $^{31}$P-NMR (CDCl$_3$): 149.37, 149.38.

Example 3

Investigation of Array Precursor Compounds

According to standard methodology, the oligonucleotides shown in Table 19 were synthesized from the phosphoramidites according to this invention 19 (=8a and 16a) to 23 in scheme 11 and standard A, G, C and T phosphoramidites as already described above. The phosphoramidites are also available from Glen Research and were used according to the manufacturer's instructions (Orderung numbers: 10-1906-02 (20), 10-1964-02 (21), 10-1056-02 (22), 10-1067-02 (23)). The hybridisation behaviour was investigated as described using UV/VIS spectroscopy measuring temperature dependent absorption at a wavelength of 260 nm.

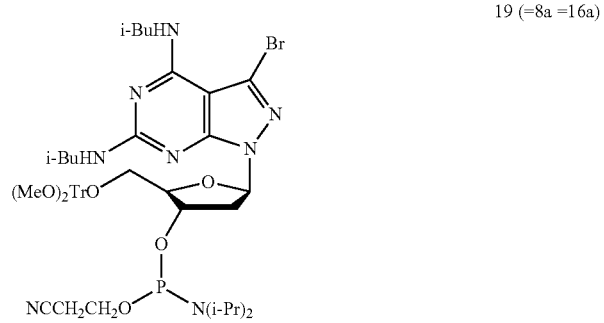

19 (=8a =16a)

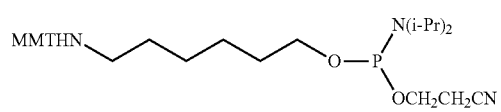

20

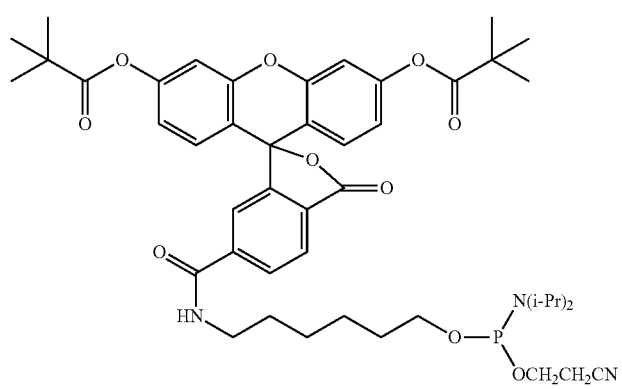

21

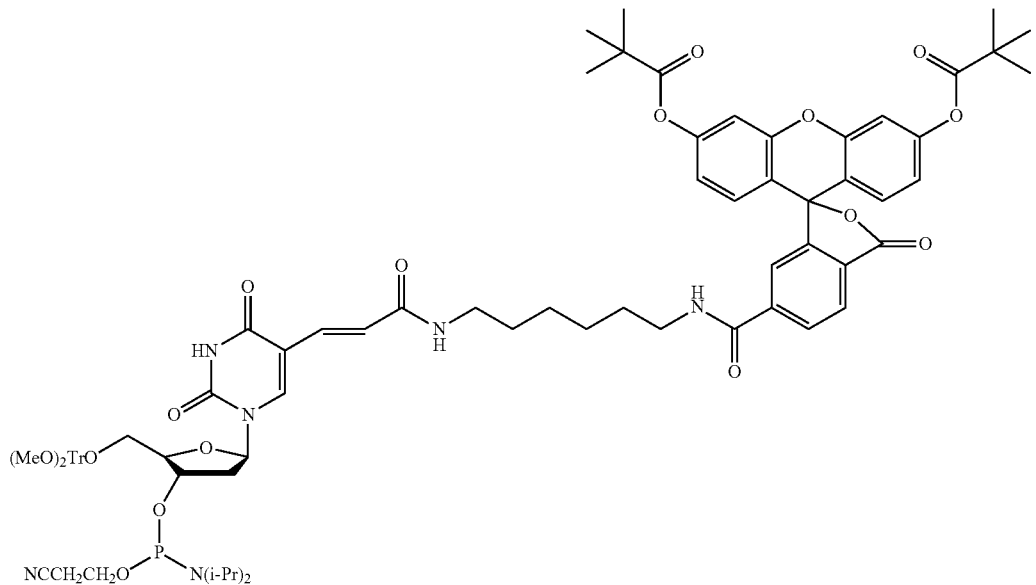
22
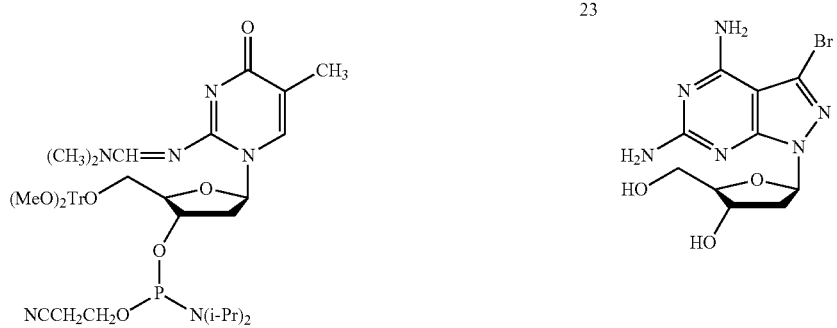
23
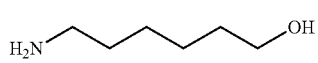
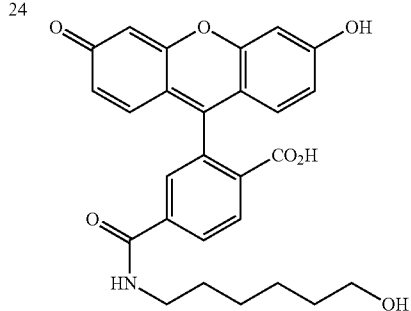
2b
24
25

-continued

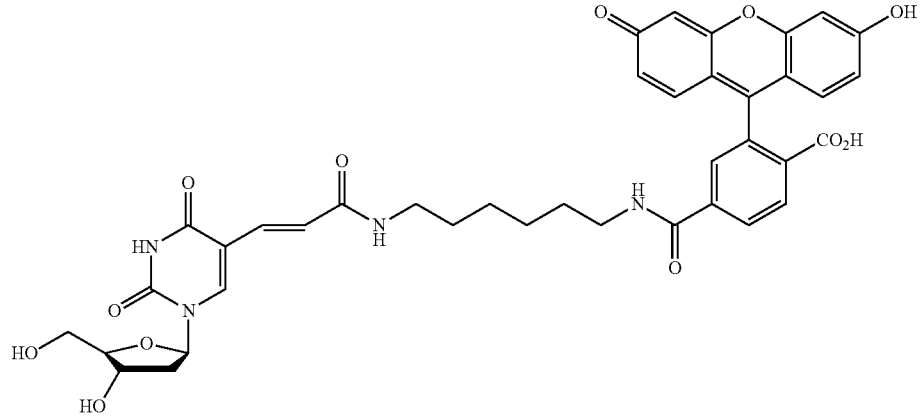

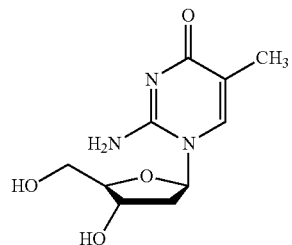

TABLE 19

$T_m$-Values and Thermodynamic Data of Duplex Formation of Antiparallel or Parallel Oligonucleotide Dupelxes Carrying Fluorescent Reporter Groups and/or Aminoalkyl Linkers for the Immobilization on Arrays[a)].

| Oligonucleotide | SEQ ID NO: | $T_m$ [° C.] | ΔH° [kcal/mol] | ΔS° [cal/K mol] | ΔG°$_{310}$ [kcal/mol] |
|---|---|---|---|---|---|
| 5'-d(TAG GTC AAT ACT) (102) · (103)<br>3'-d(ATC CAG TTA TGA) | 2<br>3 | 47 | −86.8 | −243.7 | −11.3 |
| 5'-d(TAG GTC 2b2bT ACT) (110) · (103)<br>3'-d(ATC CAG TTA TGA) | 10<br>3 | 56 | −91.4 | −251.7 | −13.4 |
| 5'-d(24 TAG GTC AAT ACT) (500) · (103)<br>3'-d(ATC CAG TTA TGA) | 31<br>3 | 49 | −90.0 | −254.4 | −11.1 |
| 5'-d(24 TAG GTC 2b2bT ACT) (501) · (103)<br>3'-d(ATC CAG T T A TGA) | 32<br>3 | 56 | −87.2 | −239.3 | −13.0 |
| 5'-d(24 TAG GTC AAT ACT) (500) · (502)<br>3'-d(ATC CAG TTA TGA 25) | 31<br>33 | 49 | −95.2 | −270.8 | −11.2 |
| 5'-d(24 TAG GTC 2b2bT ACT) (501) · (502)<br>3'-d(ATC CAG T T A TGA 25) | 32<br>33 | 56 | −92.7 | −256.6 | −13.1 |
| 5'-d(24 TAG GTC AAT ACT) (500) · (503)<br>3'-d(ATC CAG TTA TGA 26) | 31<br>34 | 50 | −86.5 | −242.7 | −11.2 |
| 5'-d(24 TAG GTC 2b2bT ACT) (501) · (503)<br>3'-d(ATC CAG T T A TGA 26) | 32<br>34 | 58 | −95.1 | −262.1 | −13.8 |
| 5'-d(T 27 A TAA 27 T 27 27 TA) (504) · (505)<br>5'-d(A G T ATT G AG G AT) | 35<br>36 | 42 | −77.1 | −220.6 | −8.7 |
| 5'-d(24 T 27 A TAA 27 T 27 27 TA) (506) · (507)<br>5'-d(A G T ATT G A G G AT 26) | 37<br>38 | 43 | −71.9 | −201.8 | −9.3 |

TABLE 19-continued

T$_m$-Values and Thermodynamic Data of Duplex Formation of Antiparallel or Parallel Oligonucleotide Dupelxes Carrying Fluorescent Reporter Groups and/or Aminoalkyl Linkers for the Immobilization on Arrays[a].

| Oligonucleotide | SEQ ID NO: | T$_m$ [° C.] | ΔH° [kcal/mol] | ΔS° [cal/K mol] | ΔG°$_{310}$ [kcal/mol] |
|---|---|---|---|---|---|
| 5'-d(24 T 27 A T2b2b 27 T 27 27 TA) (508)·(507) | 39 | 48 | -93.7 | -265.4 | -11.3 |
| 5'-d(A G T AT T G A G G AT 26) | 38 | | | | |

[a] Measured UV-spectrophotometrically at 260 nm in 10 mM Na-cacodylate, 10 mM MgCl$_2$, 100 mM NaCl (pH 7) at 5 µM + 5 µM of single strand concentration. The thermodynamic data were calculated using the program MeltWin (3.0).

It could be shown that the melting behaviour is very similar in the parallel and antiparallel mode even when labelled with reporter groups. The situation is similar to the situation when the nucleic acid binding compound according to the invention is bound to surface or builds up an array or when it binds to an array of natural or non-natural nucleic acid binding compounds exemplifying the usefulness of the present invention. This is exemplified by the oligonucleotide 501 containing a linker by which it can attached to a solid phase and hybridizes to a labelled target nucleic acid like the oligonucleotide 503.

Example 4

Visualization of Antiparallel and Parallel Hybridization

The hydrogen bonding interaction pattern in parallel or antiparallel duplexes is visualized in scheme 12 and 13.

Scheme 12

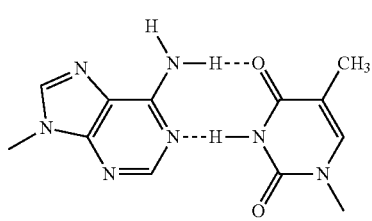

Watson Crick AT-Base Pair I
antiparallel

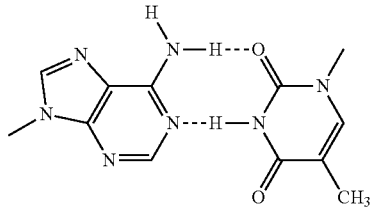

Reverse Watson Crick AT-Base Pair II
parallel

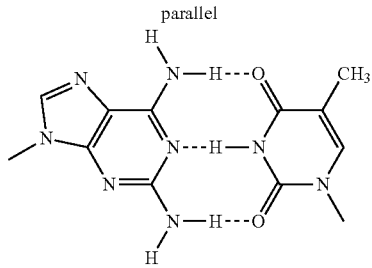

Watson Crick n$^2$AT-Base Pair III
antiparallel

-continued

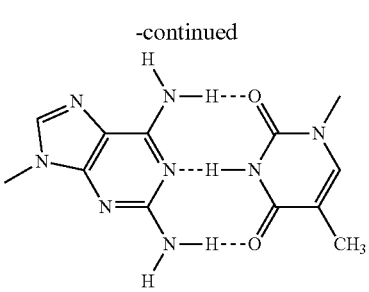

Reverse Watson Crick n$^2$AT-Base Pair IV
parallel

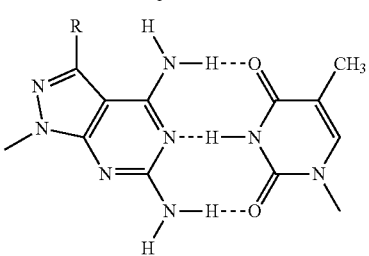

Watson Crick PT-Base Pair V
R = H, Br, I parallel

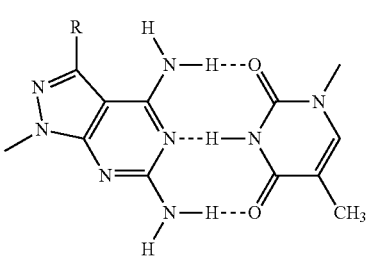

Reverse Watson Crick PT-Base Pair VI
R = H, Br, I
parallel

Scheme 13

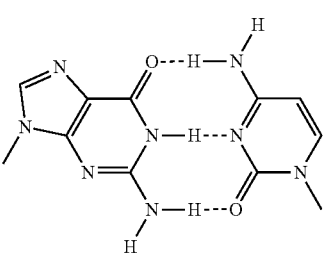

Watson Crick GC-Base Pair VII antiparallel

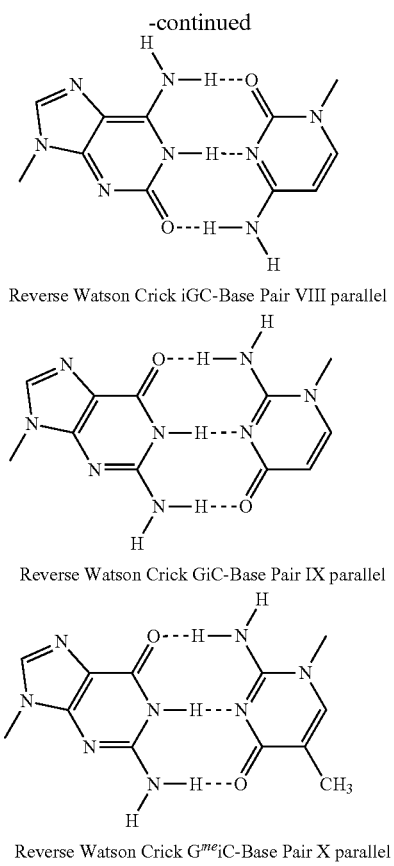

Reverse Watson Crick iGC-Base Pair VIII parallel

Reverse Watson Crick GiC-Base Pair IX parallel

Reverse Watson Crick G$^{me}$iC-Base Pair X parallel

REFERENCES

[1] N. Ramzaeva, F. Seela, Helv. Chim. Acta 1996, 79, 1549.
[2] F. Seela, M. Zulauf, J. Chem. Soc., Perkin Trans. 1 1999, 479.
[3] F. Seela, G. Becher, Helv. Chim. Acta 1999, 82, 94.
[4] B. L. Gaffney, L. A. Marky, R. A. Jones, Tetrahedron 1984, 40, 3.
[5] C. Bailly, M. J. Waring, Nucleic Acids Res. 1998, 26, 4309.
[6] A. Chollet, E. H. Kawashima, Nucleic Acids Res. 1988, 16, 305.
[7] A. Chollet, A. Chollet-Damerius, E. H. Kawashima, Chem. Scri. 1986, 26, 37.
[8] F. B. Howard, H. T. Miles, Biochemistry 1983, 22, 597.
[9] G. M. Lamm, B. J. Blencowe, B. S. Sproat, A. M. Iribarren, U. Ryder, A. I. Lamond, Nucleic Acids Res. 1991, 19, 3193.
[10] J. D. Hoheisel, H. Lehrach, FEBS Lett. 1990, 274, 103.
[11] J. Sági, E. Szakonyi, M. Vorlícková, J. Kypr, J. Biomolec. Struct. Dyn. 1996, 13, 1035.
[12] S. Gryaznov, R. G. Schultz, Tetrahedron Lett. 1994, 35, 2489.
[13] G. Haaima, H. F. Hansen, L. Christensen, O. Dahl, P. E. Nielsen, Nucleic Acids Res. 1997, 25, 4639.
[14] V. Boudou, L. Kerremans, B. De Bouvere, E. Lescrinier, G. Schepers, R. Busson, A. Van Aerschot, P. Herdewijn, Nucleic Acids Res. 1999, 27, 1450.
[15] F. Seela, H. Driller, Helv. Chim. Acta 1988, 71, 757.
[16] G. Balow, V. Mohan, E. A. Lesnik, J. F. Johnston, B. P. Monia, O. L. Acevedo, Nucleic Acids Res. 1998, 26, 3350.
[17] F. Seela, H. Steker, H. Driller, U. Bindig, Liebigs Ann. Chem. 1987, 15.
[18] F. Seela, G. Becher, Synthesis 1998, 207.
[19] L. D. Garaeva, I. V. Yartseva, S. Y. Melnik, Nucleosides Nucleotides 1991, 10, 1295.
[20] F. Oertel, H. Winter, Z. Kazimierczuk, J. A. Vilpo, P. Richter, F. Seela, Liebigs Ann. Chem. 1992, 1165.
[21] J. Davoll, K. A. Kerridge, J. Chem. Soc. 1961, 2589.
[22] L. D. Garaeva, I. A. Korbukh, Y. V. Dobrynin, T. G. Nikolaeva, M. N. Preobrazhenskaya, Pharm. Chem. J. (Engl. Transl.) 1988, 22, 523.
[23] J. van Wijk, C. Altona, 'PSEUROT 6.2—A Program for the Conformational Analysis of the Five-Membered Rings', University of Leiden, July 1993; C. A. G. Haasnoot, F. A. A. M. de Leeuw, C. Altona, Tetrahedron 1980, 86, 2783.
[24] F. Seela, G. Becher, H. Rosemeyer, H. Reuter, G. Kastner, I. A. Mikhailopulo, Helv. Chim. Acta 1999, 82, 105.
[25] G. Blackburn, M. J. Gait, in 'Nucleic Acids in Chemistry and Biology', IRL Press, Oxford University Press 1990, p. 28.
[26] B. S. Sproat, A. M. Iribarren, R. G. Garcia, B. Beijer, Nucleic Acids Res. 1991, 19, 733.
[27] A. Cano, M. F. Goodman, R. Eritja, Nucleosides Nucleotides 1994, 13, 501.
[28] I. Luyten, A. Van Aerschot, J. Rozenski, R. Busson, P. Herdewijn, Nucleosides Nucleotides 1997, 16, 1649.
[29] G. S. Ti, B. L. Gaffney, R. A. Jones, J. Am. Chem. Soc. 1982, 104, 1316.
[30] K. Groebke, J. Hunzicker, W. Fraser, L. Peng, U. Diederichsen, K. Zimmerman, A. Holzner, Ch. Leumann, A. Eschenmoser, Helv. Chim. Acta 1998, 81, 175.
[31] B. C. Froehler, P. G. Ng, M. D. Matteucci, Nucleic Acids Res. 1986, 14, 5399.
[32] N. D. Sinha, J. Biernat, J. McManus, H. Köster, Nucleic Acids Res. 1984, 12, 4539.
[33] L. J. McBride, R. Kierzek, S. L. Beaucage, M. H. Caruthers, J. Am. Chem. Soc. 1986, 108, 2040.
[34] F. Seela, C. Wei, A. Melenewski, Y. He, R. Kröschel, E. Feiling, Nucleosides Nucleotides 1999, 18, 1543.
[35] F. Seela, A. Melenewski, Eur. J. Org. Chem. 1999, 485.
[36] F. Seela, G. Becher, Helv. Chim. Acta 2000, 83, 928.
[37] F. Seela, C. Wei, Helv. Chim. Acta 1999, 82, 726.
[38] M. D. Kirnos, I. Y. Khudyakov, N. I. Alexandrushkina, B. F. Vanyushin, Nature 1977, 270, 369.
[39] F. B. Howard, C. Chen, J. S. Cohen, H. T. Miles, Biochem. Biophys. Res. Commun. 1984, 118, 848.
[40] E. A. Lesnik, S. M. Freier, Biochemistry, 1995, 34, 10807.
[41] Ribozyme Pharmaceuticals Inc., 2950 Wilderness Place, Boulder, Colo. 80301, USA.
[42] F. Seela, C. Wei, G. Becher, M. Zulauf, P. Leonard, Bio. Org. Med. Chem. Lett. 2000, 10, 289.
[43] J. A. McDowell, D. H. Turner, Biochemistry, 1996, 35, 14077.

The invention claimed is:

1. A method for the determination of the presence, absence or amount of a nucleic acid comprising:
providing a sample suspected to contain the nucleic acid,
providing a nucleic acid binding compound comprising a backbone, said backbone having attached one or more heterocyclic groups capable of base pairing to nucleobases, characterized in that at least one of said heterocyclic groups is a group of formula I,

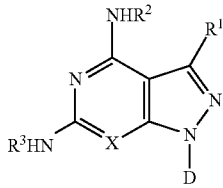

Formula I wherein
$R^1$ is independent from X, $R^2$ or $R^3$ and is selected from the group consisting of —Br and —I
$R^2$ and $R^3$ are independent from each other and from X and $R^1$, and are selected from the group consisting of:
(1) —H,
(2) ($C_1$-$C_{10}$)-alkyl,
(3) ($C_2$-$C_{10}$)-alkenyl,
(4) ($C_2$-$C_{10}$)-alkynyl,
(5) ($C_6$-$C_{22}$)-aryl,
(6) —Z—($C_1$-$C_{10}$)-alkyl, —Z—($C_2$-$C_{10}$)-alkenyl, —Z—($C_2$-$C_{10}$)-alkynyl, —Z—($C_6$-$C_{22}$)-aryl, or Z—H, wherein Z=—CO—, —CO—NH—, —CS—NH—, —(CH$_2$)$_n$—[O—(CH$_2$)$_r$]$_s$—, where r and s are, independently of each other, an integer between 1 to 18 and n is 1 or 2 independently from r and s,
(7) substituents (2) to (6), wherein any alkyl, alkenyl, alkynyl or aryl is unsubstituted or substituted by one or more moieties selected from the group consisting of -halogen, —NO$_2$, —OR$^{12}$, —CN, —($C_1$-$C_6$)-alkoxy, —SH, —S—($C_1$-$C_6$)-alkyl, —NR$^5$R$^6$, —N$^+$R$^5$R$^6$R$^{12}$, —COR$^{11}$, —NH—CONR$^5$R$^6$, —NH—CSNR$^5$R$^6$ and —(CH$_2$)$_n$—[O—(CH$_2$)$_r$]$_s$—NR$^5$R$^6$, r, and s are independently of each other an integer of from 1 to 18 and n is 0 or 1 independently from r and s,
wherein $R^{11}$ is selected from the group consisting of —NHR$^{12}$ and OR$^{12}$,
wherein $R^5$, $R^6$ and $R^{12}$ are selected independently from the group consisting of —H, —($C_1$-$C_{10}$)-alkyl, —($C_2$-$C_{10}$)-alkenyl, —($C_2$-$C_{10}$)-alkynyl, —($C_6$-$C_{22}$)-aryl and a reporter group,
X is N; and
D is the position of attachment of the group to the rest of the nucleic acid binding compound;
or any salts thereof,
contacting said sample with the nucleic acid binding compound under conditions for binding the nucleic acid binding compound to the nucleic acid to form a duplex, and
determining the binding product or the degree of hybridization between the nucleic acid and the nucleic acid binding compound as a measure of the presence, absence or amount of the nucleic acid.

2. The method according to claim 1, wherein the nucleic acid binding compound comprises a reporter group.

3. The method according to claim 2 wherein the reporter group is a fluorescent label.

4. The method according to claim 3 wherein the nucleic acid binding compound further comprises a quenching agent which quenches the fluorescence emission of the fluorescent label.

5. The method according to claim 4 wherein the fluorescent label is a fluorescein and wherein the quenching agent is a fluorescent rhodamine or cyanine.

6. The method according to claim 4, further comprising altering the spatial relationship between the fluorescent label and the quenching agent subsequent to hybridization.

7. The method according to claim 6, wherein alteration of the spatial relationship between the fluorescent label and the quenching agent is accomplished by exonuclease hydrolysis of the nucleic acid binding compound, wherein release of label occurs as a result of exonuclease hydrolysis.

8. The method according to claim 7, wherein the degree of hybridization between the nucleic acid binding compound and the nucleic acid is determined by the quantity of label that is released from the nucleic acid binding compound subsequent to hybridization.

9. The method according to claim 1, wherein the degree of hybridization between the nucleic acid binding compound and the nucleic acid is determined by the priming ability of the nucleic acid binding compound.

10. The method according to claim 9, wherein priming occurs as part of a polymerase chain reaction.

11. The method according to claim 2, wherein more than one nucleic acid binding compound is used.

12. The method according to claim 11, wherein two nucleic acid binding compounds are used.

13. The method according to claim 12, wherein the first of the two nucleic acid binding compounds comprises a fluorescence donor and the second of the two nucleic acid binding compounds comprises a fluorescence acceptor, and wherein the emission wavelengths of the fluorescence donor overlap the absorption wavelengths of the fluorescence acceptor.

14. The method according to claim 13 wherein the degree of hybridization is measured by the quantity of light transferred between the fluorescence donor and the fluorescence acceptor and emitted by the fluorescence acceptor.

15. The method according to claim 13 wherein the degree of hybridization is determined by the measurement of the melting temperature between the nucleic acid binding compound and the nucleic acid.

16. A method for detecting the presence of a target sequence in a nucleic acid, the method comprising
a) providing a nucleic acid which is to be tested for the presence of the target sequence;
b) providing a nucleic acid binding compound comprising a backbone, said backbone having attached one or more heterocyclic groups capable of base pairing to nucleobases, characterized in that at least one of said heterocyclic groups is a group of formula I,

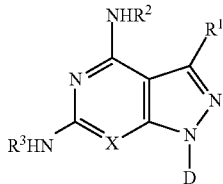

Formula I wherein
$R^1$ is independent from X, $R^2$ or $R^3$ and is selected from the group consisting of —Br and —I;
$R^2$ and $R^3$ are independent from each other and from X and $R^1$, and are selected from the group consisting of:
(1) —H,
(2) $(C_1-C_{10})$-alkyl,
(3) $(C_1-C_{10})$-alkenyl,
(4) $(C_2-C_{10})$-alkynyl,
(5) $(C_6-C_{22})$-aryl,
(6) —Z—$(C_1-C_{10})$-alkyl, —Z—$(C_2-C_{10})$-alkenyl, —Z—$(C_7-C_{10})$-alkynyl, —Z—$(C_6-C_{22})$-aryl or Z—H, wherein Z=—CO—, —CO—NH—, —CS—NH—, —$(CH_2)_n$—[O—$(CH_2)_r]_s$—, where r and s are, independently of each other, an integer between 1 to 18 and n is 1 or 2 independently from r and s,
(7) substituents (2) to (6), wherein any alkyl, alkenyl, alkynyl or aryl is unsubstituted or substituted by one or more moieties selected from the group consisting of -halogen, —$NO_2$, —$OR^{12}$, —CN, —$(C_1-C_6)$-alkoxy, —SH, —S—$(C_1-C_6)$-alkyl, —$NR^5R^6$, —$N^+R^5R^6R^{12}$, —$COR^{11}$, —NH—$CONR^5R^6$, —NH—$CSNR^5R^6$ and —$(CH_2)_n$—[O—$(CH_2)_r]_s NR^5R^6$, r and s are independently of each other an integer of from 1 to 18 and n is 0 or 1 independently from r and s,
wherein $R^{11}$ is selected from the group consisting of —$NHR^{12}$ and $OR^{12}$,
wherein $R^5$, $R^6$ and $R^{12}$ are selected independently from the group consisting of —H, —$(C_2-C_{10})$-alkenyl, —$(C_2-C_{10}$-alkynyl, —$(C_6-C_{22})$-aryl and a reporter group.,
X is N; and
D is the position of attachment of the group to the rest of the nucleic acid binding compound;
or any salts thereof,
wherein the nucleic acid binding compound has a sequence that is substantially complementary to the target sequence;
c) incubating the nucleic acid and the nucleic acid binding compound under hybridization conditions; and
d) identifying hybridized nucleic acids.

17. The method according to claim 16, wherein multiple nucleic acids are tested for the presence of the target sequence, and wherein the nucleic acids have related target sequences.

18. The method according to claim 16, wherein the nucleic acid binding compound is a primer comprising an extendible 3'-hydroxyl group.

19. The method according to claim 18, wherein the hybridized nucleic acids are identified by extending the primer with a polymerizing enzyme.

20. The method according to claim 18, wherein the nucleic acid binding compound is a primer in a polymerase chain reaction.

* * * * *

SEQUENCE LISTING

<160> NUMBER OF SEQ ID NOS: 39

<210> SEQ ID NO 1
<211> LENGTH: 12
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: Synthetic nucleotide based upon adenine
<220> FEATURE:
<221> NAME/KEY: modified_base
<222> LOCATION: (8)..(8)
<223> OTHER INFORMATION: Synthetic nucleotide based upon adenine

<400> SEQUENCE: 1
agtnttgncc ta                                                      12

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
taggtcaata ct                                                      12

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agtattgacc ta                                                      12

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Synthetic nucleotide based upon adenine
<220> FEATURE:
<221> NAME/KEY: modified_base
<222> LOCATION: (7)..(8)
<223> OTHER INFORMATION: Synthetic nucleotide based upon adenine
<220> FEATURE:
<221> NAME/KEY: modified_base
<222> LOCATION: (10)..(10)
<223> OTHER INFORMATION: Synthetic nucleotide based upon adenine

<400> SEQUENCE: 4
tnggtcnntn ct                                                      12

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: Synthetic nucleotide based upon adenine
<220> FEATURE:
```

```
<221> NAME/KEY: modified_base
<222> LOCATION: (8)..(8)
<223> OTHER INFORMATION: Synthetic nucleotide based upon adenine

<400> SEQUENCE: 5
agtnttgncc ta                                                              12

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
taggccggca ct                                                              12

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
agtgccggcc ta                                                              12

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: Synthetic nucleotide based upon adenine

<400> SEQUENCE: 8
taggtcnnta ct                                                              12

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: Synthetic nucleotide based upon adenine
<220> FEATURE:
<221> NAME/KEY: modified_base
<222> LOCATION: (8)..(8)
<223> OTHER INFORMATION: Synthetic nucleotide based upon adenine

<400> SEQUENCE: 9
agtnttgncc ta                                                              12

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (7)..(8)
<223> OTHER INFORMATION: Synthetic nucleotide based upon adenine

<400> SEQUENCE: 10
taggtcnnta ct                                                            12

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: Synthetic nucleotide based upon adenine
<220> FEATURE:
<221> NAME/KEY: modified_base
<222> LOCATION: (8)..(8)
<223> OTHER INFORMATION: Synthetic nucleotide based upon adenine

<400> SEQUENCE: 11
agtnttgncc ta                                                            12

<210> SEQ ID NO 12
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
aguauugacc ua                                                            12

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(4)
<223> OTHER INFORMATION: 2'-deoxy-5-methylisocytidine
<220> FEATURE:
<221> NAME/KEY: modified_base
<222> LOCATION: (6)..(6)
<223> OTHER INFORMATION: 2'-deoxy-5-methylisoguanine
<220> FEATURE:
<221> NAME/KEY: modified_base
<222> LOCATION: (11)..(11)
<223> OTHER INFORMATION: 2'-deoxy-5-methylisoguanine

<400> SEQUENCE: 13
atnnanttat na                                                            12

<210> SEQ ID NO 14
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-deoxy-5-methylisocytidine
```

```
<220> FEATURE:
<221> NAME/KEY: modified_base
<222> LOCATION: (7)..(7)
<223> OTHER INFORMATION: 2'-deoxy-5-methylisocytidine
<220> FEATURE:
<221> NAME/KEY: modified_base
<222> LOCATION: (9)..(10)
<223> OTHER INFORMATION: 2'-deoxy-5-methylisoguanine

<400> SEQUENCE: 14
tnataantnn at                                                              12

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Synthetic nucleotide based upon adenine

<400> SEQUENCE: 15
taggtcnata ct                                                              12

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Synthetic nucleotide based upon adenine
<220> FEATURE:
<221> NAME/KEY: modified_base
<222> LOCATION: (7)..(8)
<223> OTHER INFORMATION: Synthetic nucleotide based upon adenine
<220> FEATURE:
<221> NAME/KEY: modified_base
<222> LOCATION: (10)..(10)
<223> OTHER INFORMATION: Synthetic nucleotide based upon adenine

<400> SEQUENCE: 16
tnggtcnntn ct                                                              12

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: Synthetic nucleotide based upon adenine

<400> SEQUENCE: 17
agtattgncc ta                                                              12

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (4)..(4)
<223> OTHER INFORMATION: Synthetic nucleotide based upon adenine

<400> SEQUENCE: 18
agtnttgacc ta                                                              12

<210> SEQ ID NO 19
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: Synthetic nucleotide based upon adenine

<400> SEQUENCE: 19
taggtcnnta ct                                                              12

<210> SEQ ID NO 20
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Synthetic nucleotide based upon adenine
<220> FEATURE:
<221> NAME/KEY: modified_base
<222> LOCATION: (7)..(8)
<223> OTHER INFORMATION: Synthetic nucleotide based upon adenine
<220> FEATURE:
<221> NAME/KEY: modified_base
<222> LOCATION: (10)..(10)
<223> OTHER INFORMATION: Synthetic nucleotide based upon adenine

<400> SEQUENCE: 20
tnggtcnntn ct                                                              12

<210> SEQ ID NO 21
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Synthetic nucleotide based upon a pyrimidine
      nucleotide
<220> FEATURE:
<221> NAME/KEY: modified_base
<222> LOCATION: (9)..(9)
<223> OTHER INFORMATION: Synthetic nucleotide based upon a pyrimidine
      nucleotide

<400> SEQUENCE: 21
taggncaana ct                                                              12

<210> SEQ ID NO 22
<211> LENGTH: 12
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (5)..(6)
<223> OTHER INFORMATION: Synthetic nucleotide based upon a pyrimidine
      nucleotide

<400> SEQUENCE: 22
agtanngacc ta                                                           12

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Synthetic nucleotide based upon a pyrimidine
      nucleotide
<220> FEATURE:
<221> NAME/KEY: modified_base
<222> LOCATION: (9)..(9)
<223> OTHER INFORMATION: Synthetic nucleotide based upon a pyrimidine
      nucleotide

<400> SEQUENCE: 23
taggncaana ct                                                           12

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(6)
<223> OTHER INFORMATION: Synthetic nucleotide based upon a pyrimidine
      nucleotide

<400> SEQUENCE: 24
agtanngacc ta                                                           12

<210> SEQ ID NO 25
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Synthetic nucleotide based upon a pyrimidine
      nucleotide
<220> FEATURE:
<221> NAME/KEY: modified_base
<222> LOCATION: (9)..(9)
<223> OTHER INFORMATION: Synthetic nucleotide based upon a pyrimidine
      nucleotide

<400> SEQUENCE: 25
taggncaana ct                                                           12

<210> SEQ ID NO 26
<211> LENGTH: 12
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(6)
<223> OTHER INFORMATION: Synthetic nucleotide based upon a pyrimidine
      nucleotide

<400> SEQUENCE: 26
agtanngacc ta                                                           12

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
taggacaata ct                                                           12

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tagggcaata ct                                                           12

<210> SEQ ID NO 29
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
taggccaata ct                                                           12

<210> SEQ ID NO 30
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
aguauugacc ua                                                           12

<210> SEQ ID NO 31
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
taggtcaata ct                                                           12
```

```
<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: Synthetic nucleotide based upon adenine

<400> SEQUENCE: 32
taggtcnnta ct                                                          12

<210> SEQ ID NO 33
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
agtattgacc ta                                                          12

<210> SEQ ID NO 34
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Synthetic nucleotide based upon a pyrimidine
      nucleotide

<400> SEQUENCE: 34
nagtattgac cta                                                         13

<210> SEQ ID NO 35
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Synthetic nucleotide based upon a pyrimidine
      nucleotide
<220> FEATURE:
<221> NAME/KEY: modified_base
<222> LOCATION: (7)..(7)
<223> OTHER INFORMATION: Synthetic nucleotide based upon a pyrimidine
      nucleotide
<220> FEATURE:
<221> NAME/KEY: modified_base
<222> LOCATION: (9)..(10)
<223> OTHER INFORMATION: Synthetic nucleotide based upon a pyrimidine
      nucleotide

<400> SEQUENCE: 35
tnataantnn ta                                                          12

<210> SEQ ID NO 36
<211> LENGTH: 12
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 36
agtattgagg at                                                             12

<210> SEQ ID NO 37
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Synthetic nucleotide based upon a pyrimidine
      nucleotide
<220> FEATURE:
<221> NAME/KEY: modified_base
<222> LOCATION: (7)..(7)
<223> OTHER INFORMATION: Synthetic nucleotide based upon a pyrimidine
      nucleotide
<220> FEATURE:
<221> NAME/KEY: modified_base
<222> LOCATION: (9)..(10)
<223> OTHER INFORMATION: Synthetic nucleotide based upon a pyrimidine
      nucleotide

<400> SEQUENCE: 37
tnataantnn ta                                                             12

<210> SEQ ID NO 38
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: Synthetic nucleotide based upon a pyrimidine
      nucleotide

<400> SEQUENCE: 38
agtattgagg atn                                                            13

<210> SEQ ID NO 39
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Synthetic nucleotide based upon a pyrimidine
       nucleotide
<220> FEATURE:
<221> NAME/KEY: modified_base
<222> LOCATION: (5)..(6)
<223> OTHER INFORMATION: Synthetic nucleotide based upon adenine
<220> FEATURE:
<221> NAME/KEY: modified_base
<222> LOCATION: (7)..(7)
<223> OTHER INFORMATION: Synthetic nucleotide based upon a pyrimidine
      nucleotide
```

```
<220> FEATURE:
<221> NAME/KEY: modified_base
<222> LOCATION: (9)..(10)
<223> OTHER INFORMATION: Synthetic nucleotide based upon a pyrimidine
      nucleotide

<400> SEQUENCE: 39
tnatnnntnn ta                                                         12
```